(12) United States Patent
Noureldin et al.

(10) Patent No.: US 10,443,946 B2
(45) Date of Patent: Oct. 15, 2019

(54) SYSTEMS FOR RECOVERY AND RE-USE OF WASTE ENERGY IN CRUDE OIL REFINING AND AROMATICS COMPLEX

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/833,754

(22) Filed: Dec. 6, 2017

(65) Prior Publication Data

US 2018/0094864 A1    Apr. 5, 2018

Related U.S. Application Data

(63) Continuation of application No. 15/242,186, filed on Aug. 19, 2016, now Pat. No. 9,879,918.
(Continued)

(51) Int. Cl.
*F28D 7/00* (2006.01)
*C01B 3/24* (2006.01)
(Continued)

(52) U.S. Cl.
CPC ............ *F28D 7/0083* (2013.01); *B01D 3/007* (2013.01); *B01D 3/32* (2013.01); *B01D 51/10* (2013.01);
(Continued)

(58) Field of Classification Search
CPC ......... F28D 7/00; F28D 7/0083; C10G 33/06; C10G 45/02; C10G 65/12; C10L 3/10; C07C 7/08
See application file for complete search history.

(56) References Cited

U.S. PATENT DOCUMENTS

| 3,995,428 A | 12/1976 | Roberts |
| 4,109,469 A | 8/1978 | Carson |

(Continued)

FOREIGN PATENT DOCUMENTS

| CN | 1844325 | 10/2006 |
| CN | 101424453 | 5/2009 |

(Continued)

OTHER PUBLICATIONS

International Preliminary Report on Patentability in International Application No. PCT/US2016/048042, dated Mar. 8, 2018, 8 pages.
(Continued)

*Primary Examiner* — Brian A McCaig
(74) *Attorney, Agent, or Firm* — Fish & Richardson P.C.

(57) ABSTRACT

Configurations and related processing schemes of specific inter-plants and hybrid, intra- and inter-plants waste heat recovery schemes for thermal energy consumption reduction in integrated refining-petrochemical facilities synthesized for grassroots medium grade crude oil semi-conversion refineries to increase energy efficiency from specific portions of low grade waste heat sources are described. Configurations and related processing schemes of specific inter-plants and hybrid, intra- and inter-plants waste heat recovery schemes for thermal energy consumption reduction in integrated refining-petrochemical facilities synthesized for integrated medium grade crude oil semi-conversion refineries and aromatics complex for increasing energy efficiency from specific portions of low grade waste sources are also described.

30 Claims, 66 Drawing Sheets

Related U.S. Application Data

(60) Provisional application No. 62/209,217, filed on Aug. 24, 2015, provisional application No. 62/209,147, filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| C01B 3/34 | (2006.01) | |
| C10G 45/44 | (2006.01) | |
| F01K 23/06 | (2006.01) | |
| C10G 45/02 | (2006.01) | |
| C10G 35/04 | (2006.01) | |
| C10L 3/10 | (2006.01) | |
| C07C 7/08 | (2006.01) | |
| C10G 65/12 | (2006.01) | |
| C10G 33/06 | (2006.01) | |
| B01D 3/00 | (2006.01) | |
| B01D 3/32 | (2006.01) | |
| B01D 51/10 | (2006.01) | |
| B01D 53/047 | (2006.01) | |
| B01D 53/14 | (2006.01) | |
| B01D 53/18 | (2006.01) | |
| B01D 53/34 | (2006.01) | |
| B01D 53/48 | (2006.01) | |
| B01D 53/86 | (2006.01) | |
| B01D 53/96 | (2006.01) | |
| C02F 1/58 | (2006.01) | |
| C10G 47/00 | (2006.01) | |
| F28F 9/26 | (2006.01) | |
| C10G 65/00 | (2006.01) | |
| F01D 17/14 | (2006.01) | |
| F01K 3/18 | (2006.01) | |
| F01K 13/02 | (2006.01) | |
| H02K 7/18 | (2006.01) | |
| C10G 69/00 | (2006.01) | |
| F01K 25/06 | (2006.01) | |
| F01K 25/08 | (2006.01) | |
| F01K 27/02 | (2006.01) | |
| F01K 13/00 | (2006.01) | |
| C10G 45/00 | (2006.01) | |
| C10K 3/04 | (2006.01) | |
| F01K 27/00 | (2006.01) | |
| C02F 101/10 | (2006.01) | |
| C02F 101/16 | (2006.01) | |
| C02F 103/18 | (2006.01) | |
| C02F 103/36 | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C01B 3/34* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0227* (2013.01); *C01B 2203/0233* (2013.01); *C01B 2203/0283* (2013.01); *C01B 2203/043* (2013.01); *C01B 2203/127* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11); *Y02P 30/10* (2015.11)

(56) References Cited

U.S. PATENT DOCUMENTS

| | | |
|---|---|---|
| 4,291,232 A | 9/1981 | Cardone |
| 4,471,619 A | 9/1984 | Nolley, Jr. |
| 4,512,155 A | 4/1985 | Sheinbaum |
| 4,792,390 A | 12/1988 | Staggs |
| 4,962,238 A | 10/1990 | Wolfe |
| 5,007,240 A | 4/1991 | Ishida |
| 5,164,070 A | 11/1992 | Munro |
| 5,240,476 A | 8/1993 | Hegarty |
| 5,497,624 A | 3/1996 | Amir |
| 6,733,636 B1 | 5/2004 | Heins |
| 8,046,999 B2 | 11/2011 | Doty |
| 9,328,634 B2 | 5/2016 | Ikegami |
| 9,562,201 B2 | 2/2017 | Noureldin |
| 9,851,153 B2 | 12/2017 | Noureldin |
| 2002/0023538 A1 | 2/2002 | Agarwal |
| 2003/0092952 A1 | 5/2003 | Netzer |
| 2003/0132138 A1 | 7/2003 | Mehra |
| 2004/0186332 A1 | 9/2004 | Kong |
| 2006/0010872 A1 | 1/2006 | Singh |
| 2008/0128134 A1 | 6/2008 | Mudunuri |
| 2008/0174115 A1 | 7/2008 | Lambirth |
| 2008/0257413 A1 | 10/2008 | Noureldin et al. |
| 2008/0289588 A1 | 11/2008 | Wees et al. |
| 2008/0314726 A1 | 12/2008 | Choros |
| 2009/0000299 A1 | 1/2009 | Ast |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2011/0016863 A1 | 1/2011 | Ernst |
| 2011/0072819 A1 | 3/2011 | Silva |
| 2011/0072820 A1 | 3/2011 | Finkenrath |
| 2011/0083437 A1 | 4/2011 | Ast |
| 2011/0158858 A1 | 6/2011 | Alves |
| 2012/0031096 A1 | 2/2012 | Acikgoz et al. |
| 2012/0047889 A1 | 3/2012 | Acikgoz et al. |
| 2012/0048718 A1 | 3/2012 | Werba |
| 2012/0085096 A1 | 4/2012 | Penton et al. |
| 2012/0131921 A1 | 5/2012 | Held |
| 2012/0279728 A1 | 11/2012 | Northrop |
| 2012/0279900 A1 | 11/2012 | Noureldin et al. |
| 2012/0285169 A1 | 11/2012 | Freund |
| 2012/0298552 A1 | 11/2012 | Koseoglu |
| 2013/0104546 A1 | 5/2013 | Goswami |
| 2013/0145763 A1 | 6/2013 | Mirmobin et al. |
| 2013/0165534 A1 | 6/2013 | McComish |
| 2013/0213040 A1 | 8/2013 | Goswami |
| 2013/0231909 A1 | 9/2013 | Noureldin |

(56) References Cited

U.S. PATENT DOCUMENTS

| | | |
|---|---|---|
| 2013/0238154 A1 | 9/2013 | Noureldin |
| 2013/0334060 A1 | 12/2013 | Koseoglu et al. |
| 2014/0090405 A1 | 4/2014 | Held et al. |
| 2014/0142364 A1 | 5/2014 | Io |
| 2014/0260311 A1 | 9/2014 | Berlowitz |
| 2015/0377079 A1 | 12/2015 | Noureldin |
| 2016/0045841 A1 | 2/2016 | Kaplan |
| 2017/0058206 A1 | 3/2017 | Noureldin et al. |
| 2017/0082373 A1 | 3/2017 | Noureldin et al. |

FOREIGN PATENT DOCUMENTS

| | | |
|---|---|---|
| CN | 104560082 | 4/2015 |
| DE | 3731978 | 3/1988 |
| EP | 292391 | 11/1988 |
| EP | 949318 | 10/1999 |
| EP | 2516326 | 10/2012 |
| FR | 2990990 | 11/2013 |
| SU | 295317 | 10/1977 |
| WO | 97/21786 | 6/1997 |
| WO | 2004102082 | 11/2004 |
| WO | 2011090553 | 7/2011 |
| WO | 2012048132 | 4/2012 |
| WO | 2013055864 | 4/2013 |
| WO | 2014205163 | 12/2014 |

OTHER PUBLICATIONS

International Preliminary Report on Patentability in International Application No. PCT/US2016/048076, dated Mar. 8, 2018, 8 pages.
International Preliminary Report on Patentability in International Application No. PCT/US2016/048066, dated Mar. 8, 2018, 8 pages.
International Preliminary Report on Patentability in International Application No. PCT/US2016/048067, dated Mar. 8, 2018, 8 pages.
International Preliminary Report on Patentability in International Application No. PCT/US2016/048078, dated Mar. 8, 2018, 8 pages.
International Preliminary Report on Patentability in International Application No. PCT/US2016/048063, dated Mar. 8, 2018, 8 pages.
International Preliminary Report on Patentability in International Application No. PCT/US2016/048071, dated Mar. 8, 2018, 8 pages.
Communication Pursuant to Article 94(3) EPC issued in European Application No. 16758058.8 dated Dec. 11, 2018, 4 pages.
Feng Xu, D. Yogi Goswami and Sunil S. Bhagwat, "A combined power/cooling cycle," Energy, 25 (2000), 233-246.
D. Zheng, B. Chen, Y. Qi and H. Jin, "Thermodynamic analysis of a novel absorption power/cooling combined cycle," Applied Energy, 83 (2006), 311-323.
Meng Liu, and Na Zhang, "Proposal and analysis of a novel ammonia-water cycle for power and refrigeration cogeneration," Energy, 32 (2007), 961-970.
J.Wang, Y. Dai and L. Gao, "Parametric analysis and optimization for a combined power and refrigeration cycle," Applied Energy, 85 (2008), 1071-1085.
R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.
D. Ayou, J. C. Bruno, R. Saravanan and A. Coronas, "An Overview of Combined Absorption Power and Cooling Cycles," Renewable sustainable energy reviews, 21 (2013), 728-748.
J. Hua, Y. Chen, Y. Wang and A.P. Roskilly, "Thermodynamic analysis of ammonia-water power/chilling cogeneration cycle with low grade waste heat," Applied thermal engineering , 64 (2014), 483-490.
Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.
Stecco, "Kalina Cycles: Some Possible Applications and Comments," Proceedings of the American Power Conference, XP000609703, Jan. 1, 1993, vol. 1, pp. 196-201.
Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.
Sadrameli et al., "Optimum Operating Conditions for a Combined Power and Cooling Thermodynamic Cycle," Science Direct, Applied Energy, vol. 84, No. 3, Nov. 10, 2006, pp. 254-265.
Vidal, "Analysis of a Combined Power and Refrigeration Cycle by the Exergy Method," Science Direct, Energy 31, Dec. 1, 2006, pp. 3401-3414.
Schaschke, "A Dictionary of Chemical Engineering: Tatoray Process," Oxford, 2014, p. 371.
Marcilly, "Acido-Basic Catalysis: Applications to refining and Petrochemistry," IFP Publications, 2005, pp. 512-513.
Gary, "Petroleum Refining Technology and Economics: Figure 1.1 Refinery Flow Diagram," CRC Press, 5th ed., 2007, p. 3.
PCT International Search Report and Written Opinion of the International Searching Authority, PCT/US2016/027417, dated Jul. 6, 2016, 11 pages.
PCT International Search Report and Written Opinion of the International Searching Authority, PCT/US2016/027797, dated Oct. 19, 2016, 12 pages.
PCT International Search Report and Written Opinion of the International Searching Authority, PCT/US2016/027794, dated Oct. 19, 2016, 13 pages.
PCT International Search Report and Written Opinion of the International Searching Authority, PCT/US2016/030063, dated Oct. 19, 2016, 13 pages.
PCT International Search Report and Written Opinion of the International Searching Authority, PCT/US2016/030156, dated Oct. 19, 2016, 12 pages.
PCT International Search Report and Written Opinion of the International Searching Authority, PCT/US2016/048074, dated Nov. 9, 2016, 12 pages.
PCT International Search Report and Written Opinion of the International Searching Authority, PCT/US2016/048042, dated Nov. 9, 2016, 12 pages.
PCT International Search Report and Written Opinion of the International Searching Authority, PCT/US2016/048067, dated Nov. 15, 2016, 11 pages.
PCT International Search Report and Written Opinion of the International Searching Authority, PCT/US2016/048066, dated Nov. 15, 2016, 11 pages.
PCT International Search Report and Written Opinion of the International Searching Authority, PCT/US2016/048078, dated Nov. 15, 2016, 12 pages.
PCT International Search Report and Written Opinion of the International Searching Authority, PCT/US2016/048076, dated Nov. 15, 2016, 12 pages.
PCT International Search Report and Written Opinion of the International Searching Authority, PCT/US2016/048207, dated Nov. 21, 2016, 12 pages.
PCT International Search Report and Written Opinion of the International Searching Authority, PCT/US2016/048219, dated Nov. 21, 2016, 13 pages.
PCT International Search Report and Written Opinion of the International Searching Authority, PCT/US2016/048229, dated Nov. 21, 2016, 13 pages.
PCT International Search Report and Written Opinion of the International Searching Authority, PCT/US2016/048236, dated Nov. 21, 2016, 13 pages.
PCT International Search Report and Written Opinion of the International Searching Authority, PCT/US2016/027413, dated Nov. 22, 2016, 11 pages.
PCT International Search Report and Written Opinion of the International Searching Authority, PCT/US2016/048063, dated Nov. 23, 2016, 11 pages.
PCT International Search Report and Written Opinion of the International Searching Authority, PCT/US2016/048071, dated Nov. 23, 2016, 11 pages.
PCT International Search Report and Written Opinion of the International Searching Authority, PCT/US2016/048210, dated Dec. 22, 2016, 11 pages.

(56) References Cited

OTHER PUBLICATIONS

PCT International Search Report and Written Opinion of the International Searching Authority, PCT/US2016/048224, dated Dec. 22, 2016, 11 pages.
PCT International Search Report and Written Opinion of the International Searching Authority, PCT/US2016/048209, dated Dec. 22, 2016, 11 pages.
PCT International Search Report and Written Opinion of the International Searching Authority, PCT/US2016/048237, dated Dec. 22, 2016, 11 pages.
PCT International Search Report and Written Opinion of the International Searching Authority, PCT/US2016/048223, dated Dec. 22, 2016, 11 pages.
PCT International Search Report and Written Opinion of the International Searching Authority, PCT/US2016/048212, dated Dec. 22, 2016, 11 pages.
Communication Pursuant to Article 94(3) EPC issued in European Application No. 16758061.2 dated Dec. 18, 2018, 4 pages.
Gulf Cooperation Council Examination Report issued in GCC Application No. GC 2016-31904 on Nov. 13, 2018, 3 pages.
Gulf Cooperation Council Examination Report issued in GCC Application No. GC 2016-31907 on Nov. 13, 2018, 3 pages.
Gulf Cooperation Council Examination Report issued in GCC Application No. GC 2016-31906 on Nov. 13, 2018, 3 pages.
Gulf Cooperation Council Examination Report issued in GCC Application No. GC 2016-31908 on Nov. 13, 2018, 3 pages.
Gulf Cooperation Council Examination Report issued in GCC Application No. GC 2016-31901 on Nov. 13, 2018, 3 pages.
Gulf Cooperation Council Examination Report issued in GCC Application No. GC 2016-31905 on Nov. 13, 2018, 3 pages.
Gulf Cooperation Council Examination Report issued in GCC Application No. GC 2016-31902 on Nov. 13, 2018, 3 pages.
Gulf Cooperation Council Examination Report issued in GCC Application No. GC 2016-31903 on Nov. 13, 2018, 3 pages.

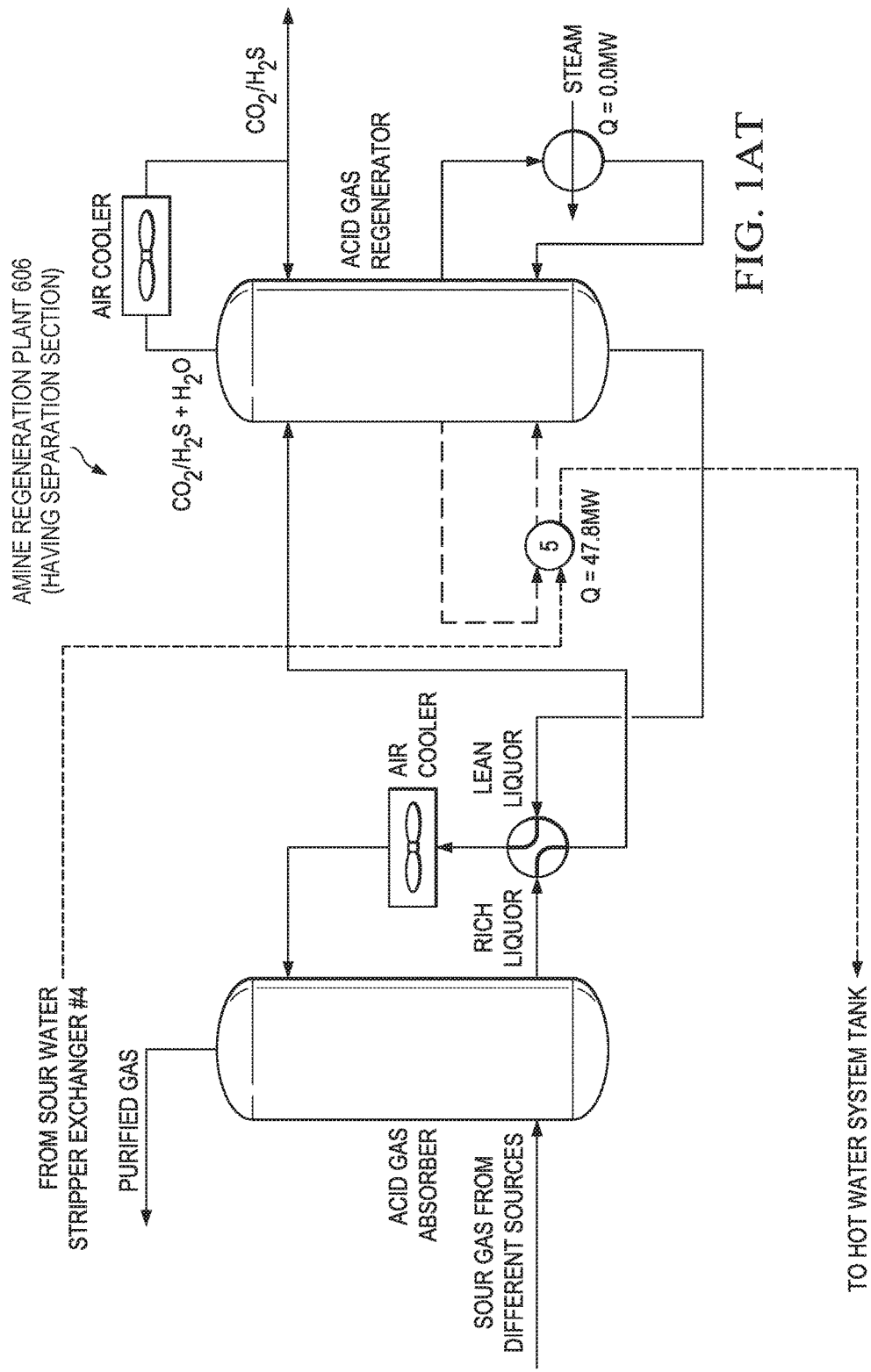

SYSTEMS FOR RECOVERY AND RE-USE OF WASTE ENERGY IN CRUDE OIL REFINING AND AROMATICS COMPLEX

CROSS-REFERENCE TO RELATED APPLICATIONS

This application is a continuation application of and claims the benefit of priority to U.S. patent application Ser. No. 15/242,186, filed on Aug. 19, 2016, which claims priority under 35 U.S.C. § 119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to inter-plants and hybrid, intra- and inter-plants direct or indirect waste heat recovery schemes for integrated refining-petrochemical facilities' thermal energy consumption reduction from waste energy in industrial facilities.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 1W-1AH illustrate a third set of configurations and related scheme details for thermally integrating different refining plants in the crude oil refining facility.

FIGS. 1AI-1AX illustrate a fourth set of configurations and related scheme details for thermally integrating different refining plants in the crude oil refining facility.

FIGS. 1AY-1BN illustrate a fifth set of configurations and related scheme details for thermally integrating different refining plants in the crude oil refining facility.

DETAILED DESCRIPTION

Figure 1A:
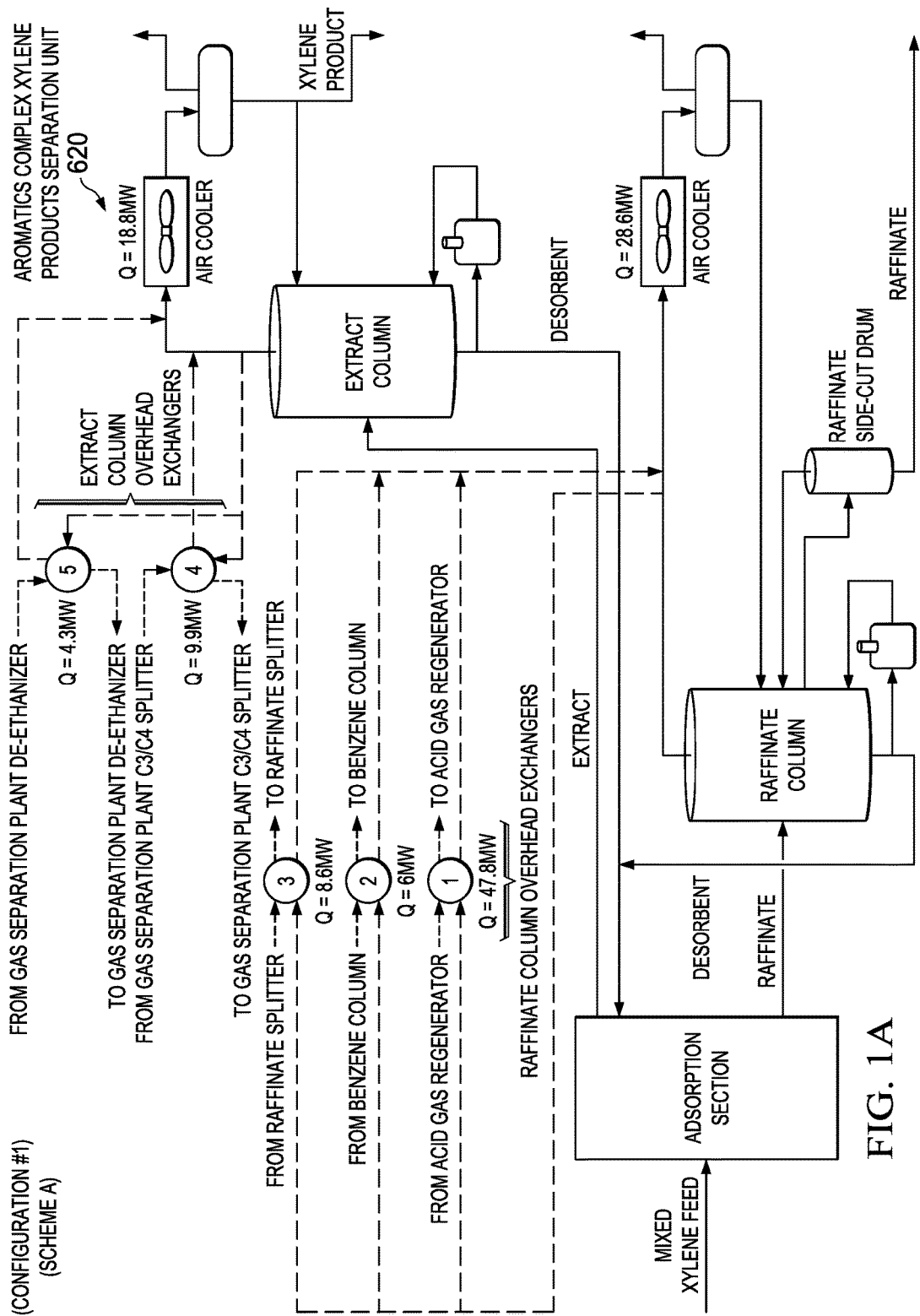
FIGS. 1A-1J illustrate a set of first configurations and related scheme details for thermally integrating different refining plants in the crude oil refining facility.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM British Thermal Units per hour (Btu/hr) can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydro-treating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3° C. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used in an acid gas absorber and regenerator to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatics content or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromatics feedstock is converted into lighter products under a wide range of high pressures and high temperatures in the presence of hydrogen and special catalysts. When the feedstock has a high paraffinic content, hydrogen prevents the formation of polycyclic aromatics compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydro-Treating Plant

Hydro-treating is a refinery process for reducing sulfur, nitrogen and aromatics while enhancing cetane number, density and smoke point. Hydro-treating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Recovery Plant

Sulfur recovery facilities in refineries operate to regulate the discharge of sulfur compounds to the atmosphere to meet environmental regulations. In a sulfur recovery plant, combustion products that include sulfur can be processed, for example, by heating, cooling with condensers, using sulfur conversion catalyst, and by other processing techniques. One technique is to use amines to extract the sulfur and other acid gas compounds.

9. Naphtha Hydro-Treating Plant and Continuous Catalytic Reformer Plants

A Naphtha Hydrotreater (NHT) produces 101 Research Octane Number (RON) reformate, with a maximum 4.0 psi (pounds per square inch) Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-byside. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, that is, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes new energy efficient configurations and the related specific intra- and inter-processing schemes for integrated medium grade semi-conversion crude oil refining and aromatics complex.

In some implementations, a semi-conversion medium grade crude oil refining facility includes an aromatics complex. This disclosure describes a waste heat recovery and reuse network for such a refining facility. As described later, waste heat can be recovered from multiple plants in the crude oil refining facility including one or more of the units in the aromatics plant. Such a refinery typically consumes several hundred megawatts of energy in heating utilities. Implementing the configurations described here can not only reduce energy consumption but also reduce energy-based greenhouse gas (GHG) emissions. In particular, this disclosure describes a method implemented in a crude oil refining facility to heat multiple first streams in multiple first plants of a crude oil refining facility using multiple second streams in multiple second plants in the crude oil refining facility. Several configurations of process schemes for doing so are described later with reference to the following figures.

Configuration 1

FIGS. 1A-1J illustrate configurations and related scheme details for thermally integrating different refining plants in the crude oil refining facility. The thermal integration described in these configurations and illustrated in FIGS. 1A-1J can reduce the crude oil refining facility's energy consumption (for example, heating and cooling utilities). For example, a reduction in energy consumption by about 77 MW (for example, 76.6 MW) can translate to at least about 12% (for example, 11.8%) of the energy consumption in the crude oil refining facility. In certain schemes, a process stream from one refining plant can be used to directly heat another process stream from another, different refining plant. In certain configurations, heat exchange between process streams can be implemented using an intermediate buffer fluid, for example, water, oil, or other buffer fluid.

Configuration 1—Scheme A

In some implementations, multiple first streams in the multiple first plants can be directly heated using a second stream from a second plant, and multiple third streams in the third plant can be directly heated using a fourth stream from the second plant. In some implementations, the multiple first plants in the crude oil refining facility can include an amine regeneration plant and an aromatics complex benzene extraction unit, and the multiple first streams can include a raffinate splitter bottoms, a benzene column bottoms and an acid gas regenerator bottoms streams. In some implementations, the second plant is an aromatics complex, which can include an aromatics complex xylene products separation unit, the second stream can include a raffinate column overheads stream, and the fourth stream can include an extract column overheads stream. In some implementations, the third plant can include the gas separation plant, and the third multiple streams can include the de-ethanizer bottoms and a C3/C4 splitter bottoms streams.

FIG. 1A shows an aromatics complex xylene products separation unit 620 in a crude oil refinery facility that includes a raffinate column overheads stream. The raffinate overheads column stream can be flowed in the plant as a single stream and split into multiple streams or it can be flowed into the plant as multiple streams to facilitate heat recovery. A first raffinate column overheads stream can directly heat an acid gas regenerator bottoms stream in a first heat exchanger with a thermal duty that can range between about 45 MW and 55 MW (for example, 47.8 MW). A second raffinate column overheads stream can directly heat a benzene column bottoms stream in a second heat exchanger with a thermal duty that can range between about 1 MW and 10 MW (for example, 6 MW). A third raffinate column overheads branch can directly heat a raffinate splitter column bottoms stream in a third heat exchanger with a thermal duty that can range between about 5 MW and 15 MW (for example, 8.6 MW). In this manner, the first heat exchanger, the second heat exchanger, and the third heat exchanger can be coupled to each other in parallel relative to the flow of raffinate column overheads. The parallel set of raffinate column overhead exchangers transfer heat directly to other process streams that would have otherwise been discharged to the environment. The raffinate column overheads streams are recombined and returned to the aromatics plant xylene products separation unit 620 for further processing.

The aromatics complex xylene products separation unit 620 also includes an extract column overheads stream. The extract column overheads stream can be flowed in the plant as a single stream and split into multiple streams or it can be flowed into the plant as multiple streams to facilitate heat recovery. A first extract column overheads stream can directly heat a C3/C4 splitter bottom stream in a fourth heat exchanger with a thermal duty that can range between about 5 MW and 15 MW (for example, 9.9 MW). A second extract column overhead branch can directly heat a de-ethanizer bottom stream in a fifth heat exchanger with a thermal duty that can range between about 1 MW and 10 MW (for example, 4.3 MW). In this manner, the fourth heat exchanger and the fifth heat exchanger can be coupled to each other in parallel relative to the flow of extract column overheads. The parallel set of extract column overhead exchangers transfer heat directly to other process streams that would have otherwise been discharged to the environment. The extract column overheads streams are recombined and returned to the aromatics plant xylene products separation unit 620 for further processing.

Figure 1B:
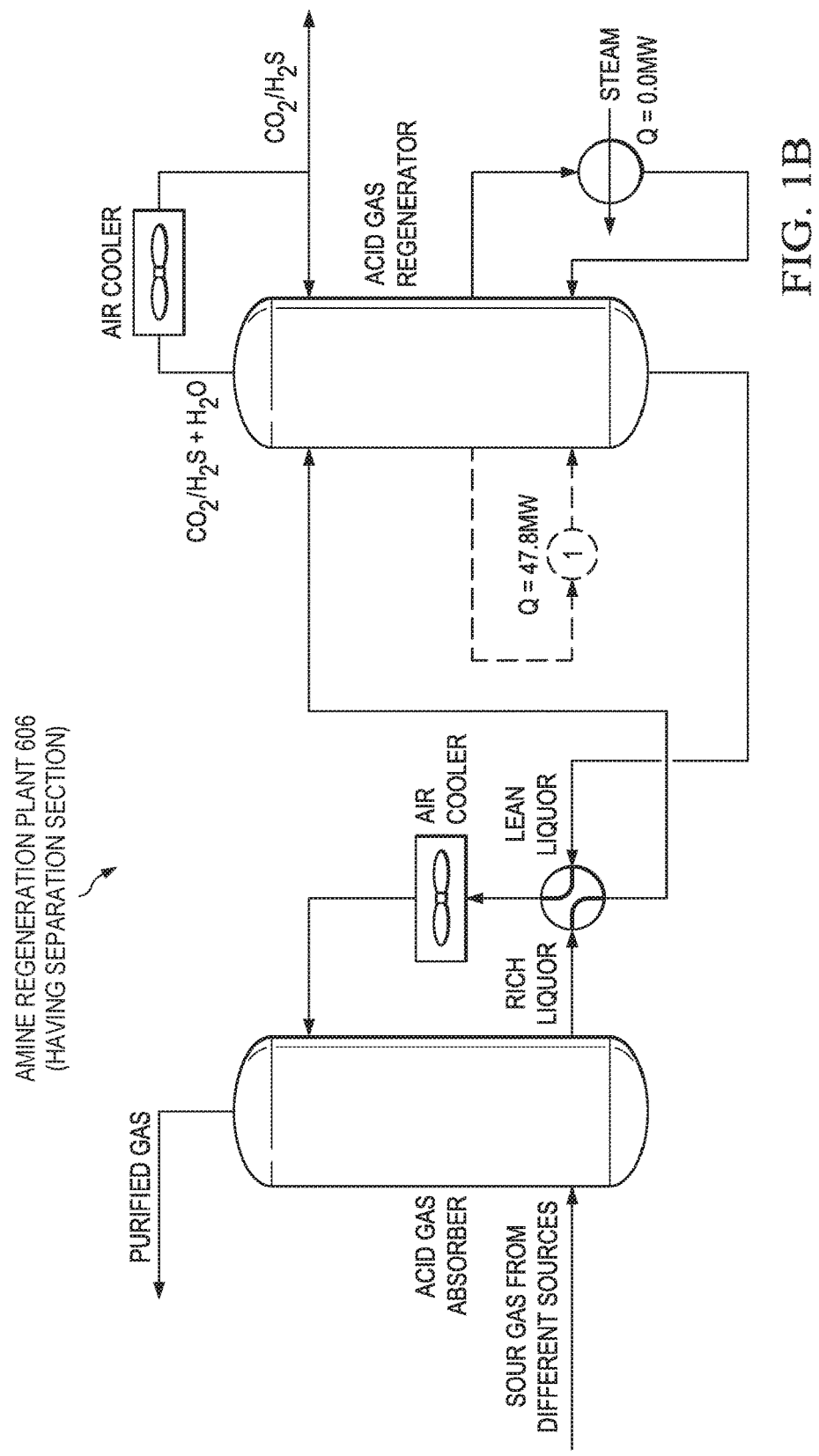

FIG. 1B shows the amine regeneration plant 606 in the crude oil refinery facility. The heated acid gas regenerator bottoms stream can then be flowed to the amine regeneration plant 606. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

Figure 1C:
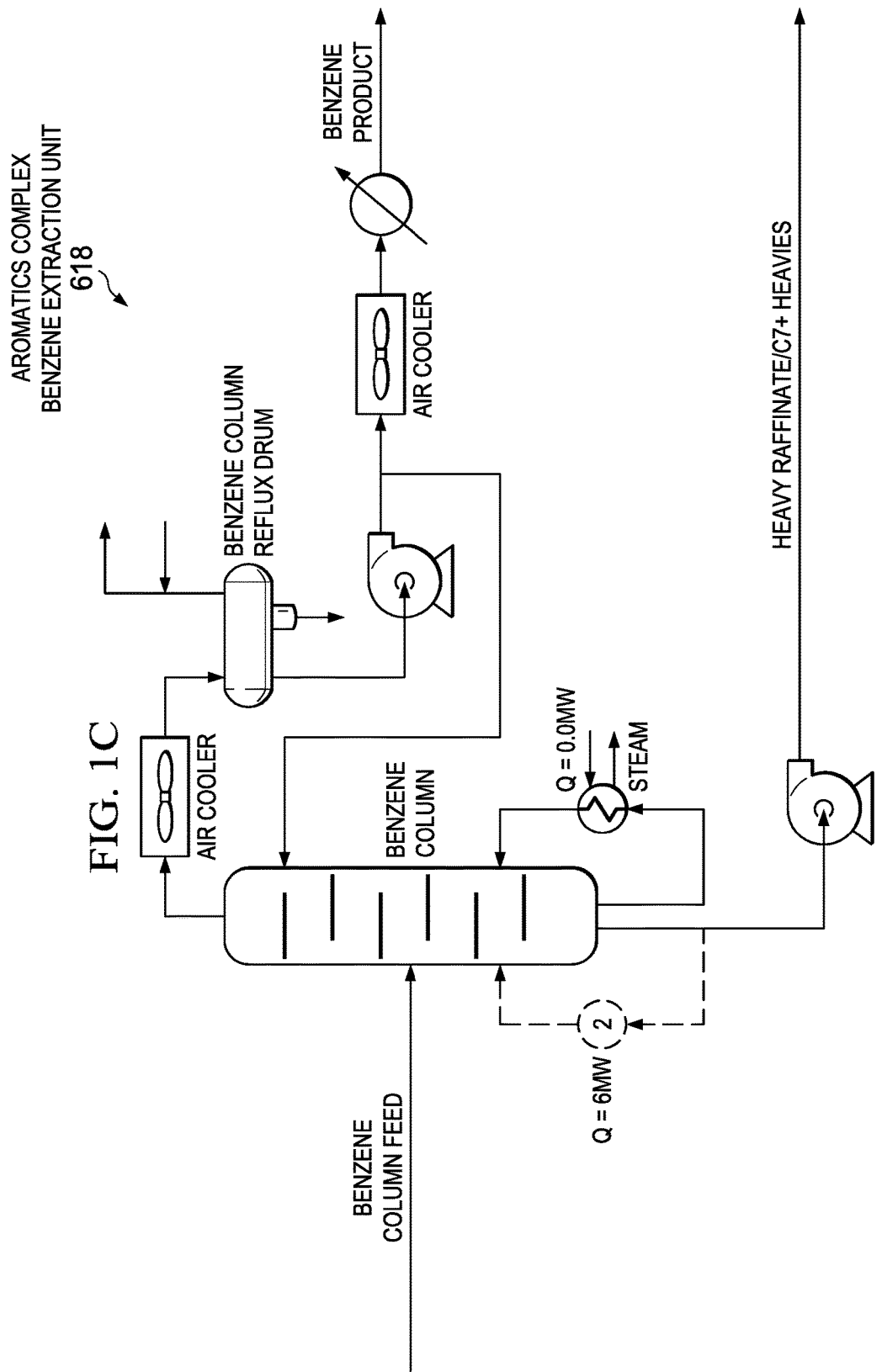

FIG. 1C shows the benzene extraction unit 618 in the crude oil refinery facility. The heated benzene column bottoms stream can be flowed to the benzene extraction plant 618 in the aromatics complex. As shown in FIG. 1C, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1D:
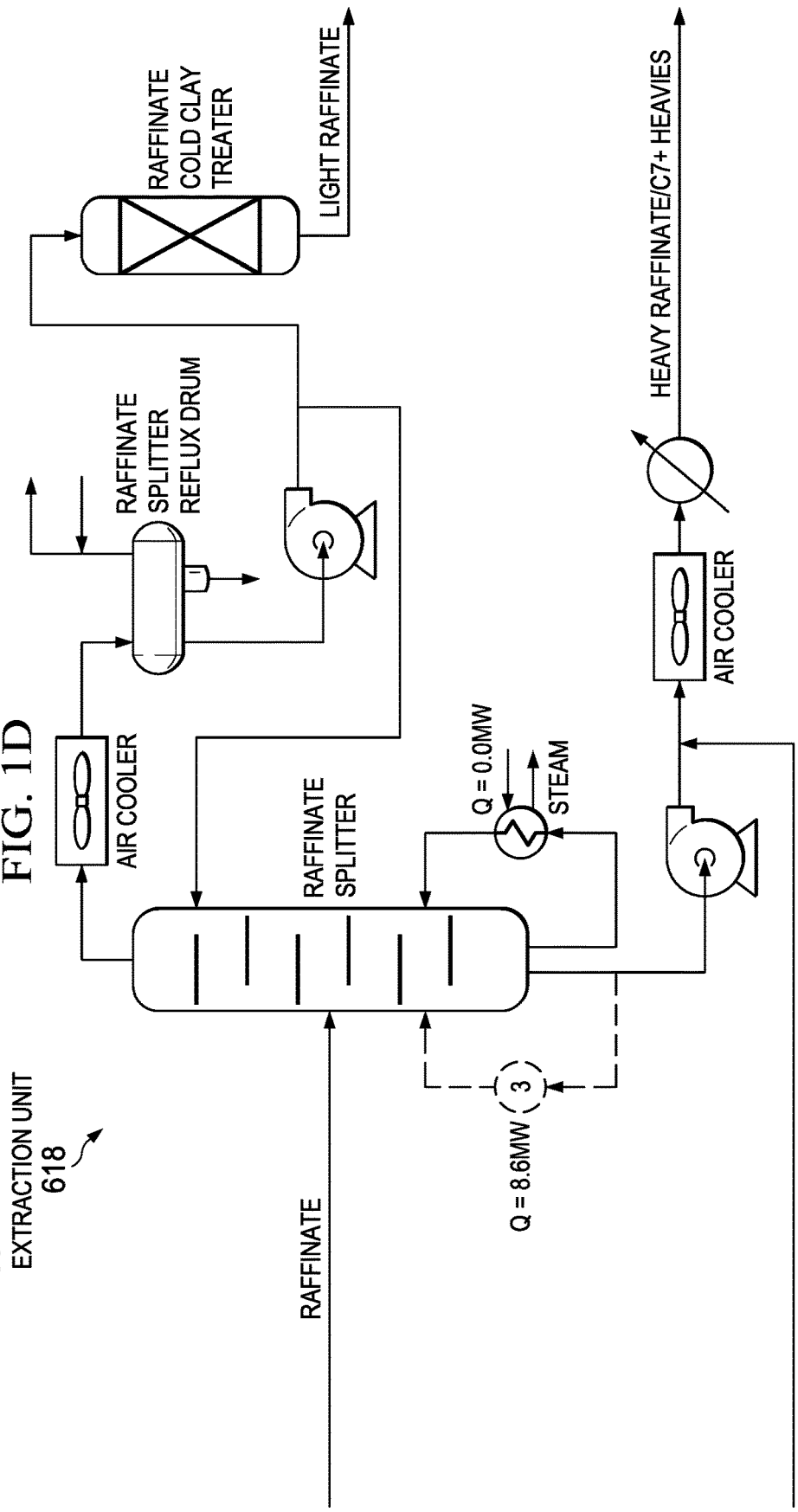

FIG. 1D shows another portion of the benzene extraction unit 618. The heated raffinate splitter column bottom stream can be flowed to the benzene extraction plant 618 in the aromatics complex. As shown in FIG. 1D, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Figure 1E:
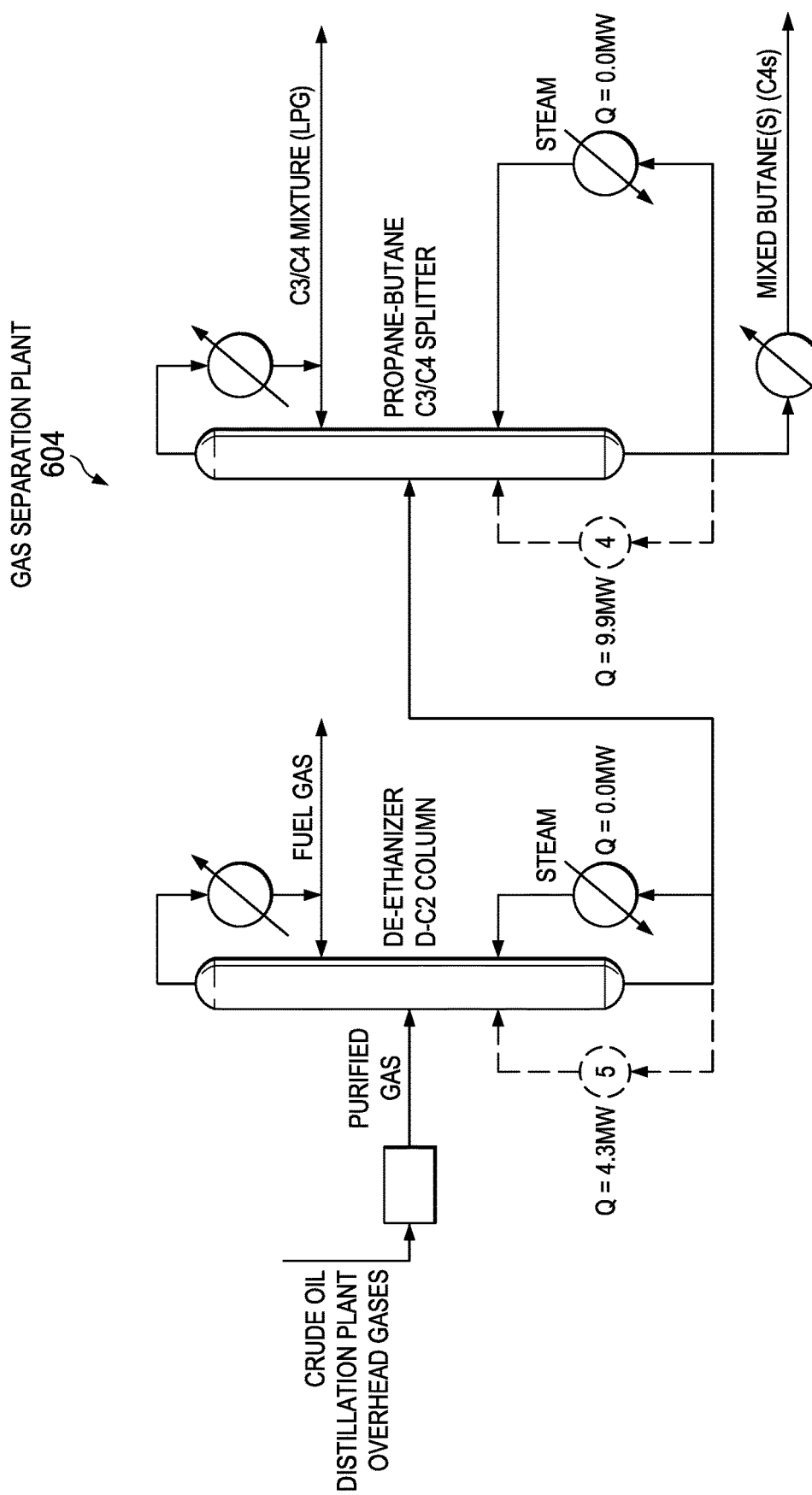

FIG. 1E shows the gas separation plant 604 in the crude oil refinery facility. The heated C3/C4 splitter bottoms stream can be flowed to the gas separation plant 604. As shown in FIG. 1E, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In addition, the heated de-ethanizer bottoms stream can also be flowed to the gas separation plant 604. As shown in FIG. 1E, in this configuration the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat directly from the aromatics complex can result in decreasing or eliminating the heat energy to heat the gas separation plant, the amine regeneration plant, the aromatics complex or a combination of them such as by about 77 MW.

Configuration 1—Scheme B

In some implementations, the multiple first streams in multiple first plants in the crude oil refining facility can be indirectly heated using a second stream in a second plant. In some implementations, the multiple first plants include the amine regeneration plant, the sulfur recovery plant, the aromatics complex benzene extraction unit, and the gas separation plant, and the multiple first streams include a raffinate splitter bottoms, a benzene column bottoms, an acid gas regenerator bottoms, a de-ethanizer bottoms and a C3/C4 splitter bottoms streams. The second plant is an aromatics complex, which can include an aromatics complex xylene products separation unit, and the second stream can include a raffinate column overheads stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 620. The buffer fluid can be flowed into the plant as a single stream and split into multiple streams or it can be flowed into the plant as multiple streams.

Figure 1F:
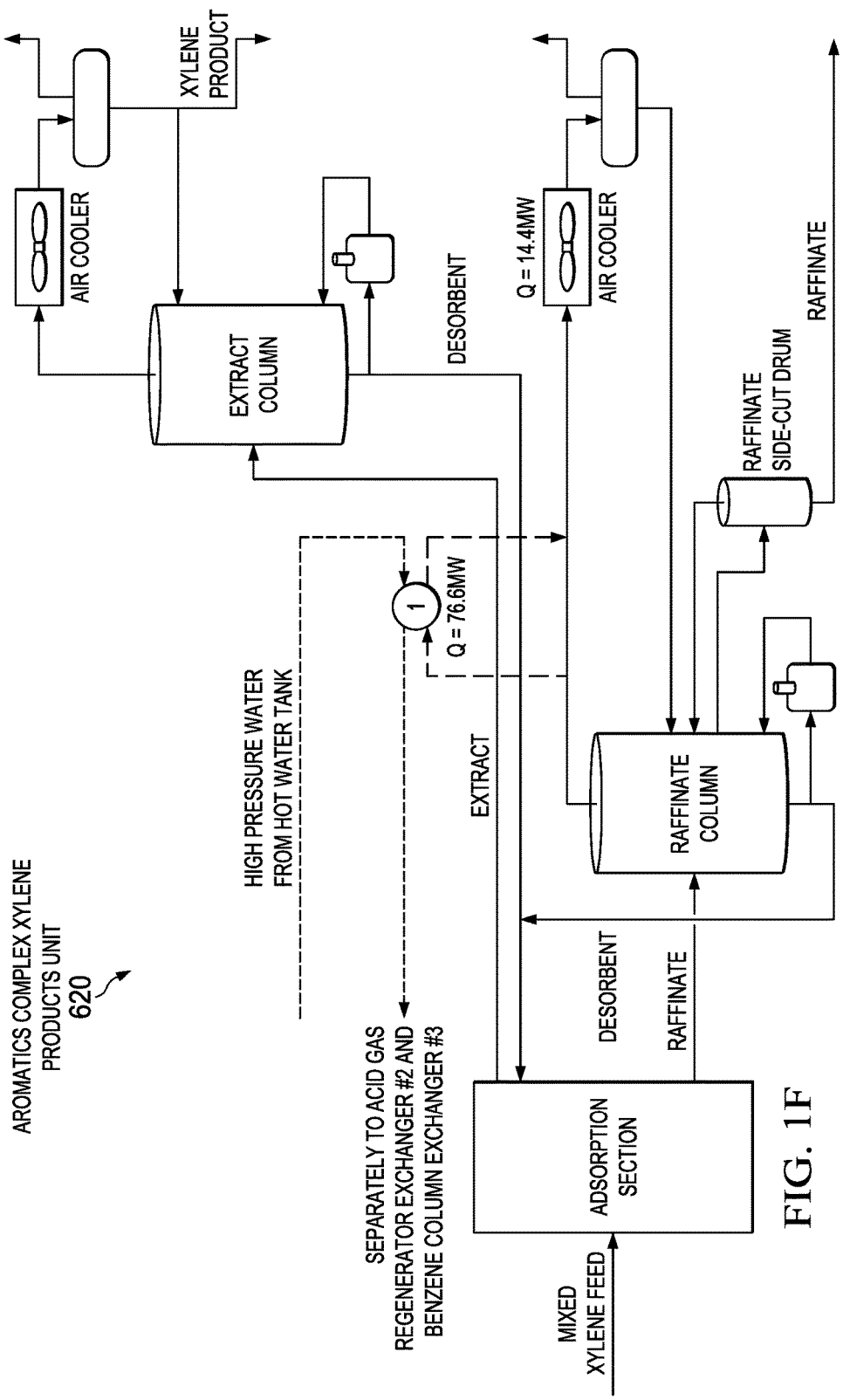

FIG. 1F shows an aromatics complex xylene products separation unit 620 in a crude oil refinery facility. A buffer fluid is flowed from a buffer fluid tank to the aromatics plant xylene products separation 620. The buffer fluid can be heated using an aromatics plant xylene products separation 620 raffinate column overhead stream in a first heat exchanger with a thermal duty that can range between about 70 MW and 80 MW (for example, 76.6 MW). The buffer fluid absorbs heat that would have otherwise been discharged to the environment. The raffinate column overheads stream is returned to the xylene products separation unit 620 for further processing.

The heated buffer fluid can be directed to a collection header (or in some embodiments, a heated or insulated buffer fluid tank or storage unit that can hold heated collected buffer fluid for a period before use) and then can be flowed to the amine regeneration plant 606, sulfur recovery plant 602, the aromatics complex benzene extraction unit 618, and the gas separation plant 604, and combinations thereof. In this instance, the heated buffer fluid is separated into a first heated buffer fluid stream and a second heated buffer fluid stream that are then maintained as separate heated buffer fluid streams.

Figure 1G:
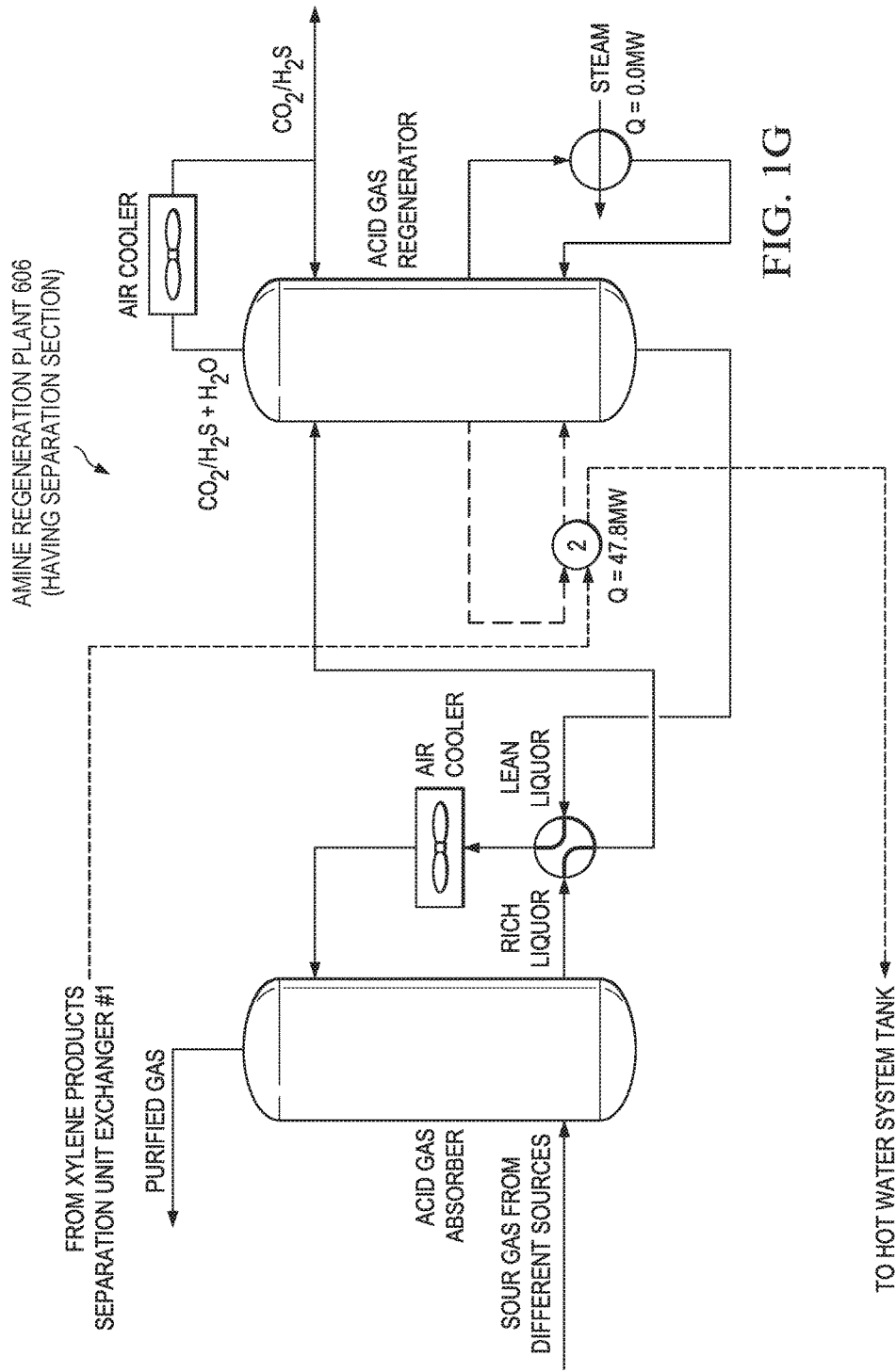

FIG. 1G shows the amine regeneration plant 606 in a crude oil refinery facility. The first heated buffer fluid stream is flowed to the amine regeneration plant 606. An acid gas regenerator bottoms stream is heated using the first heated buffer fluid stream in a second heat exchanger with a thermal duty that can range between about 45 MW and 55 MW (for example, 47.8 MW). The second heat exchanger is coupled to, in series with and is downstream of the first heat exchanger relative to the flow of the buffer fluid flow. As shown in FIG. 1G, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

Figure 1H:
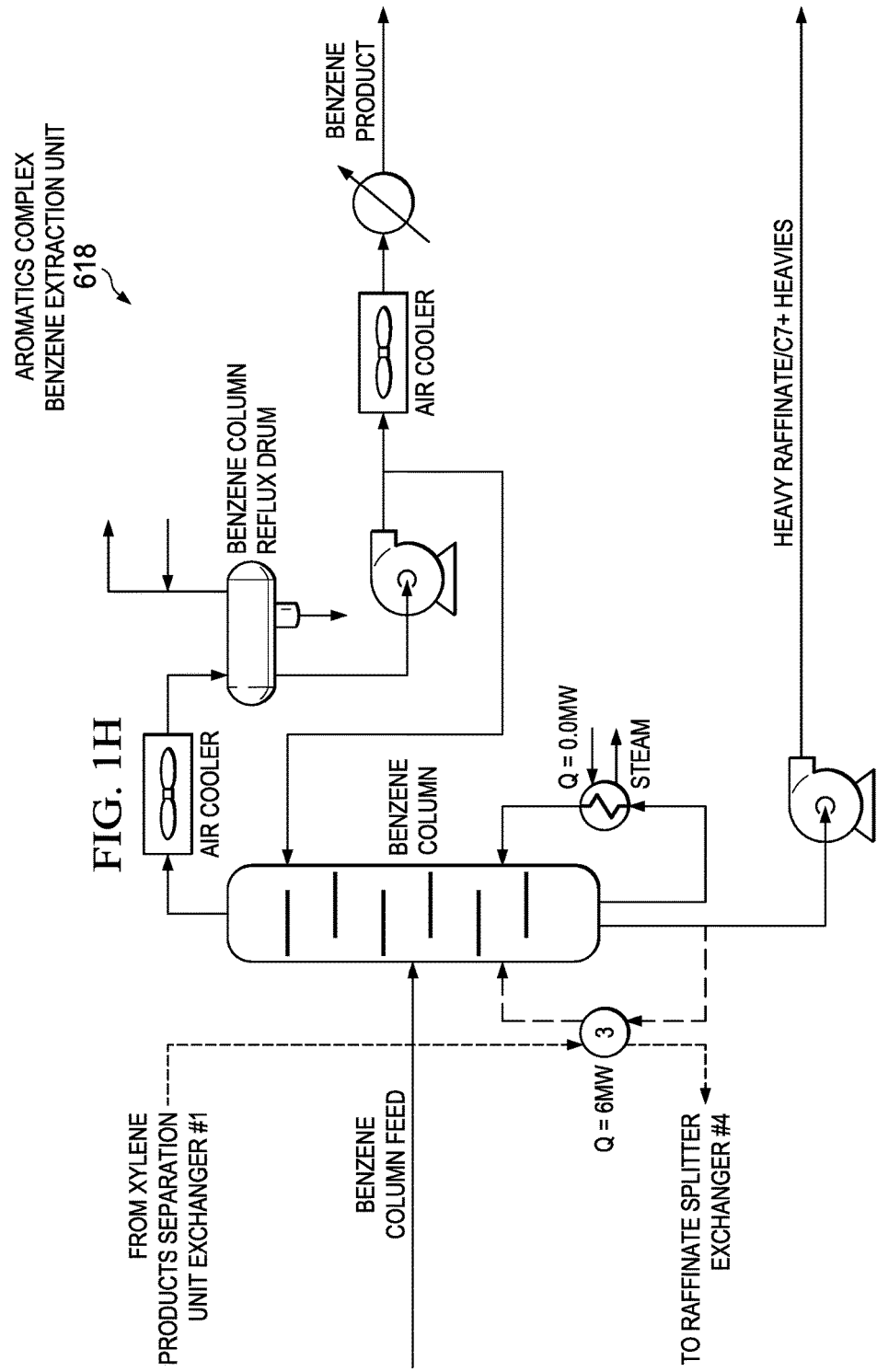

FIG. 1H shows the aromatics complex benzene extraction unit 618 in a crude oil refinery facility. The second heated buffer fluid stream is flowed to the aromatics complex benzene extraction unit 618. A benzene column bottoms stream is heated using the second heated buffer fluid stream in a third heat exchanger with a thermal duty that can range between about 1 MW and 10 MW (for example, 6 MW). The third heat exchanger is coupled to, in series with and is downstream of the first heat exchanger relative to the flow of buffer fluid. As shown in FIG. 1H, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1I:
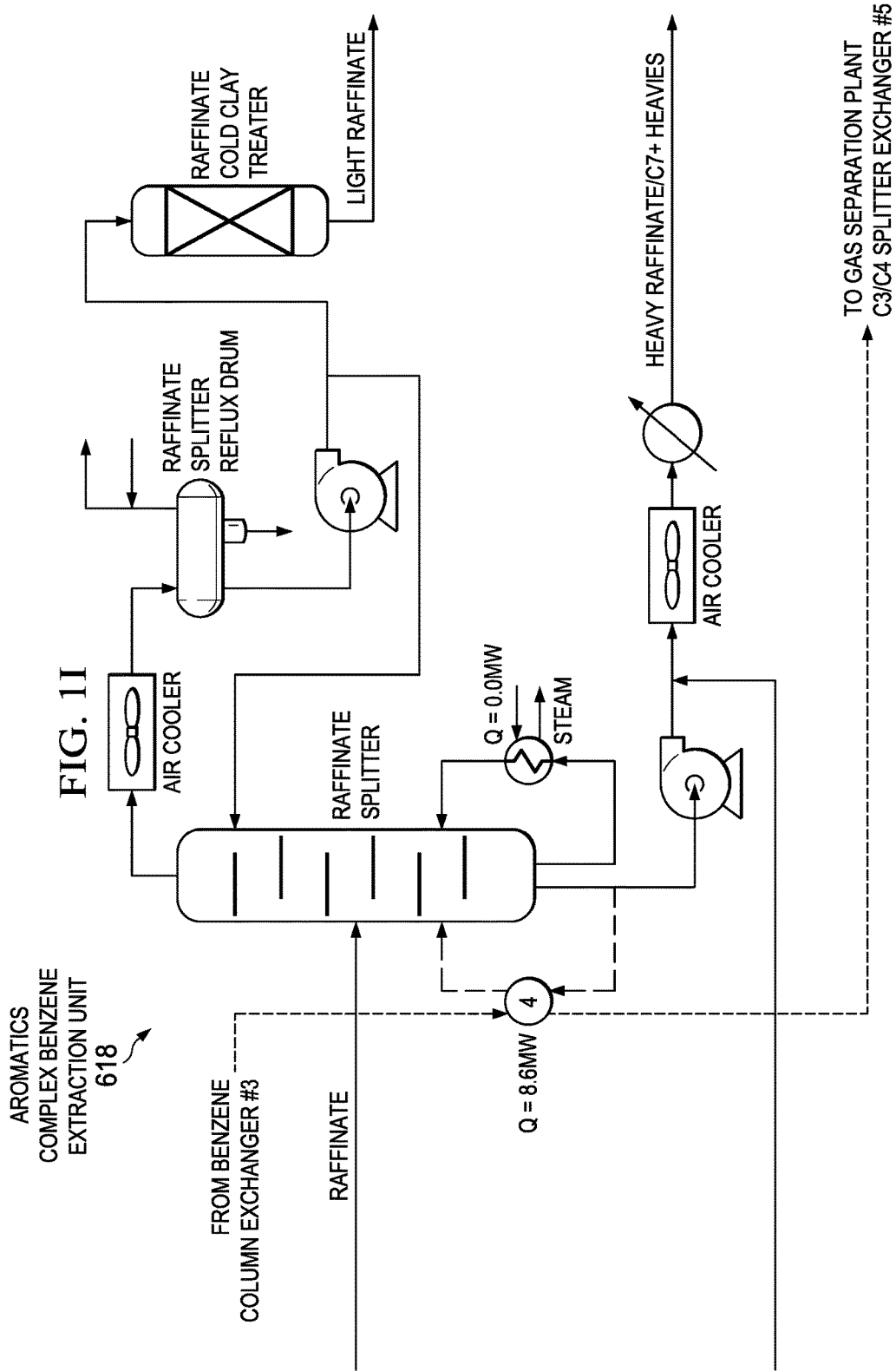

FIG. 1I also shows the aromatics complex benzene extraction unit 618. The second heated buffer fluid stream heats the raffinate splitter column bottoms stream in a fourth heat exchanger with a thermal duty that can range between about 5 MW and 15 MW (for example, 8.6 MW). The fourth heat exchanger is coupled to, in series with and is downstream of the first heat exchanger relative to the flow of the buffer fluid. As shown in FIG. 1I, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Figure 1J:
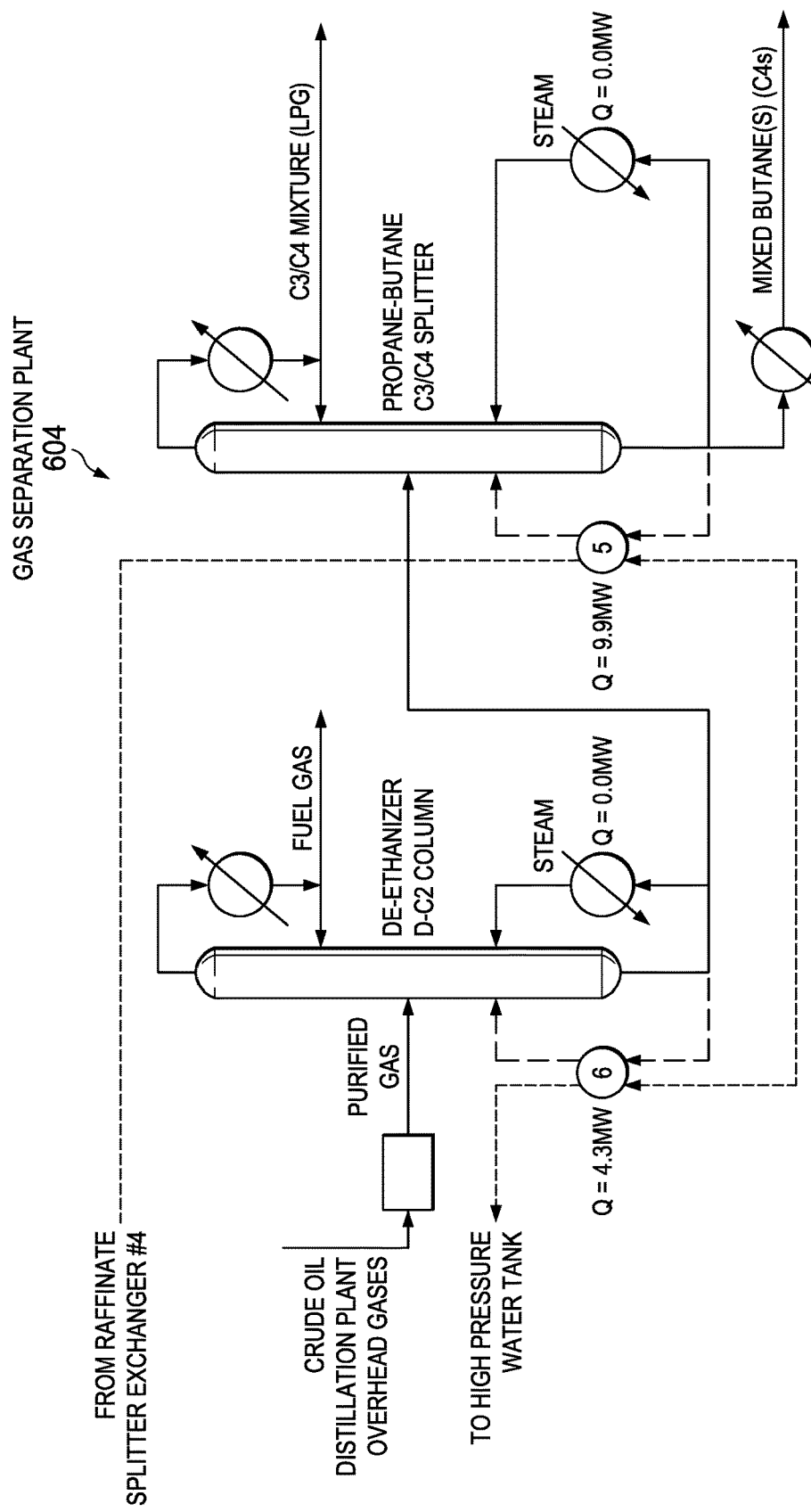

FIG. 1J shows the gas separation plant 604 in a crude oil refinery facility. The second heated buffer fluid stream is flowed to the gas separation plant 604. As shown in FIG. 1J, a C3/C4 splitter bottoms stream is heated using the second heated buffer fluid stream in a fifth heat exchanger with a thermal duty that can range between about 5 MW and 15 MW (for example, 9.9 MW). The fifth heat exchanger is coupled to, in series with and is downstream of the first heat exchanger relative to the buffer fluid flow. As shown in FIG. 1J, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

Also shown in FIG. 1J, the second heated buffer fluid stream heats the de-ethanizer bottoms stream in the sixth heat exchanger with a thermal duty that can range between about 1 MW and 10 MW (for example, 4.3 MW). The sixth heat exchanger is coupled to, in series with and is downstream of the first heat exchanger relative to the flow of the buffer fluid. As shown in FIG. 1J, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

The first heated buffer fluid stream exiting the second heat exchanger and the second heated buffer fluid stream exiting the sixth heat exchanger are flowed to the collection header or the buffer fluid tank for reuse. The third, fourth, fifth and sixth heat exchangers are coupled to one another in series relative to the flow of heated buffer fluid. In this manner, the second and the set of the third, fourth, fifth and sixth heat exchangers are coupled in parallel to one another relative to the flow of heated buffer fluid.

In some implementations, the heated buffer fluid can be flowed in series through the different plants. For example, the second heated buffer fluid can be flowed first to the gas separation plant then to any other first plant. As well, the order of heated buffer fluid intra-plant can be different, for example, the second heated buffer fluid can flow first through the de-ethanizer bottoms exchanger and then the C3/C4 splitter bottoms exchanger. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the aromatics complex xylene products separation unit can result in decreasing or eliminating the heat energy for heating the amine regeneration plant, the aromatics complex benzene extraction plant, the gas separation plant or combinations of them such as by about 77 MW.

Configuration 2

FIGS. 1K-1V illustrate configurations and related scheme details for thermally integrating different refining plants in the crude oil refining facility. The thermal integration described in these configurations and illustrated in FIGS. 1K-1V can reduce the crude oil refining facility's energy consumption (for example, heating and cooling utilities). For example, a reduction in energy consumption by about 82 MW (for example, 81.8 MW) can translate to at least about 13% (for example, about 12.6%) of the energy consumption in the crude oil refining facility. In certain schemes, a process stream from one refining plant can be used to directly heat another process stream from another, different refining plant. In certain configurations, heat exchange between process streams can be implemented using an intermediate buffer fluid, for example, water, oil, or other buffer fluid.

Configuration 2—Scheme A

In some implementations, the multiple first streams in multiple first plants in the crude oil refining facility can be directly heated using a second stream in a second plant, and multiple third streams in multiple third plants in the crude oil refining facility can be directly heated using a fourth stream in the second plant. In some implementations, the multiple first plants and the multiple third plants share a common plant. In some implementations, the multiple first plants can include a, an amine regeneration plant, a sulfur recovery plant, a sour water stripper plant and an aromatics complex benzene extraction unit, and the multiple first streams can include a benzene column bottoms, a sour water stripper bottoms and an amine regenerator bottoms streams. The second plant includes the aromatics complex, which can include an aromatics complex xylene products separation unit, the second stream can include a raffinate column overheads stream, and the fourth stream can include an extract column overheads stream. The multiple third plants can include the aromatics complex benzene extraction unit and the gas separation plant, and the multiple third streams include the de-ethanizer bottoms, a C3/C4 splitter bottoms streams and a raffinate splitter bottoms. In some instances, the shared common plant can be an aromatics complex benzene extraction unit.

Figure 1K:
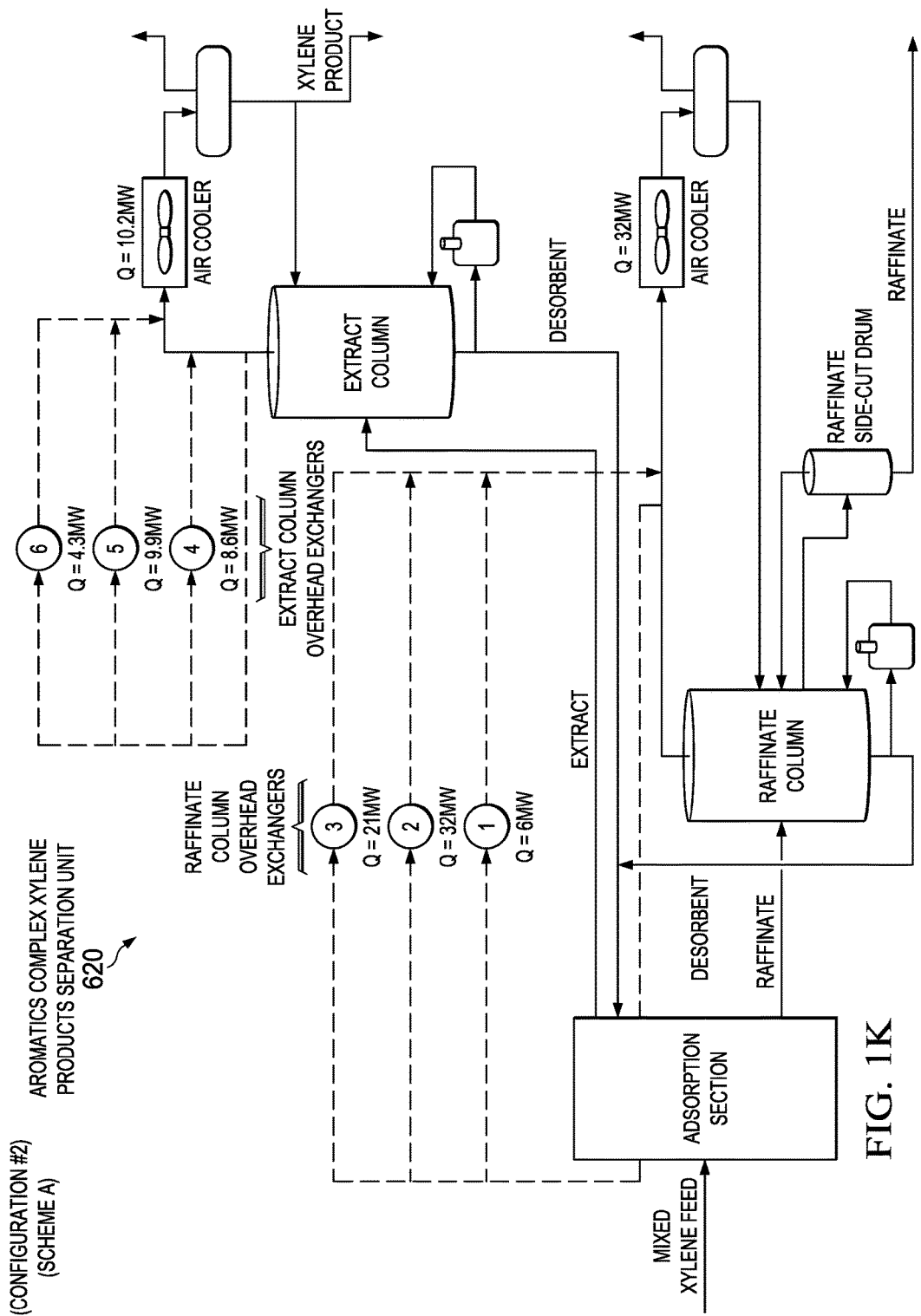
FIGS. 1K-1V illustrate a second set of configurations and related scheme details for thermally integrating different refining plants in the crude oil refining facility.

FIG. 1K shows an aromatics complex xylene products separation unit 620 in a crude oil refinery facility that includes a raffinate column overheads stream. The raffinate column overheads stream can be flowed in the plant as a single stream and split into multiple streams or it can be flowed into the plant as multiple streams to facilitate heat recovery. A first raffinate column overhead stream can directly heat a benzene column bottoms stream in a first heat exchanger with a thermal duty that can range between about 1 MW and 10 MW (for example, 6 MW). A second raffinate column overhead stream can directly heat a sour water stripper bottoms stream in a second heat exchanger with a thermal duty that can range between about 25 MW and 35 MW (for example, 32 MW). A third raffinate column overhead stream can directly heat an amine regenerator bottoms stream in a third heat exchanger with a thermal duty that can range between about 15 MW and 25 MW (for example, 21 MW). In this manner, the first heat exchanger, the second heat exchanger, and the third heat exchanger can be coupled to each other in parallel relative to the flow of raffinate column overheads. The parallel set of raffinate column overhead exchangers transfer heat directly to other process streams that would have otherwise been discharged to the environment. The raffinate column overheads streams are recombined and returned to the aromatics plant xylene products separation unit 620 for further processing.

The aromatics complex xylene products separation unit 620 also includes an extract column overheads stream. The extract column overheads stream can be flowed in the plant as a single stream and split into multiple streams or it can be flowed into the plant as multiple streams to facilitate heat recovery. A first extract column overhead stream can directly heat a raffinate splitter bottoms stream in a fourth heat exchanger with a thermal duty that can range between about 5 MW and 15 MW (for example, 8.6 MW). A second extract column overheads stream can directly heat a C3/C4 splitter bottoms stream in a fifth heat exchanger with a thermal duty that can range between about 5 MW and 15 MW (for example, 9.9 MW). A third extract column overhead stream can directly heat a de-ethanizer bottom stream in a sixth heat exchanger with a thermal duty that can range between about 1 MW and 10 MW (for example, 4.3 MW). In this manner, the fourth, the fifth and the sixth heat exchangers can be coupled to each other in parallel relative to the flow of extract column overhead. The parallel set of extract column overhead exchangers transfer heat directly to other process streams that would have otherwise been discharged to the environment. The extract column overheads stream are recombined and returned to the aromatics plant xylene products separation unit 620 for further processing.

Figure 1L:
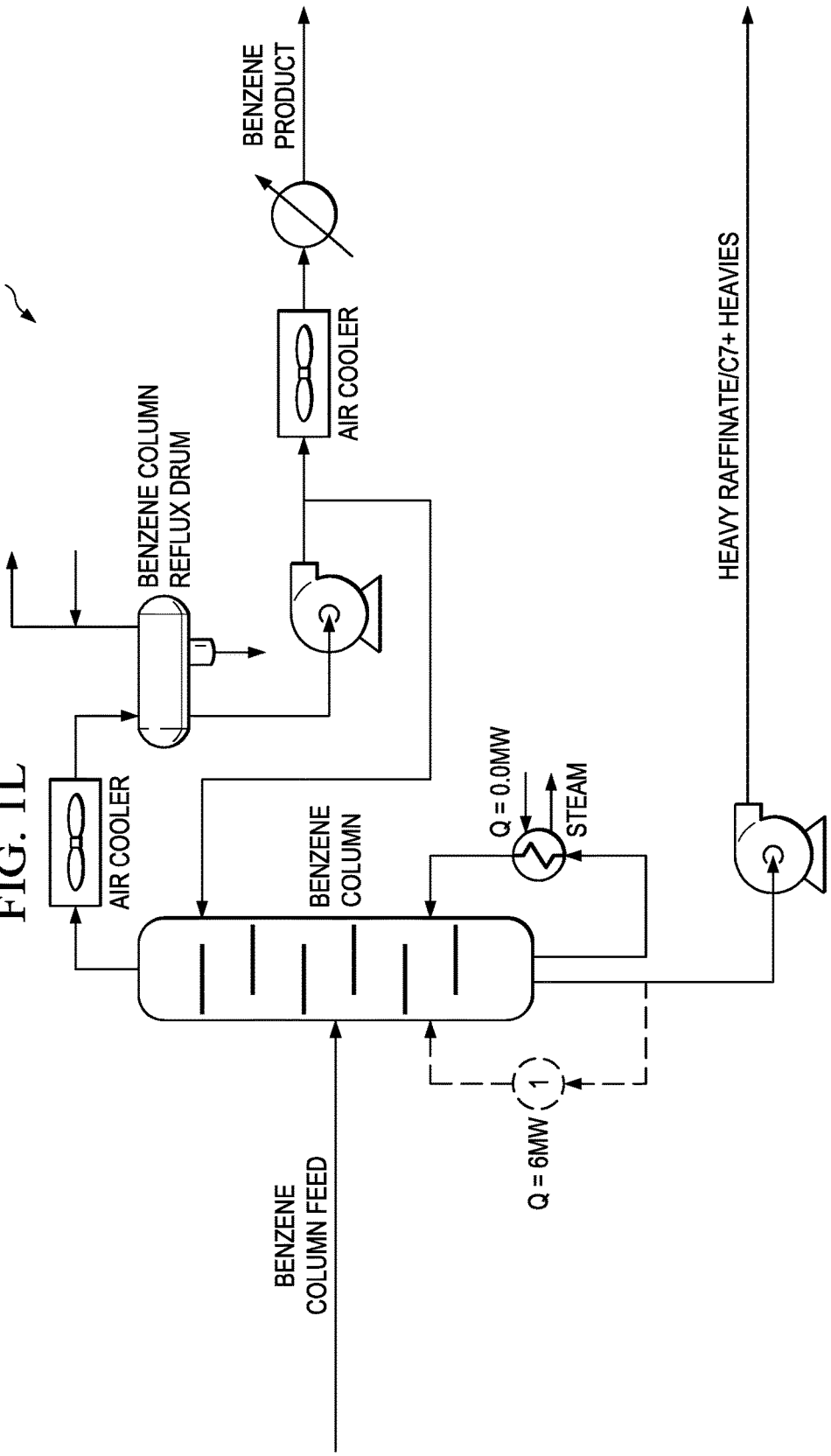

FIG. 1L shows the aromatics complex benzene extraction unit 618 in the crude oil refinery facility. The heated benzene column bottoms stream can be flowed to the benzene extraction plant 618. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1M:
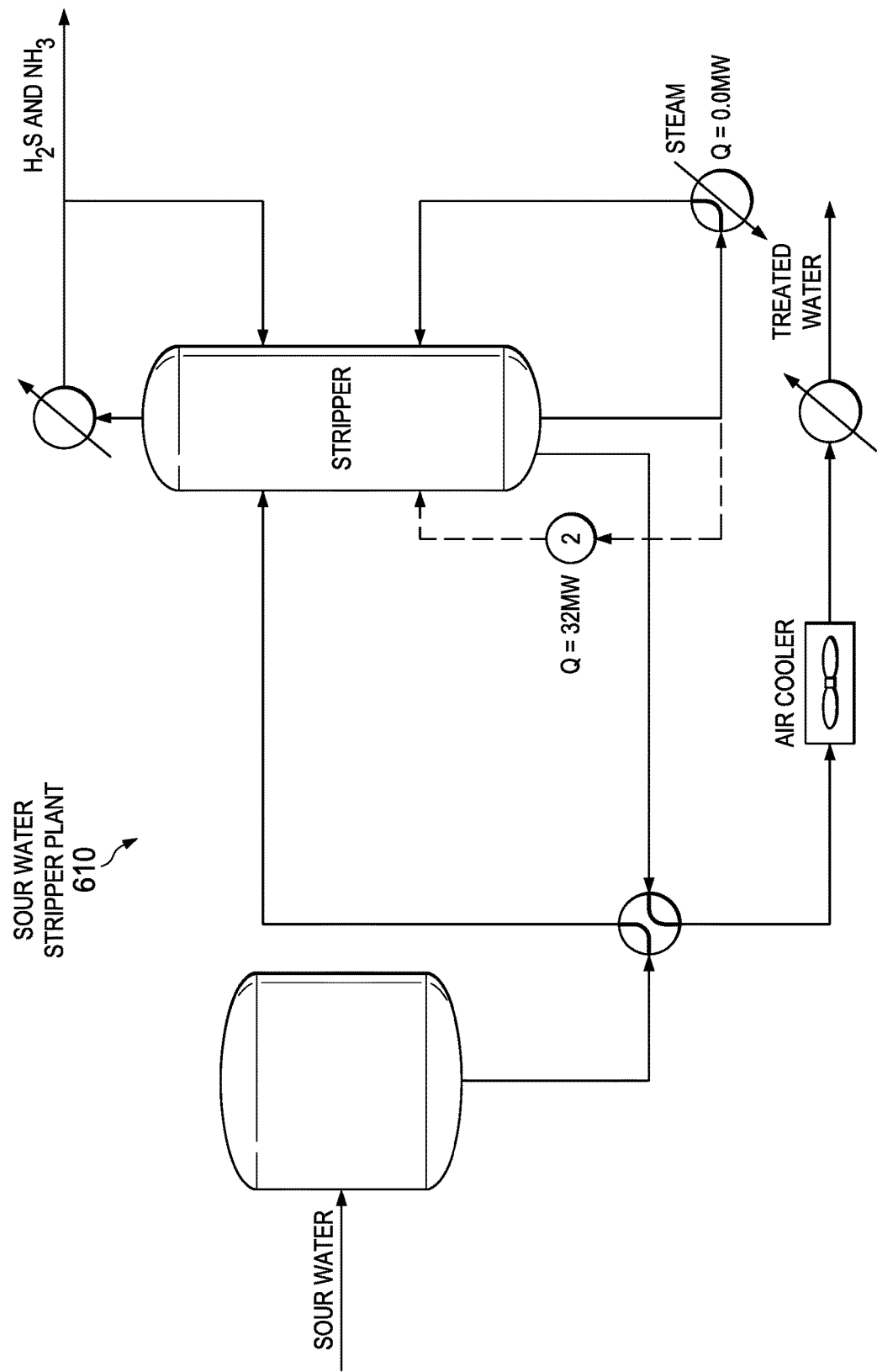
Figure 1N:
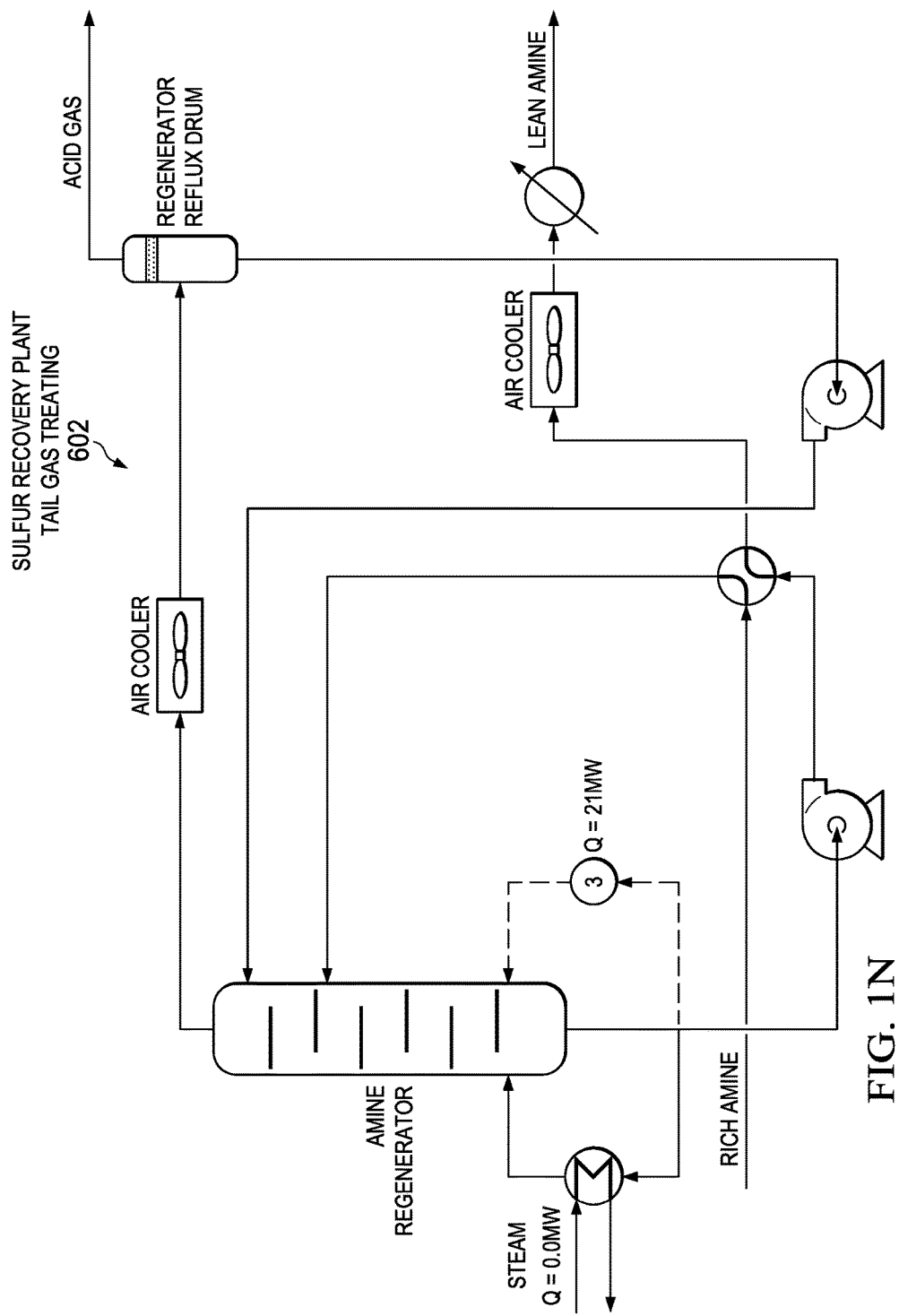
Figure 1O:
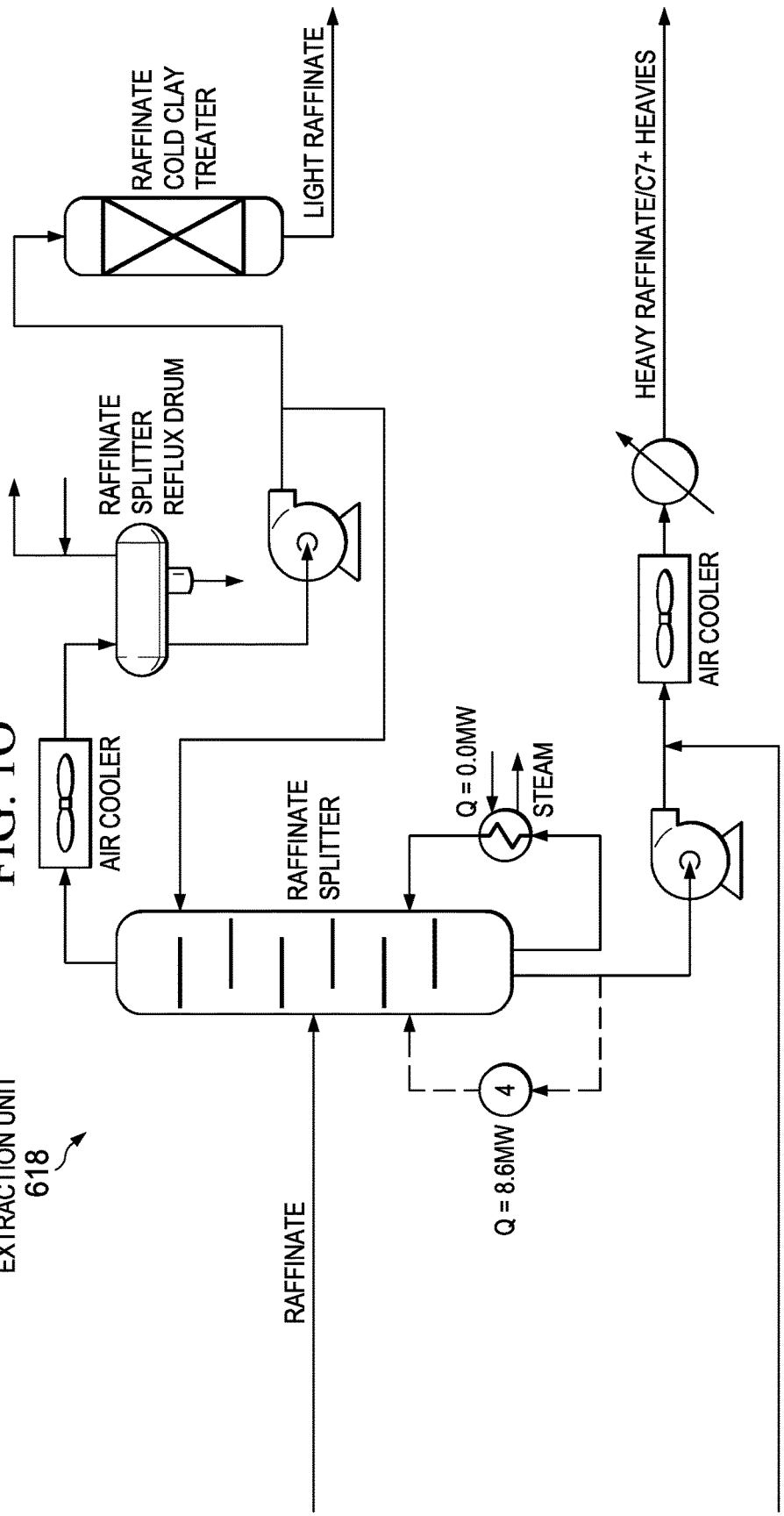

FIG. 1O also shows the aromatics complex benzene extraction unit 618. The heated raffinate splitter column bottoms stream can be flowed to the benzene extraction plant 618. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

FIG. 1M shows the sour water stripper 610 in the crude oil refinery facility. The heated sour water stripper stream can be flowed to the sour water stripper plant 610. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1N shows the sulfur recovery plant 602 in the crude oil refinery facility. The heated amine regenerator bottoms stream can then be flowed to the sulfur recovery plant 602. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Figure 1P:
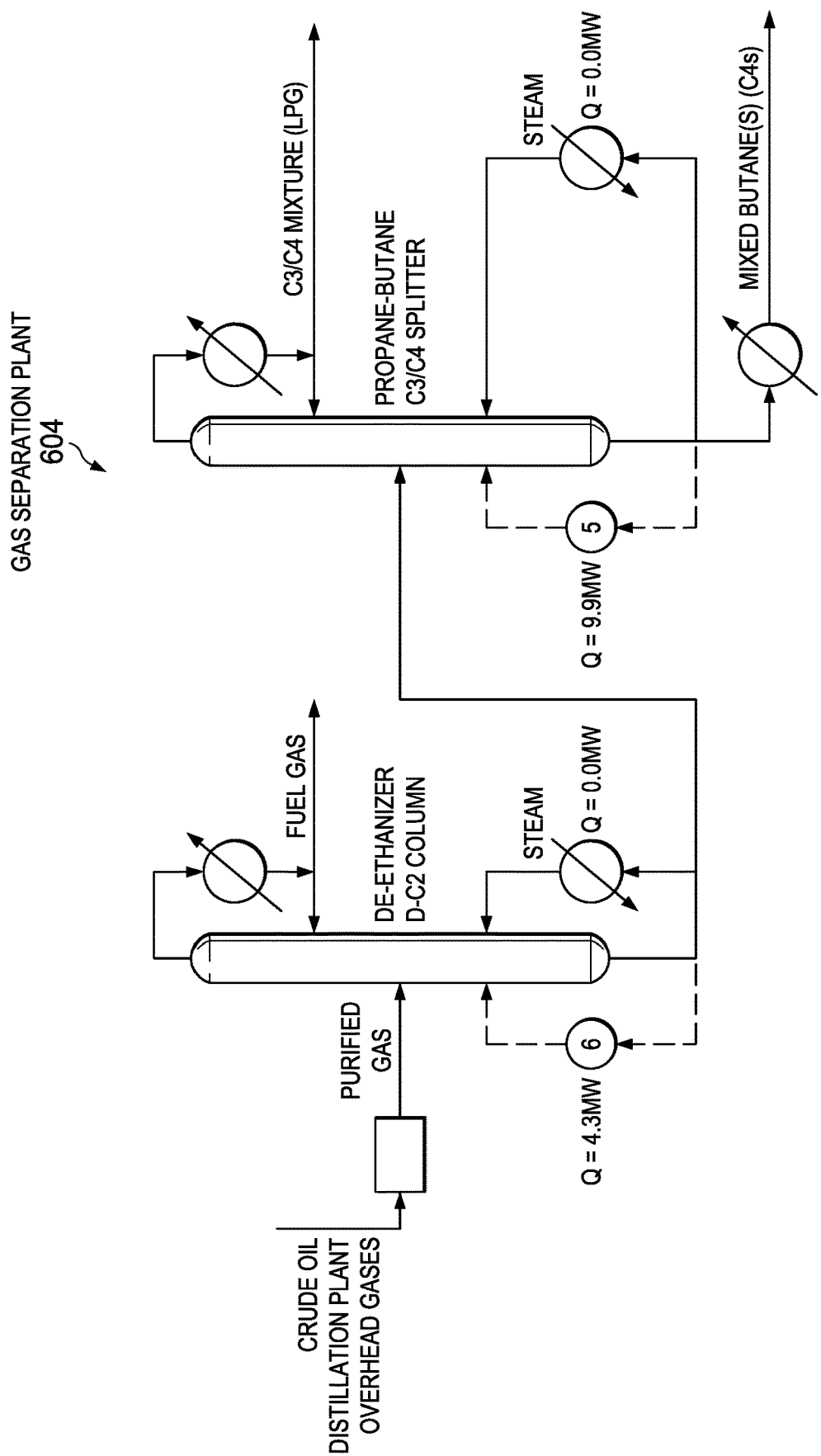

FIG. 1P shows the gas separation plant 604 in the crude oil refinery facility. The heated C3/C4 splitter bottoms stream can be flowed to the gas separation plant 604. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In addition, the heated de-ethanizer bottoms stream can also be flowed to the gas separation plant 604. As shown in FIG. 1P, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat can directly from the aromatics complex result in decreasing or eliminating the heat energy to heat the gas separation plant, an amine regeneration plant, a sulfur recovery plant, a sour water stripper plant, the aromatics complex or a combinations of them such as by about 82 MW.

Configuration 2—Scheme B

In some implementations, the multiple first streams in multiple first plants in the crude oil refining facility can be indirectly heated using a second stream in a second plant. In some implementations, the multiple first plants include the aromatics complex benzene extraction unit, the sour water stripper plant, the sulfur recovery plant, and the gas separation plant and the multiple first streams include a benzene column bottoms, a sour water stripper bottoms, an amine regenerator bottoms, a raffinate splitter bottoms, a de-ethanizer bottoms and a C3/C4 splitter bottoms streams. The second plant is an aromatics complex, which can include an aromatics complex xylene products separation unit, and the second stream can include a raffinate column overheads stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 620. The buffer fluid can be flowed into the plant as a single stream and split into multiple streams or it can be flowed into the plant as multiple streams.

Figure 1Q:
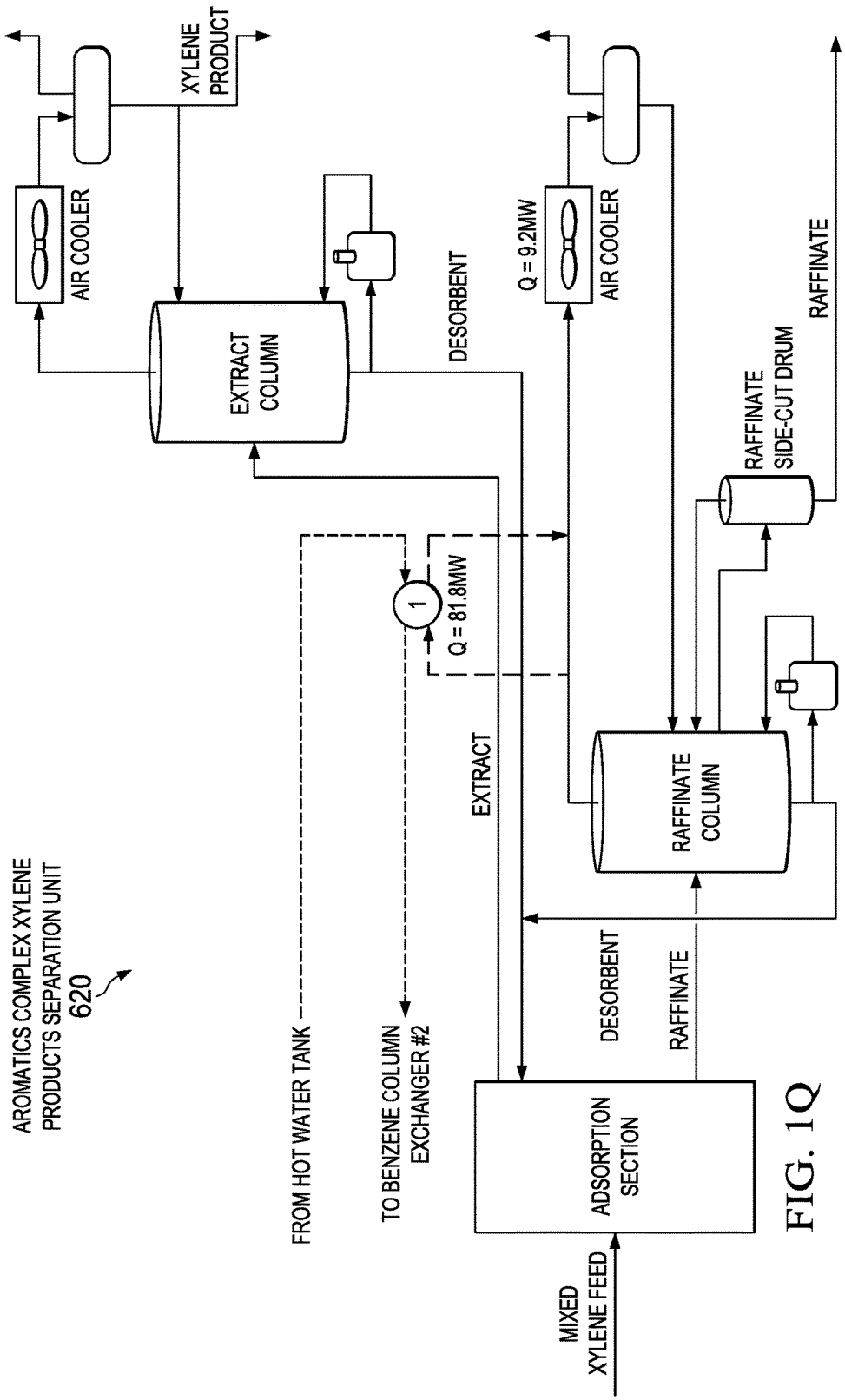

FIG. 1Q shows an aromatics complex xylene products separation unit 620 in a crude oil refinery facility. A buffer fluid can be flowed from a buffer tank to an aromatics plant xylene products separation unit 620. The buffer fluid can be heated using a raffinate column overhead stream in a first heat exchanger with a thermal duty that can range between about 75 MW and 85 MW (for example, 81.8 MW). The buffer fluid absorbs heat that would have otherwise been discharged to the environment. In an alternative embodiment, the cooling requirement of the raffinate column overheads stream can be 0 MW because the alternative flow path disclosed in this configuration may satisfy the entire cooling requirement for the raffinate column overheads stream for the operation of the raffinate column. The raffinate column overheads stream is returned to the xylene products separation unit 620 for further processing.

The heated buffer fluid is directed to a collection header (or in some embodiments, a heated or insulated buffer fluid tank or storage unit that can hold heated collected buffer fluid for a period before use) and then can be flowed to the sour water stripper plant 610, sulfur recovery plant 602, the aromatics complex benzene extraction unit 618, and the gas separation plant 604, and combinations thereof. In this instance, the heated buffer fluid is directed to the aromatics complex benzene extraction unit 618.

Figure 1R:
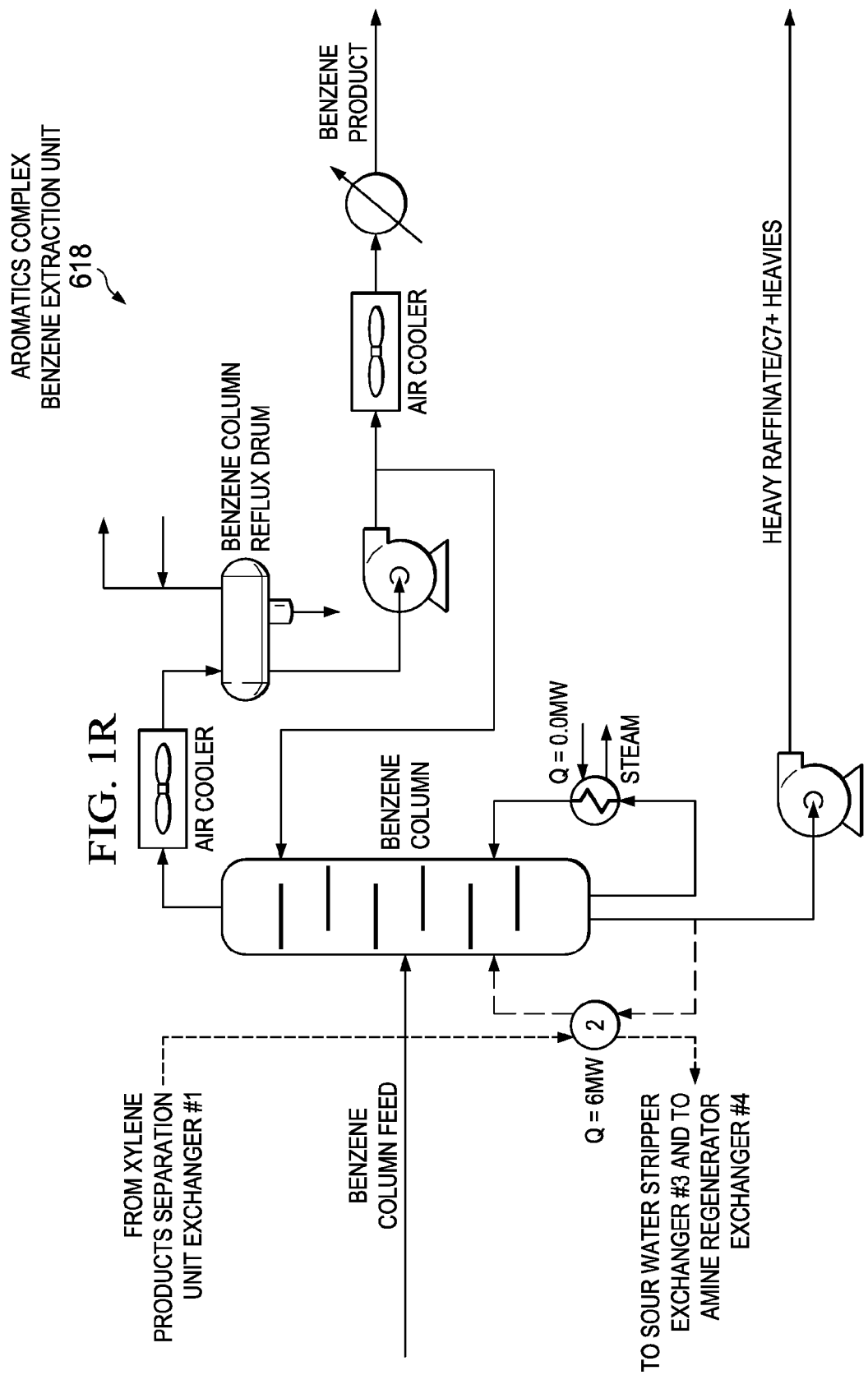

FIG. 1R shows the aromatics complex benzene extraction unit 618 in a crude oil refinery facility. The heated buffer fluid is flowed to the benzene extraction unit 618. A benzene column bottoms stream is heated using the heated buffer fluid in a second heat exchanger with a thermal duty that can range between about 1 MW and 10 MW (for example, 6 MW). The second heat exchanger is coupled to, in series with and is downstream of the first heat exchanger relative to the buffer fluid flow. As shown in FIG. 1R, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Figure 1S:
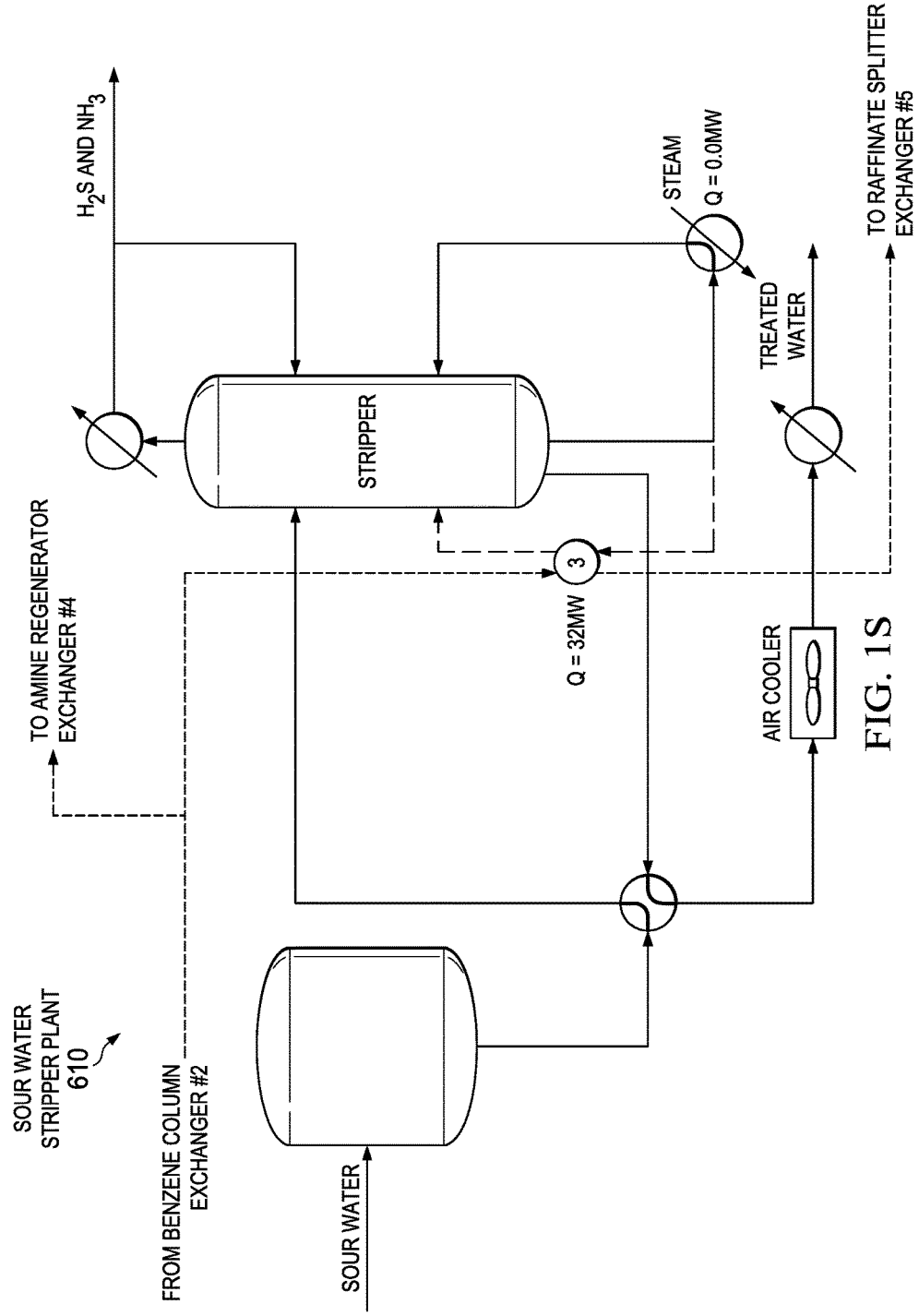

FIG. 1S shows the sour water stripper plant 610 in a crude oil refinery facility. The heated buffer fluid exiting the second heat exchanger is split into a first heated buffer fluid stream and a second heated buffer fluid stream to facilitate heat distribution. As shown in FIG. 1S, a first heated buffer fluid stream is flowed to the sour water stripper plant 610. A sour water stripper bottoms stream is heated using the first heated buffer fluid stream in a third heat exchanger with a thermal duty that can range between about 25 MW and 35 MW (for example, 32 MW). The third heat exchanger is coupled to, in series with and is downstream of the first heat exchanger relative to the buffer fluid flow. As shown in FIG. 1S, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1T:
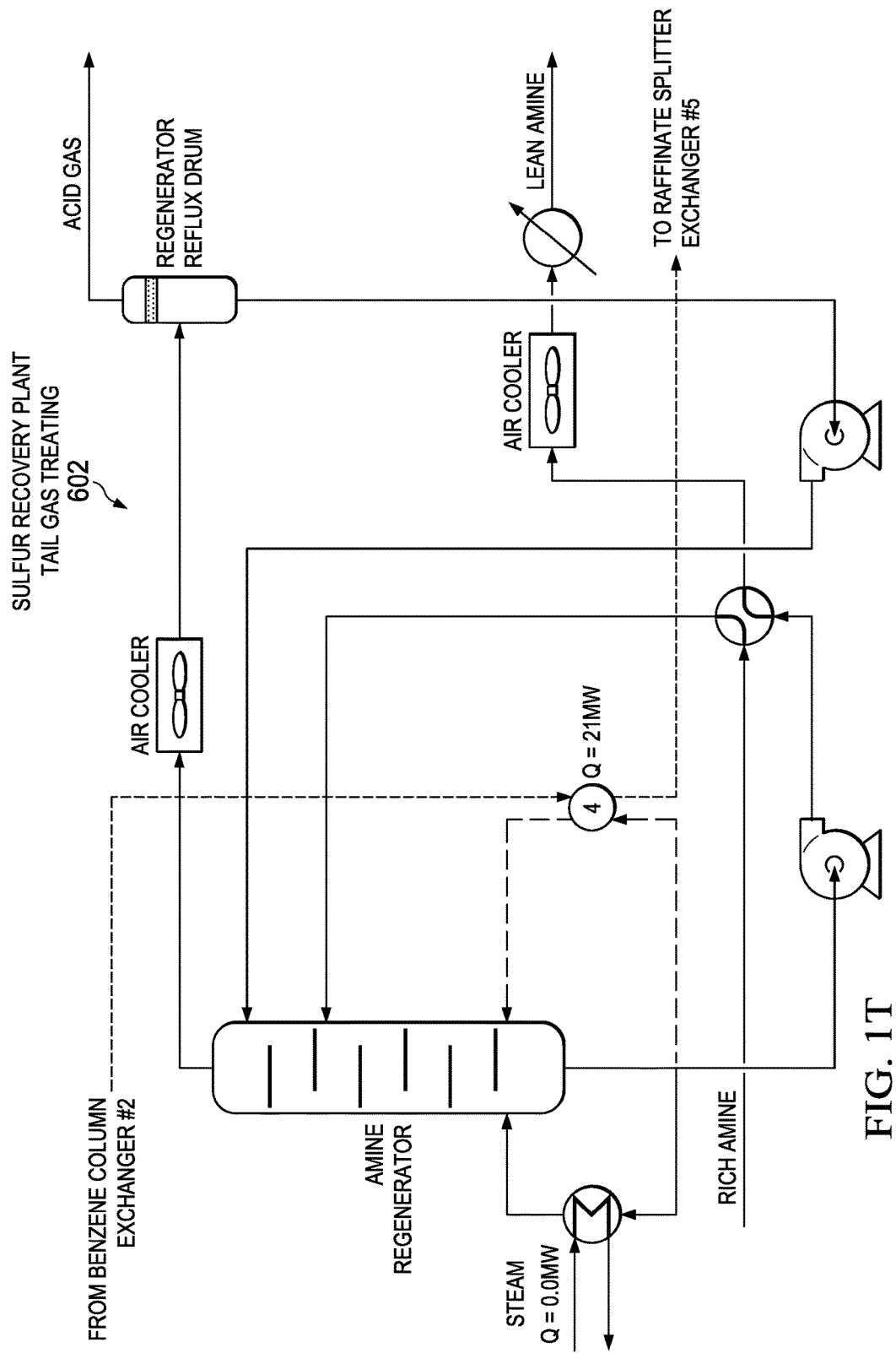

FIG. 1T shows the sulfur recovery plant 602 in a crude oil refinery facility. The second heated buffer fluid stream is flowed to the sulfur recovery plant 602. An amine regenerator bottoms stream is heated using the second heated buffer fluid branch in a fourth heat exchanger with a thermal duty that can range between about 15 MW and 25 MW (for example, 21 MW). The fourth heat exchanger is coupled to, in series with and is downstream of the first heat exchanger relative to flow of the buffer fluid. In this manner, the third and the fourth heat exchangers can be coupled to each other in parallel relative to the flow of the buffer fluid. As shown in FIG. 1R, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column. The second heated buffer fluid branch exiting the fourth heat exchanger is flowed to the aromatics complex benzene extraction plant 618.

Figure 1U:
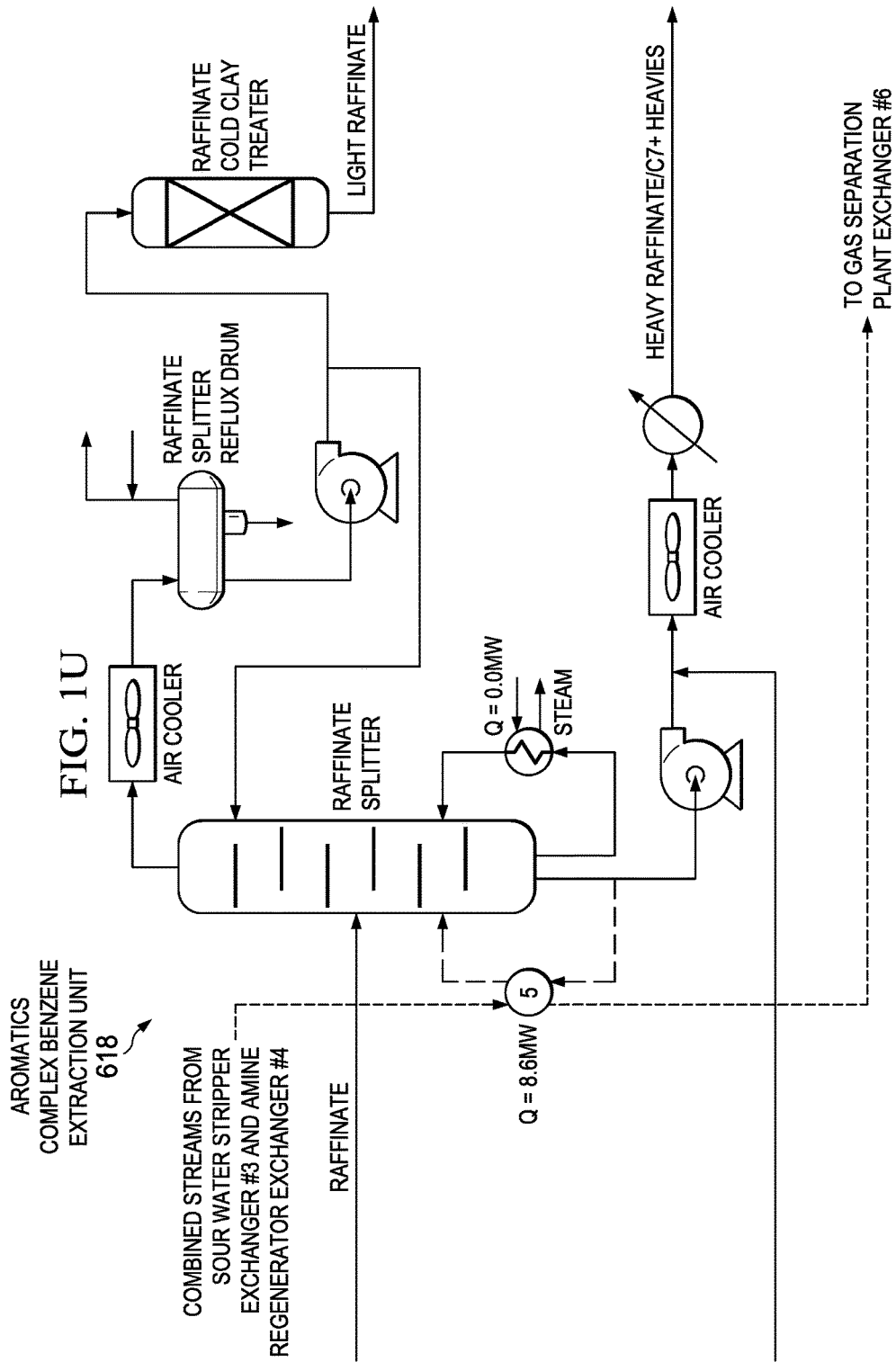

FIG. 1U also shows the aromatics complex benzene extraction unit 618 in a crude oil refinery facility. The first heated buffer fluid stream and the second heated buffer fluid stream are flowed to and recombined into a recombined heated buffer fluid stream in the benzene extraction unit 618. The raffinate splitter bottoms stream is heated using the recombined buffer fluid in a fifth heat exchanger with a thermal duty that can range between about 5 MW and 15 MW (for example, 8.6 MW). The fifth heat exchanger is coupled to, in series with and is downstream of the first heat exchanger relative to flow of the buffer fluid. As shown in FIG. 1U, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Figure 1V:
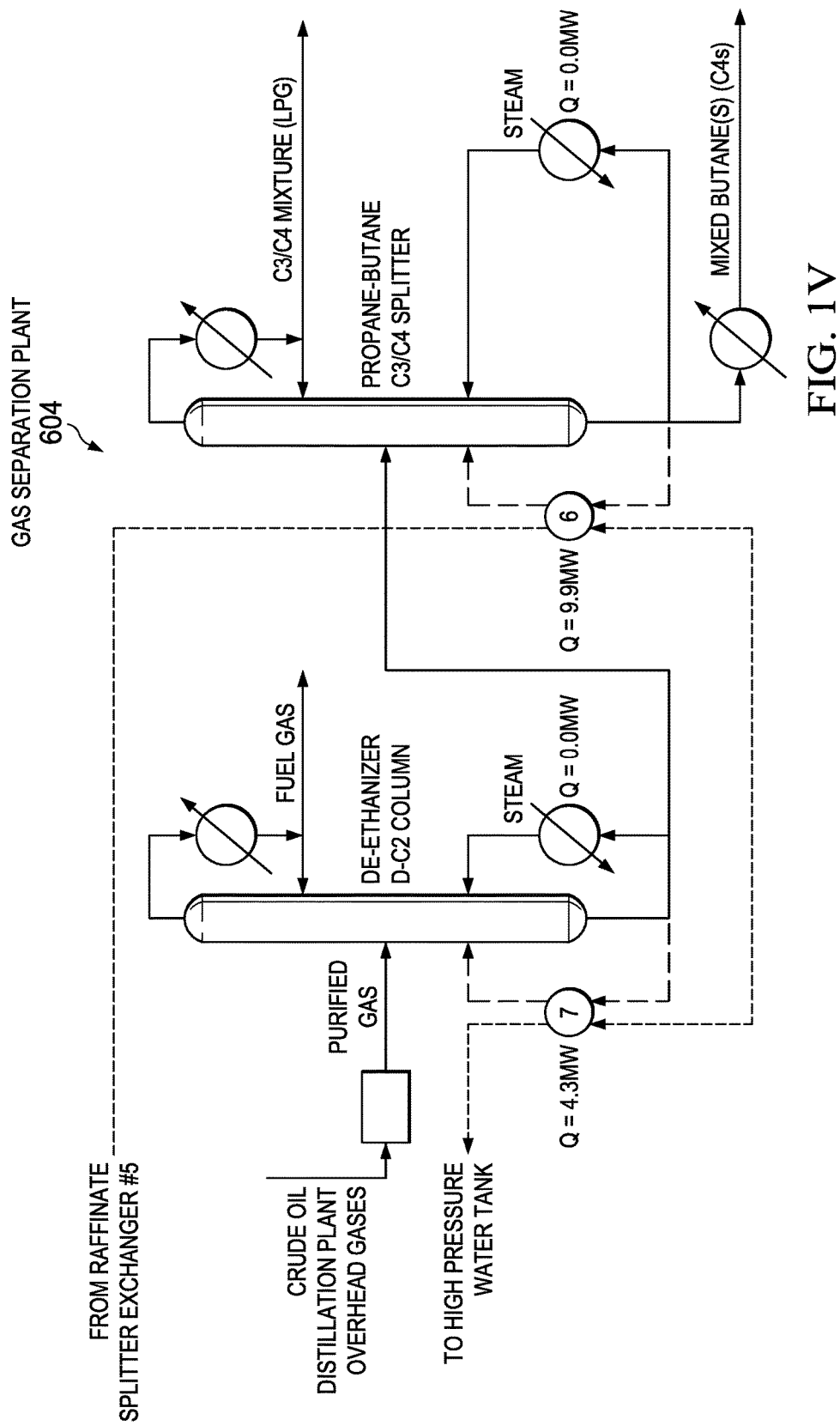

FIG. 1V shows the gas separation plant 604 in a crude oil refinery facility. The recombined heated buffer fluid is flowed to the gas separation plant 604. A C3/C4 splitter bottoms stream is heated using the recombined heated buffer fluid in a sixth heat exchanger with a thermal duty that can range between about 5 MW and 15 MW (for example, 9.9 MW). The sixth heat exchanger is coupled to, in series with and is downstream of the first heat exchanger relative to the buffer fluid flow. As shown in FIG. 1V, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

Also as shown in FIG. 1V, a de-ethanizer bottoms stream in the gas separation plant 604 is heated using the recombined heated buffer fluid in a seventh heat exchanger with a thermal duty that can range between about 1 MW and 10 MW (for example, 4.3 MW). The seventh heat exchanger is coupled to, in series with and is downstream of the first heat exchanger relative to the buffer fluid flow. As shown in FIG. 1V, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

The recombined heated buffer fluid exiting the seventh heat exchanger is flowed to the buffer fluid tank for reuse. The second, set of third and fourth, the fifth, the sixth, and the seventh heat exchangers are coupled to one another in series relative to the flow of heated buffer fluid. As stated previously, the third and the fourth heat exchangers are parallel to one another relative to the flow of the heated buffer fluid.

In some implementations, the heated buffer fluid can be flowed in series through the different plants. For example, the heated buffer fluid can be flowed first to the gas separation plant then to any other first plant. As well, the order of heated buffer fluid intra-plant can be different, for example, the heated buffer fluid can flow first through the de-ethanizer bottoms exchanger and then the C3/C4 splitter bottoms exchanger. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from the aromatics complex xylene products separation unit can result in decreasing or eliminating the heat energy for heating the sulfur recovery plant, the aromatics complex benzene extraction plant, the sour water stripper plant, the gas separation plant or combinations of them such as by about 82 MW.

Configuration 3

Figure 1W:
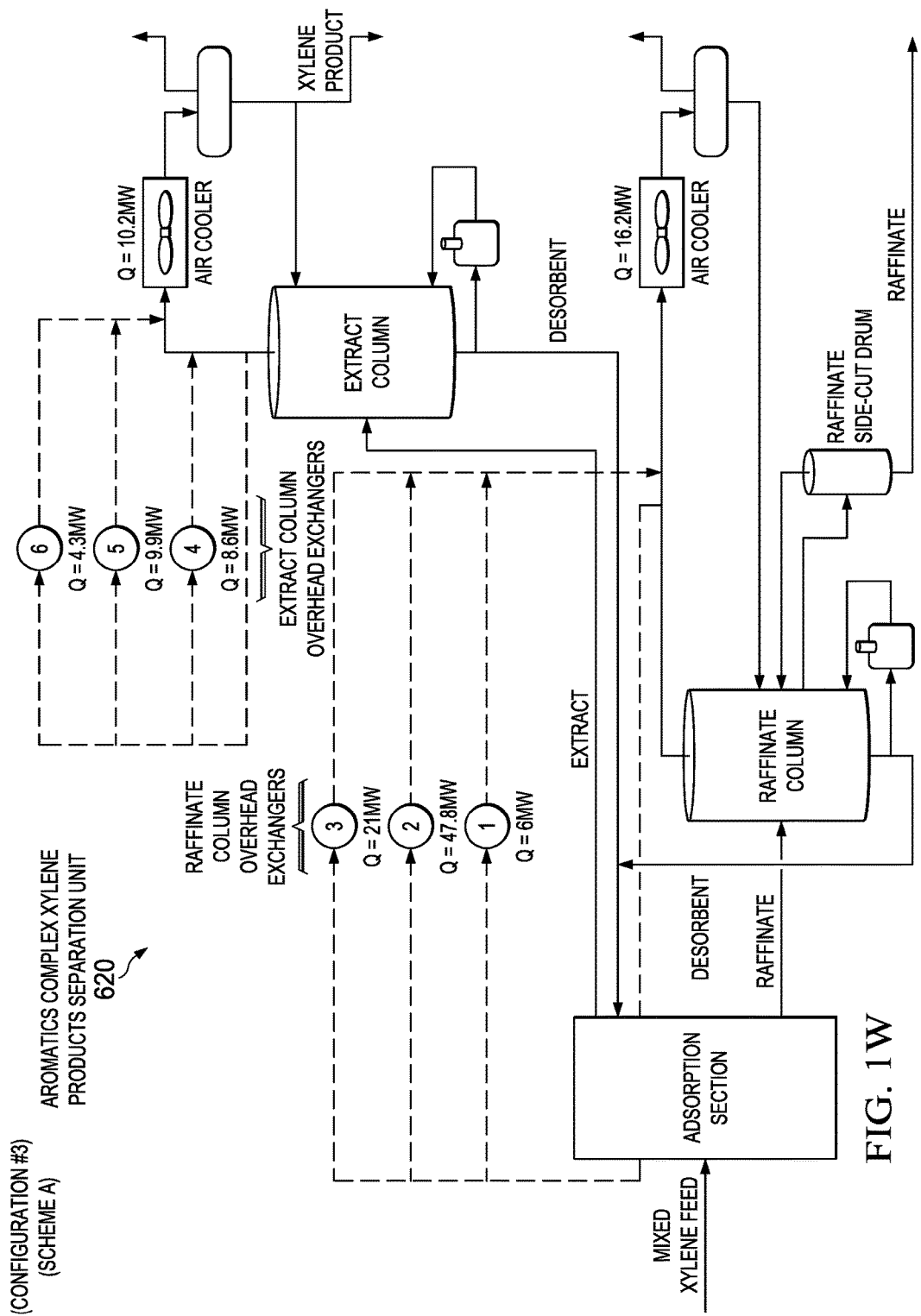

FIGS. 1W-1AH illustrate configurations and related scheme details for thermally integrating different refining plants in the crude oil refining facility. The thermal integration described in these configurations and illustrated in FIGS. 1W-1AH can reduce the crude oil refining facility's energy consumption (for example, heating and cooling utilities). For example, a reduction in energy consumption by about 98 MW can translate to at least about 15% of the energy consumption in the crude oil refining facility. In certain schemes, a process stream from one refining plant can be used to directly heat another process stream from another, different refining plant. In certain configurations, heat exchange between process streams can be implemented using an intermediate buffer fluid, for example, water, oil, or other buffer fluid.

Configuration 3—Scheme A

In some implementations, the multiple first streams in multiple first plants in the crude oil refining facility can be directly heated using a second stream in a second plant, and multiple third streams in multiple third plants in the crude oil refining facility can be directly heated using a fourth stream in the second plant. In some implementations, the multiple first plants and the multiple third plants share a common plant. In some instances, multiple first plants include the amine regeneration plant, the sulfur recovery plant, and the aromatics complex benzene extraction unit and, and the multiple first streams include a benzene column bottoms, an acid gas regenerator bottoms and an amine regenerator bottoms. The second plant include the aromatics complex, which can include an aromatics complex xylene products separation unit, the second stream can include a raffinate column overheads stream, and the fourth stream can include an extract column overheads stream. The multiple third plants can include the aromatics complex benzene extraction unit and the gas separation plant, and the multiple third streams include the de-ethanizer bottoms, a C3/C4 splitter bottoms streams and a raffinate splitter bottoms. In some instances, the shared common plant can be an aromatics complex benzene extraction unit.

FIG. 1W shows an aromatics complex xylene products separation unit 620 in a crude oil refinery facility that includes a raffinate column overheads stream. The raffinate overheads column stream can be flowed in the plant as a single stream and split into multiple streams or it can be flowed into the plant as multiple streams to facilitate heat recovery. A first raffinate column overhead stream can directly heat a benzene column bottom stream in a first heat exchanger with a thermal duty that can range between about 1 MW and 10 MW (for example, 6 MW). A second raffinate column overhead stream can directly heat an acid gas regenerator bottom stream in a second heat exchanger with a thermal duty that can range between about 45 MW and 55 MW (for example, 47.8 MW). A third raffinate column overhead stream can directly heat an amine regenerator bottom stream with a thermal duty that can range between about 15 MW and 25 MW (for example, 21 MW). In this manner, the first heat exchanger, the second heat exchanger, and the third heat exchanger can be coupled to each other in parallel relative to the flow of raffinate column overheads. The parallel set of raffinate column overhead exchangers transfer heat directly to other process streams that would have otherwise been discharged to the environment. The raffinate column overhead streams are recombined and returned to the aromatics plant xylene products separation unit 620 for further processing.

The aromatics complex xylene products separation unit 620 also includes an extract column overheads stream. The extract column overheads stream can be flowed in the plant as a single stream and split into multiple streams or it can be flowed into the plant as multiple streams to facilitate heat recovery. A first extract column overhead stream can directly heat a raffinate splitter bottom stream in a fourth heat exchanger with a thermal duty that can range between about 5 MW and 15 MW (for example, 8.6 MW). The second extract column overheads stream can directly heat a C3/C4 splitter bottoms stream in a fifth heat exchanger with a thermal duty that can range between about 5 MW and 15 MW (for example, 9.9 MW). A third extract column overhead stream can directly heat a de-ethanizer bottoms stream in a sixth heat exchanger with a thermal duty that can range between about 1 MW and 10 MW (for example, 4.3 MW). In this manner, the fourth, the fifth and the sixth heat exchangers can be coupled to each other in parallel relative to the flow of extract column overheads. The parallel set of extract column overhead exchangers transfer heat directly to other process streams that would have otherwise been discharged to the environment. The extract column overheads stream are recombined and returned to the aromatics plant xylene products separation unit 620 for further processing.

Figure 1X:
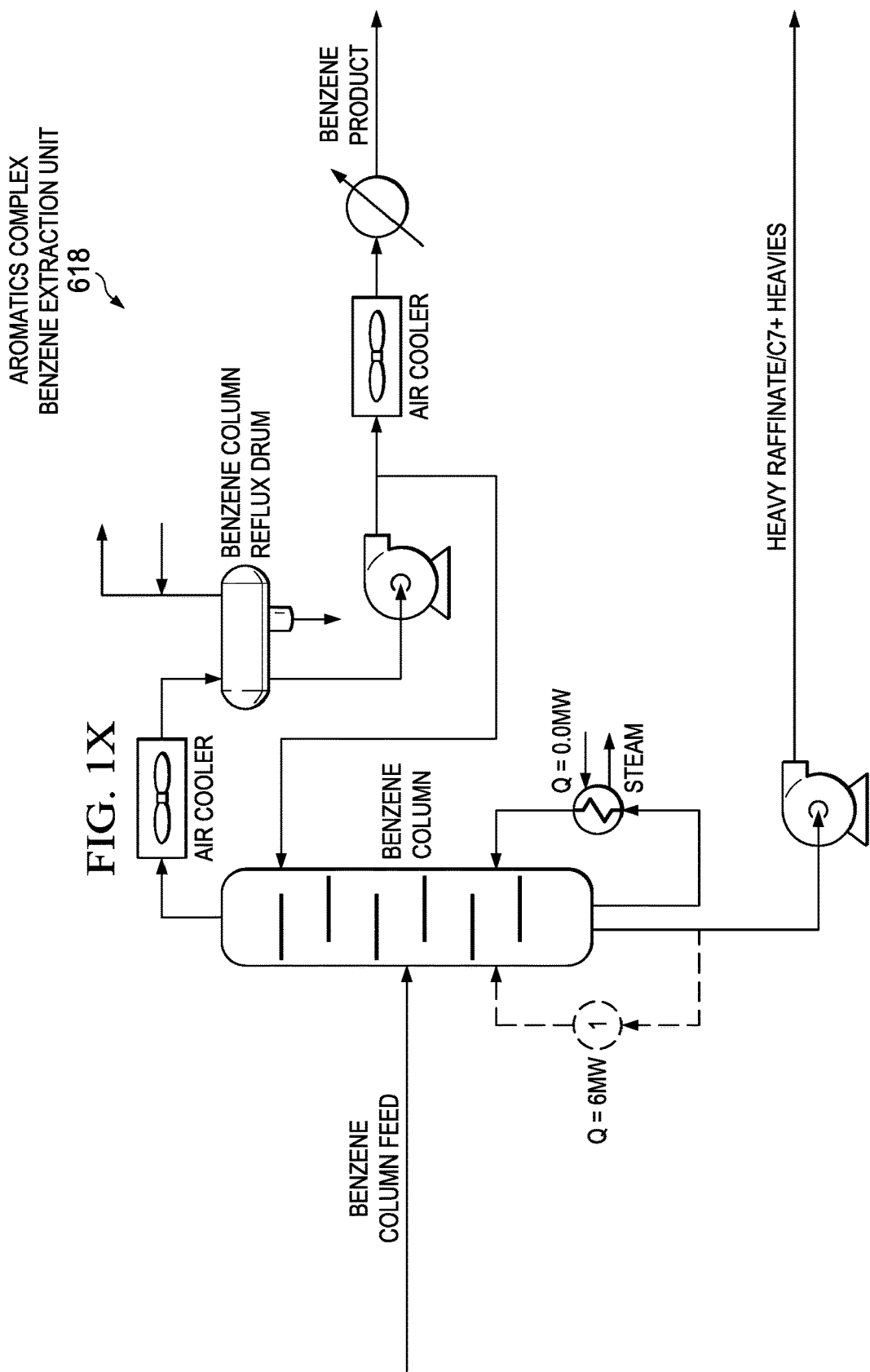

FIG. 1X shows the aromatics complex benzene extraction unit 618 in the crude oil refinery facility. The heated benzene column bottom stream can be flowed to the benzene extraction plant 618. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AA also shows the aromatics complex benzene extraction unit. Also, the heated raffinate splitter column bottoms stream can be flowed to the benzene extraction plant 618. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Figure 1Y:
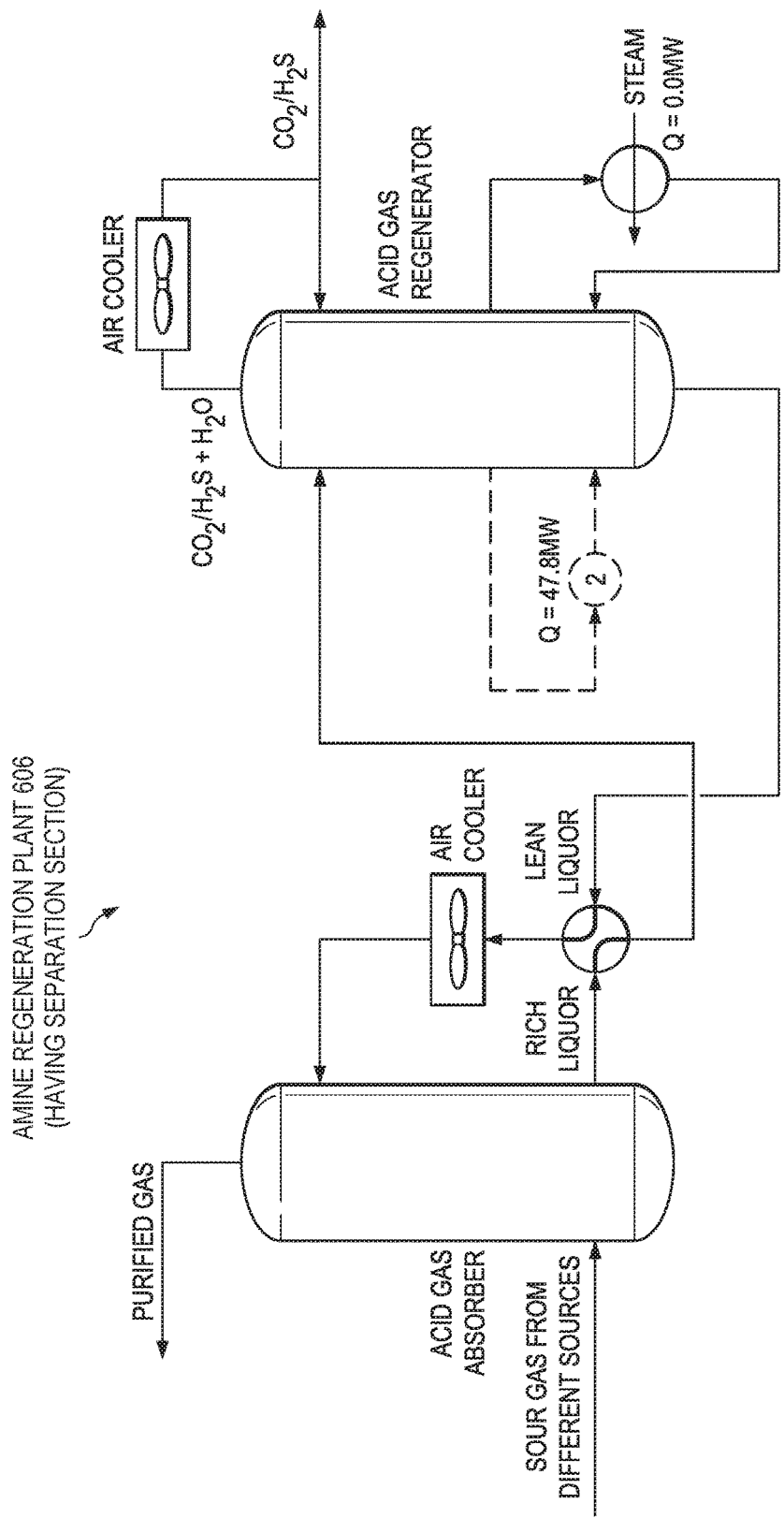

FIG. 1Y shows the amine regeneration plant 606 in the crude oil refinery facility. The heated acid gas regenerator bottoms stream can be flowed to the amine regeneration plant 606. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

Figure 1Z:
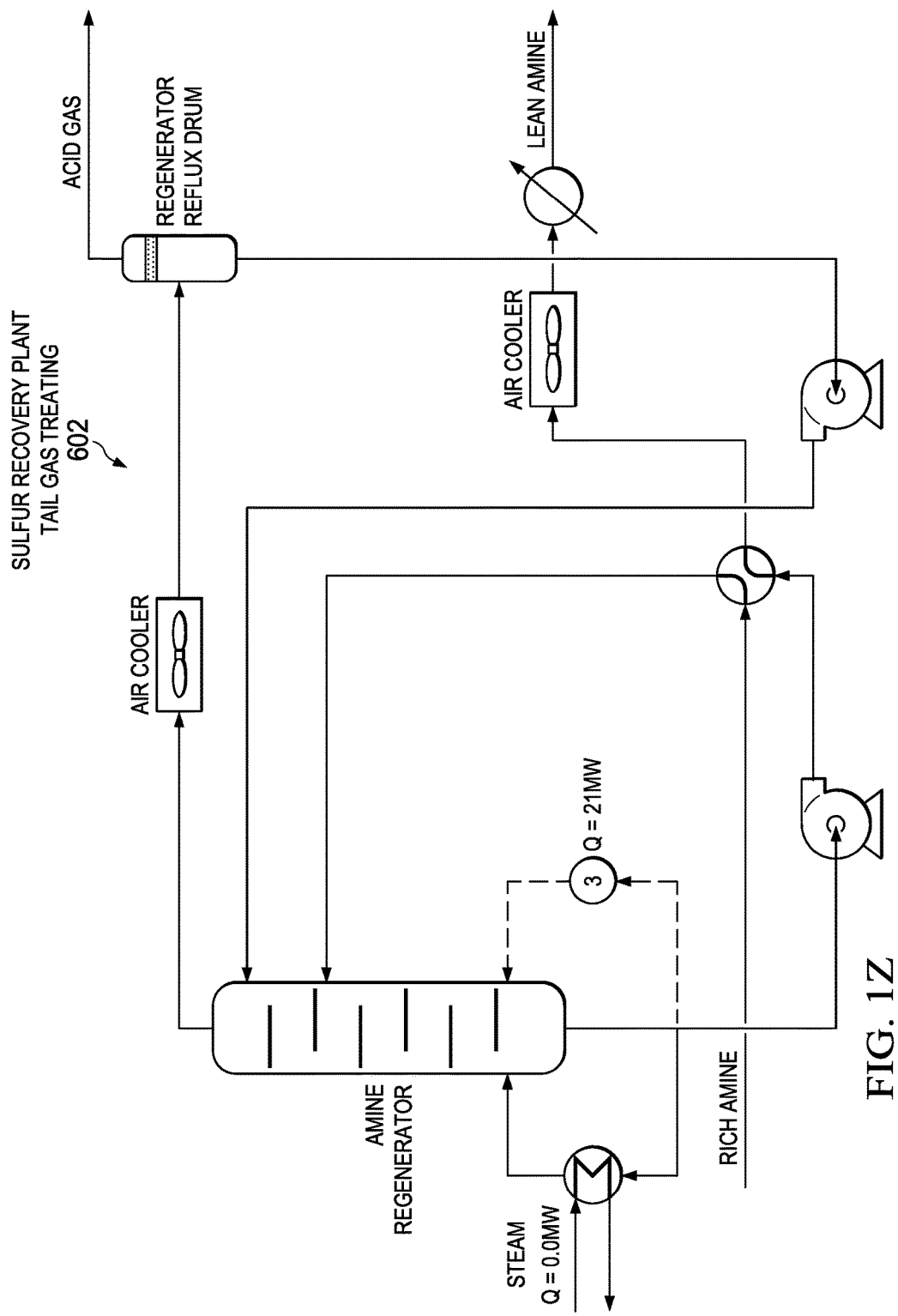
Figure 1A:
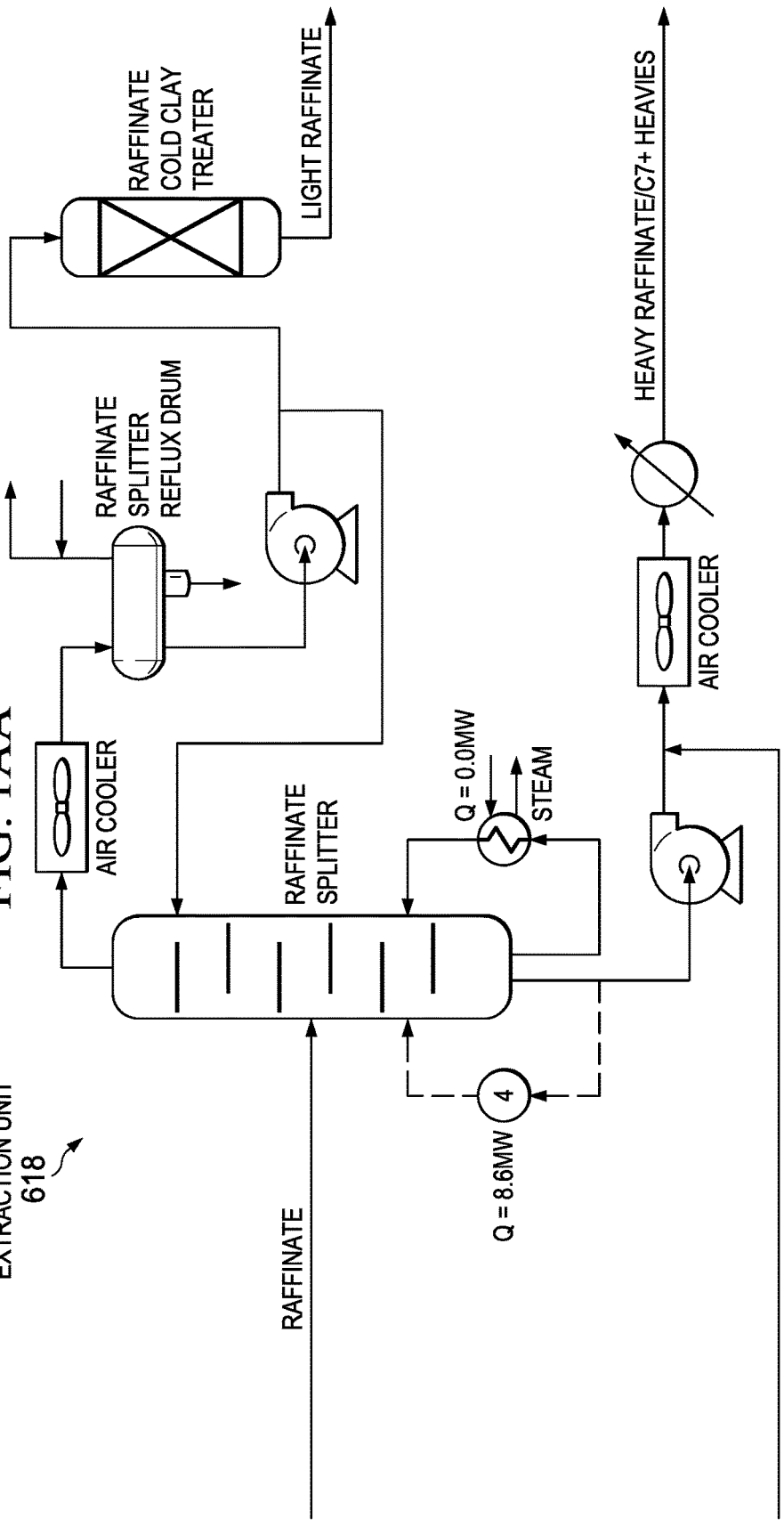
Figure 1A:
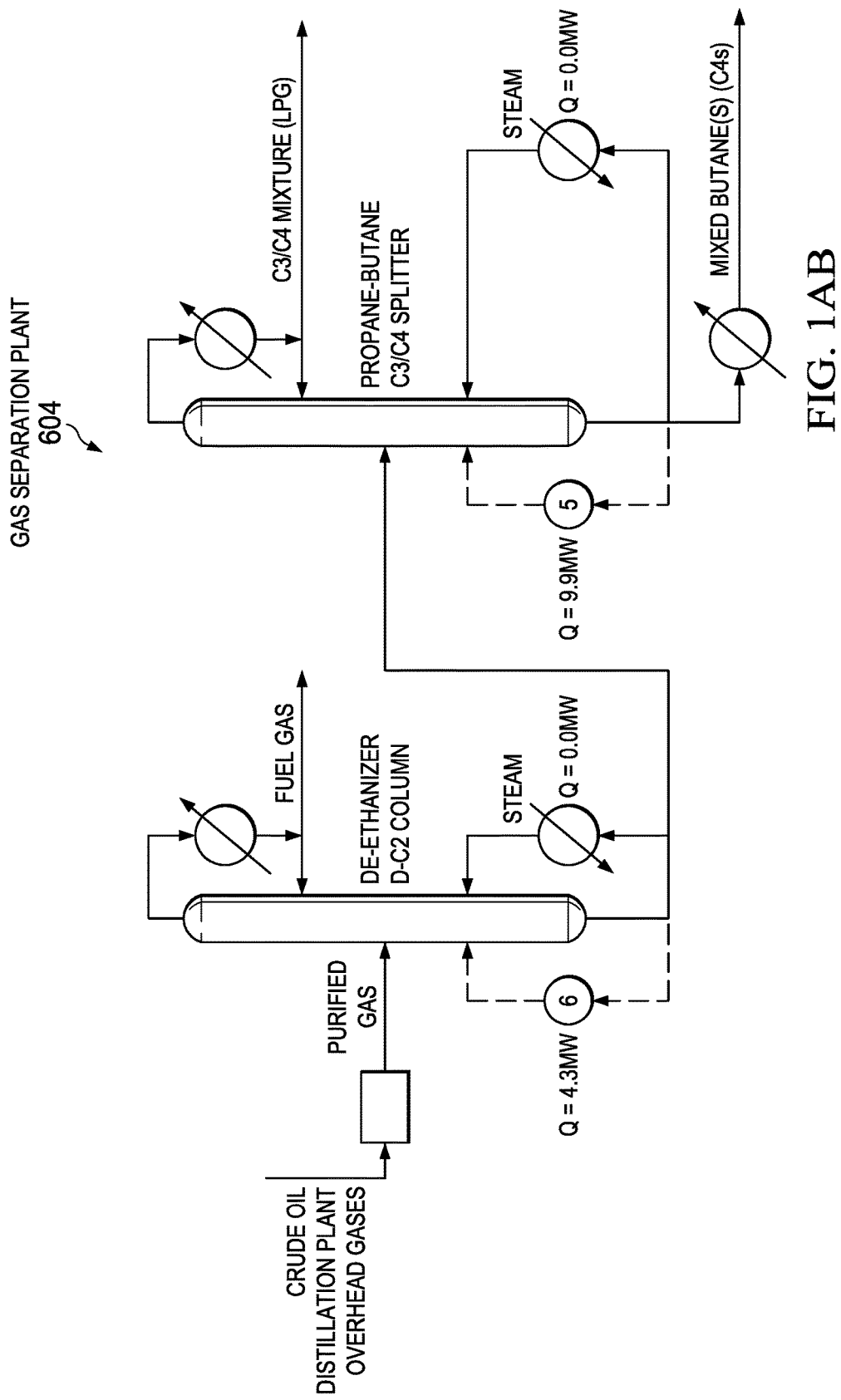
Figure 1A:
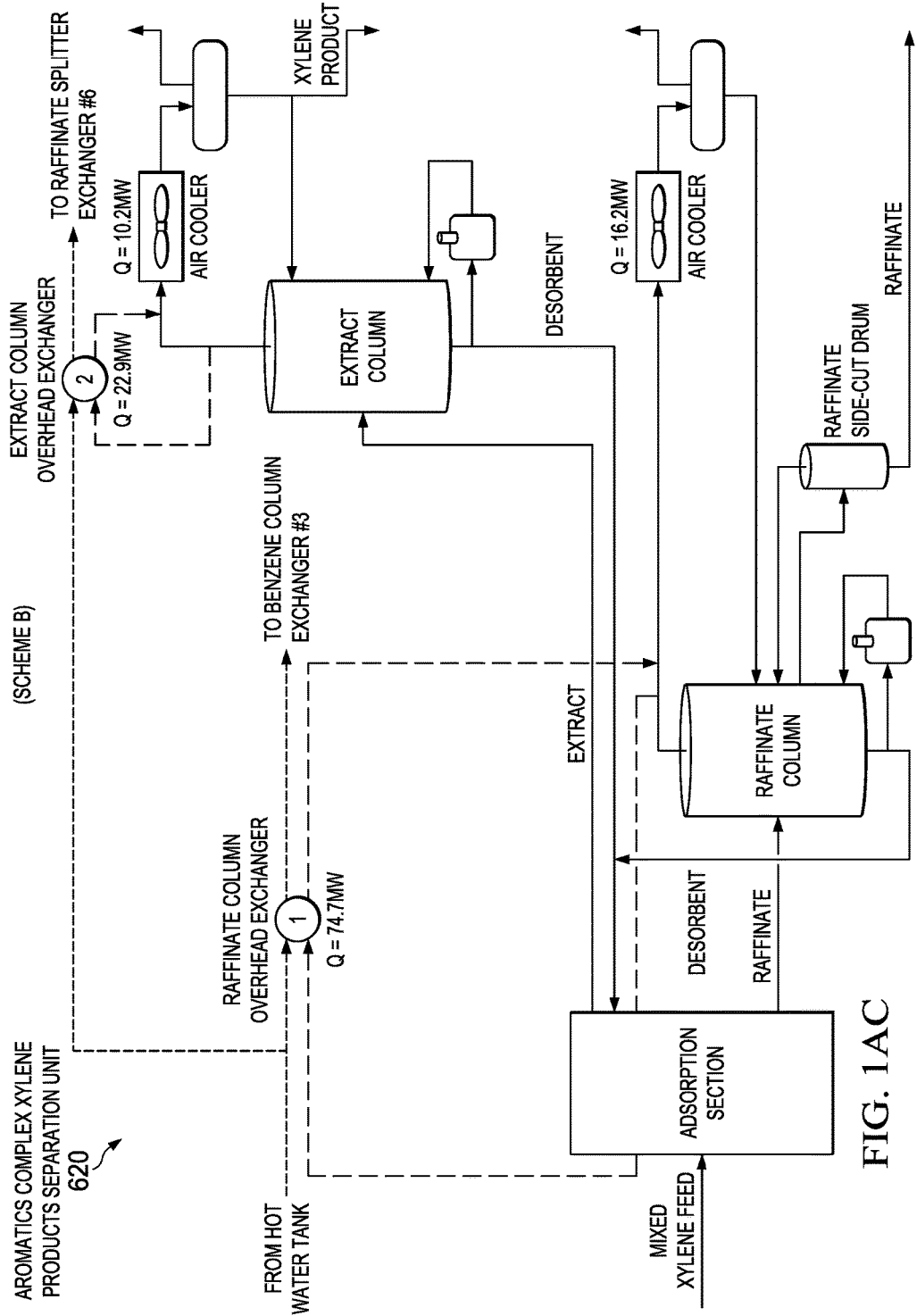
Figure 1A:
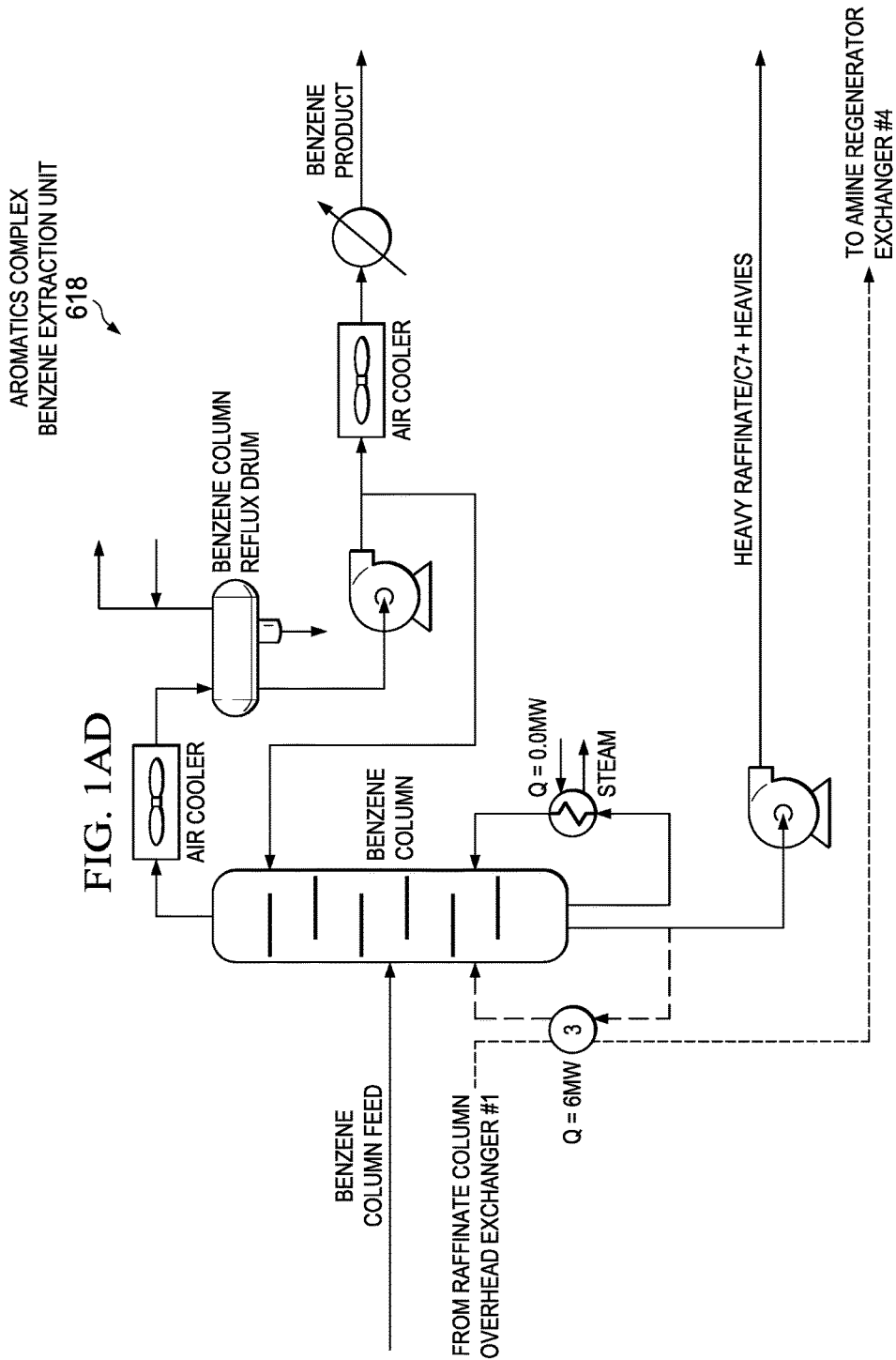
Figure 1A:
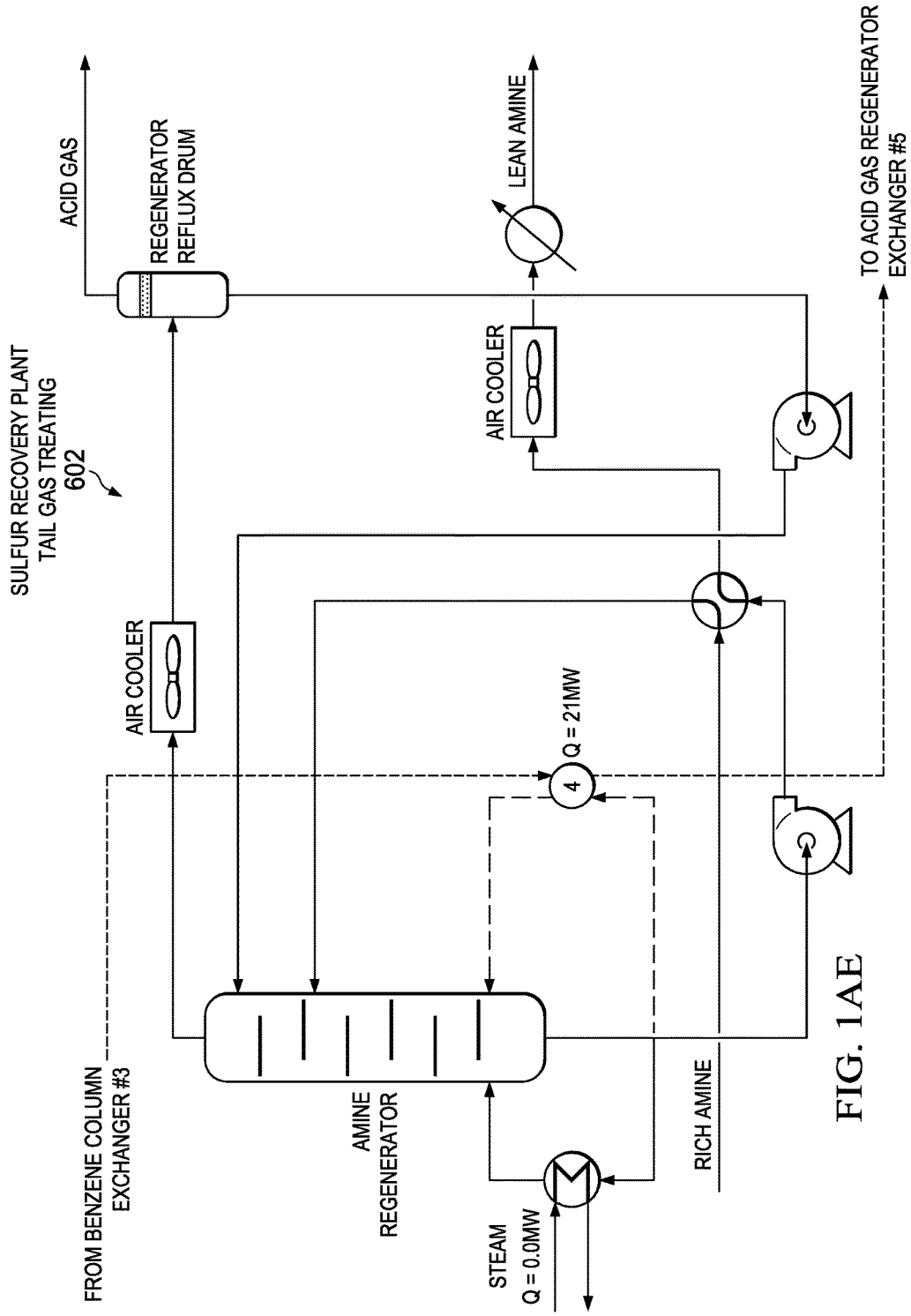
Figure 1A:
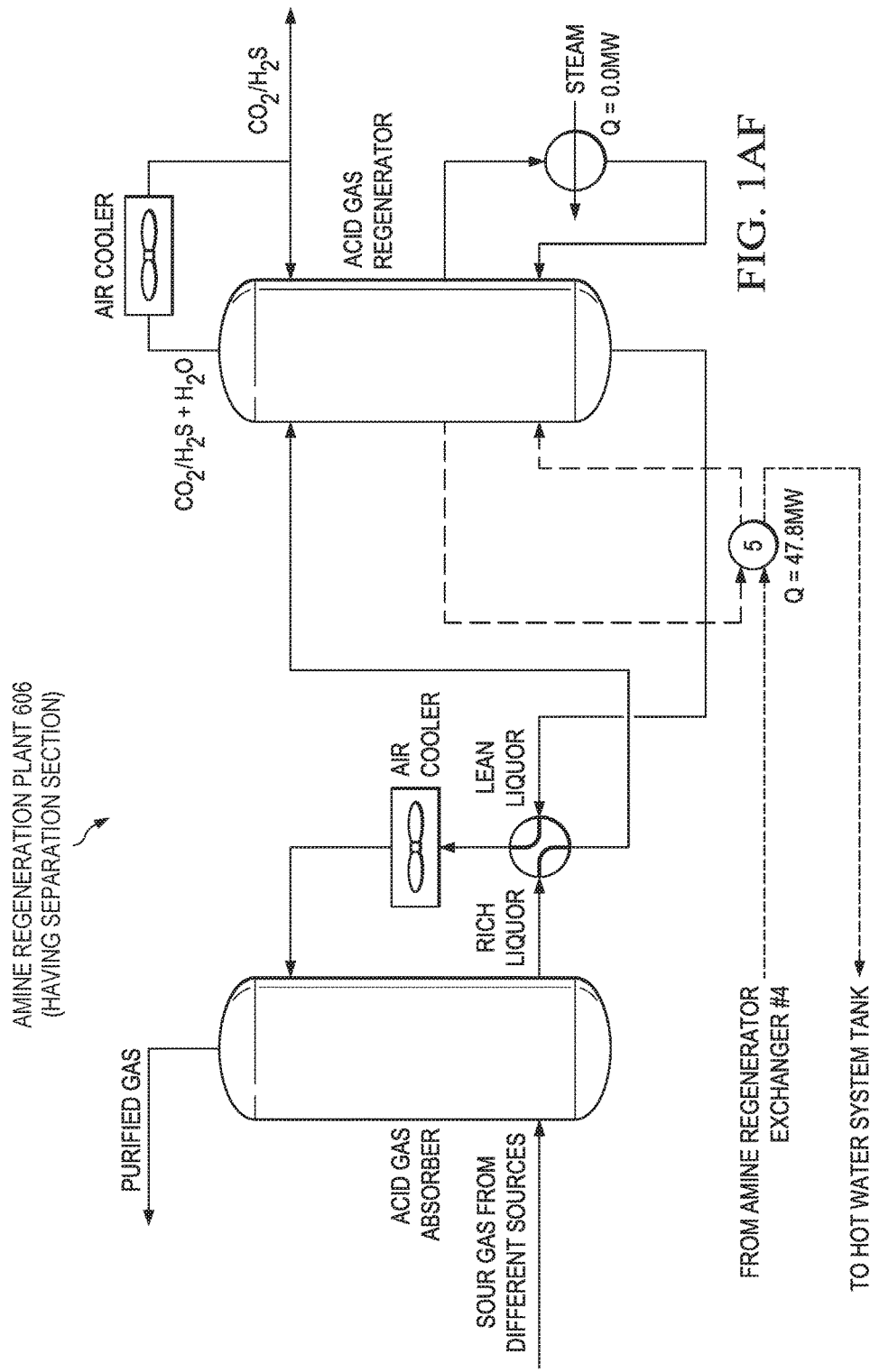
Figure 1A:
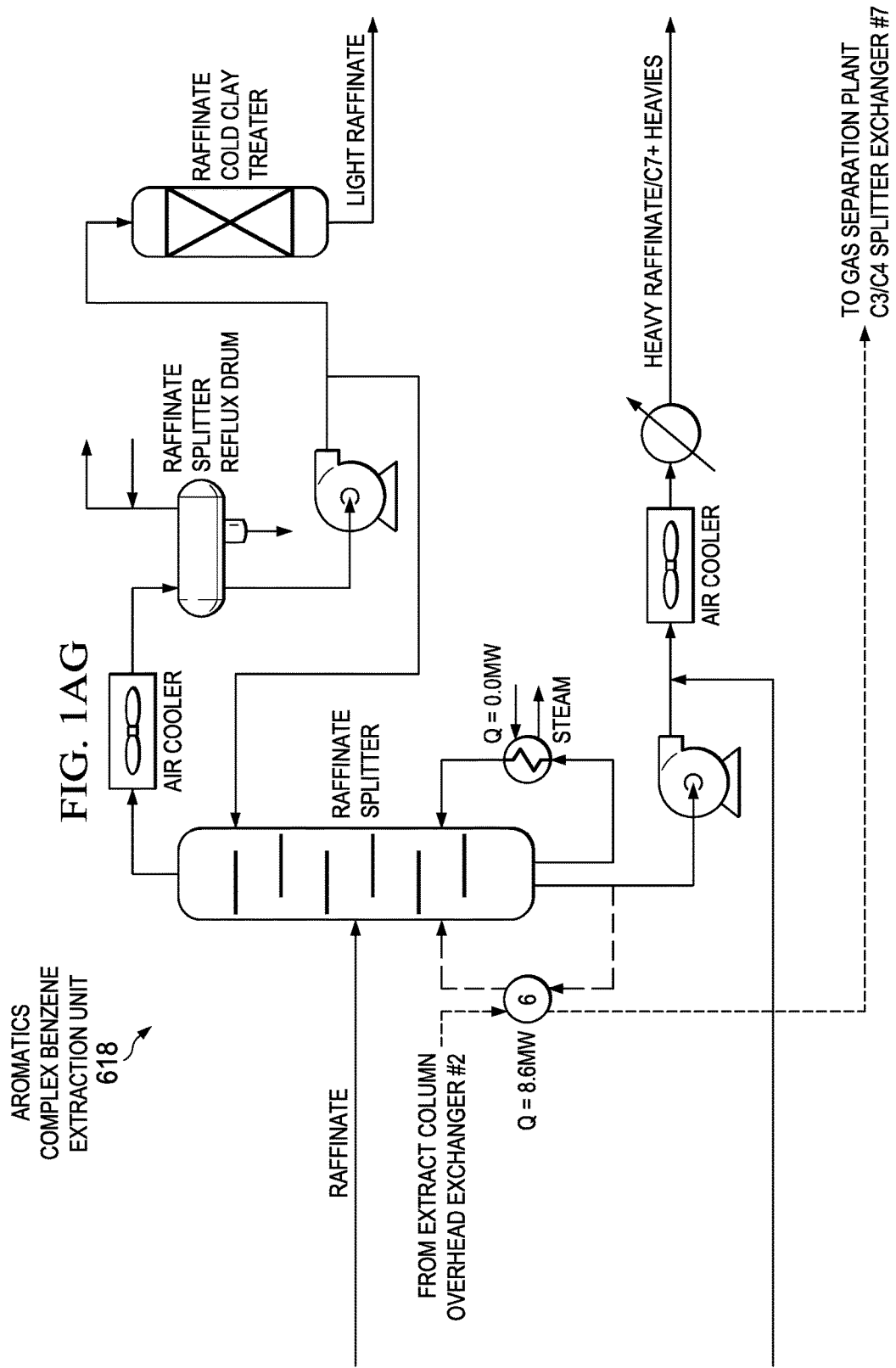
Figure 1A:
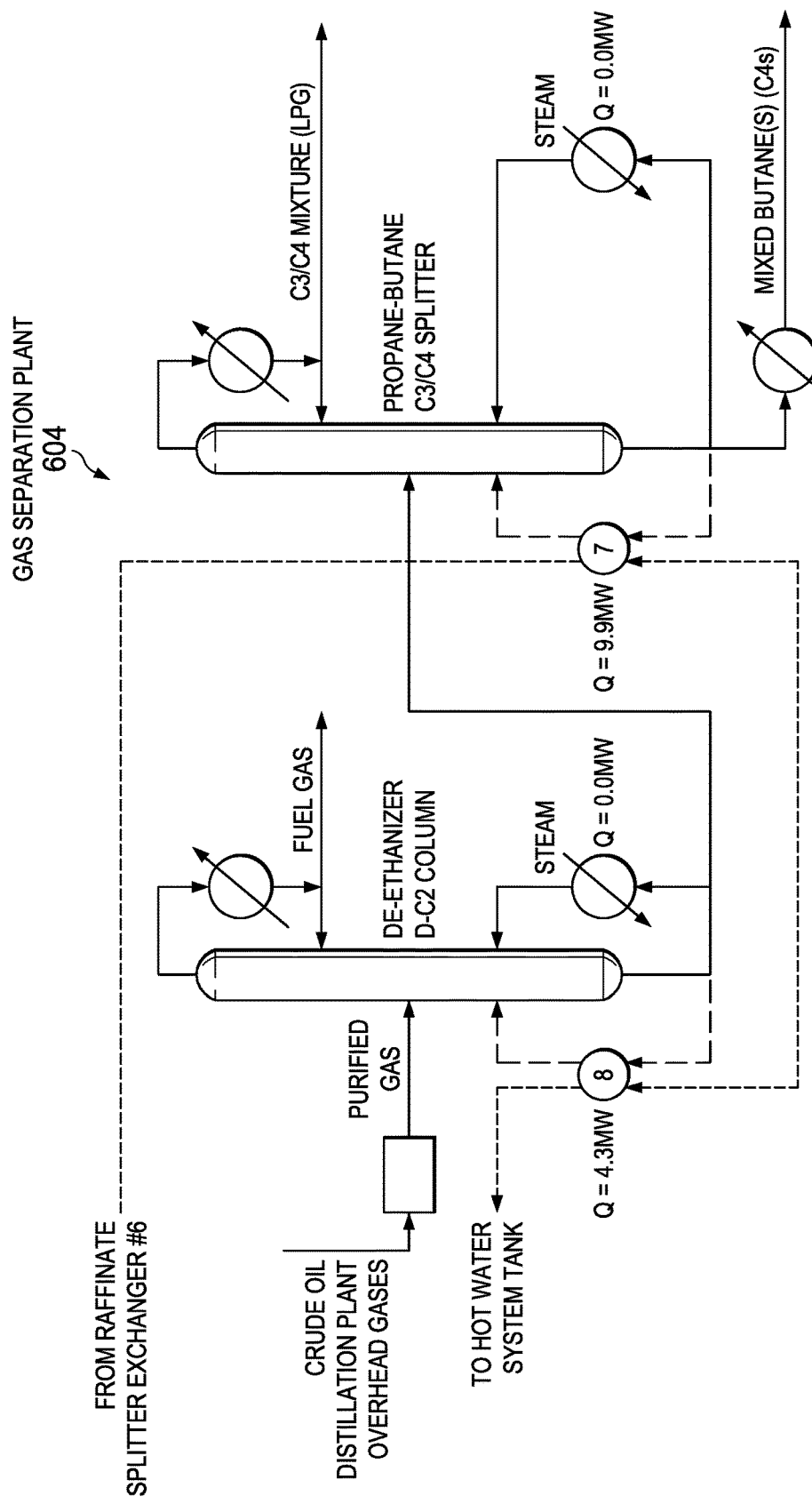
Figure 1A:
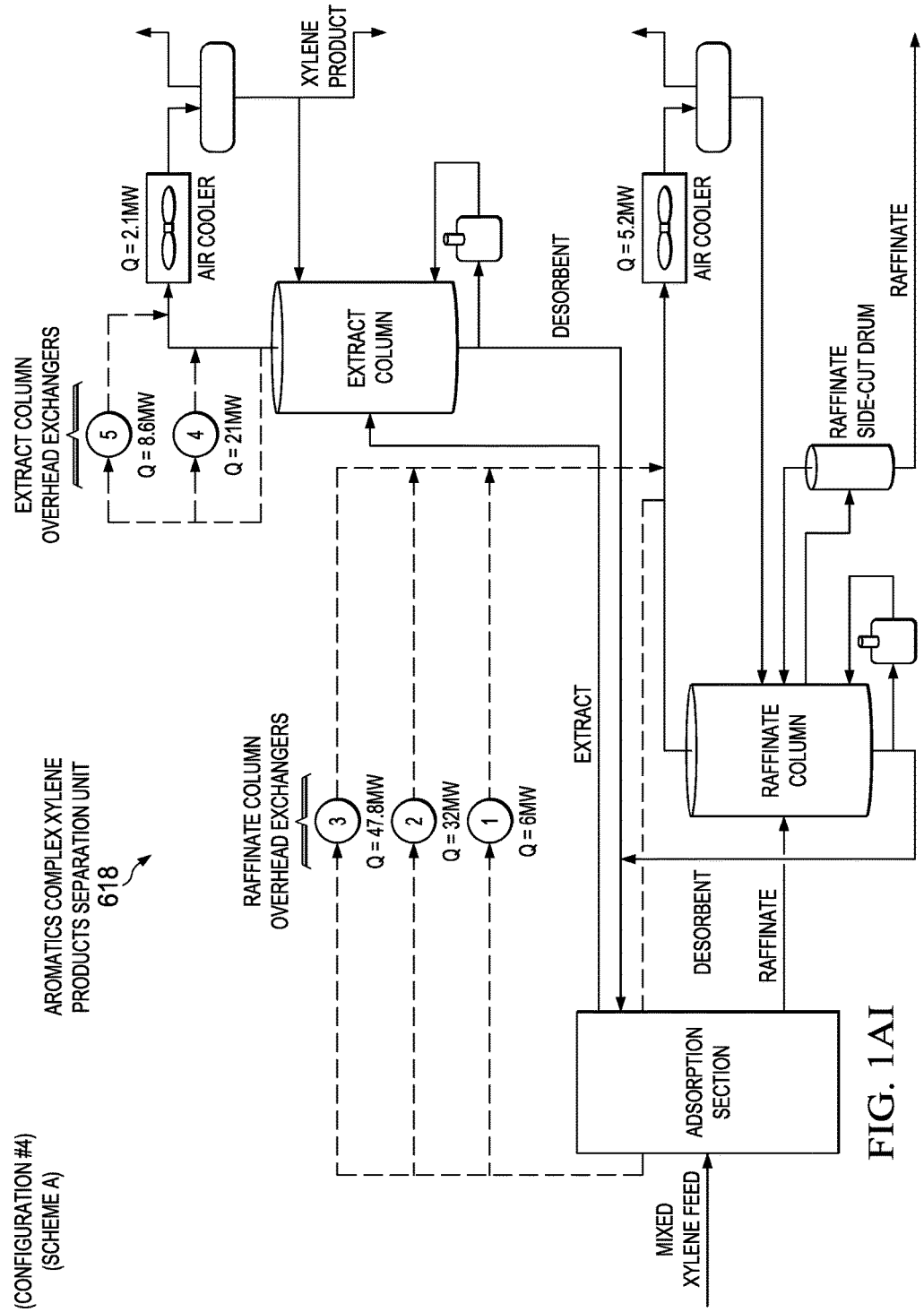
Figure 1A:
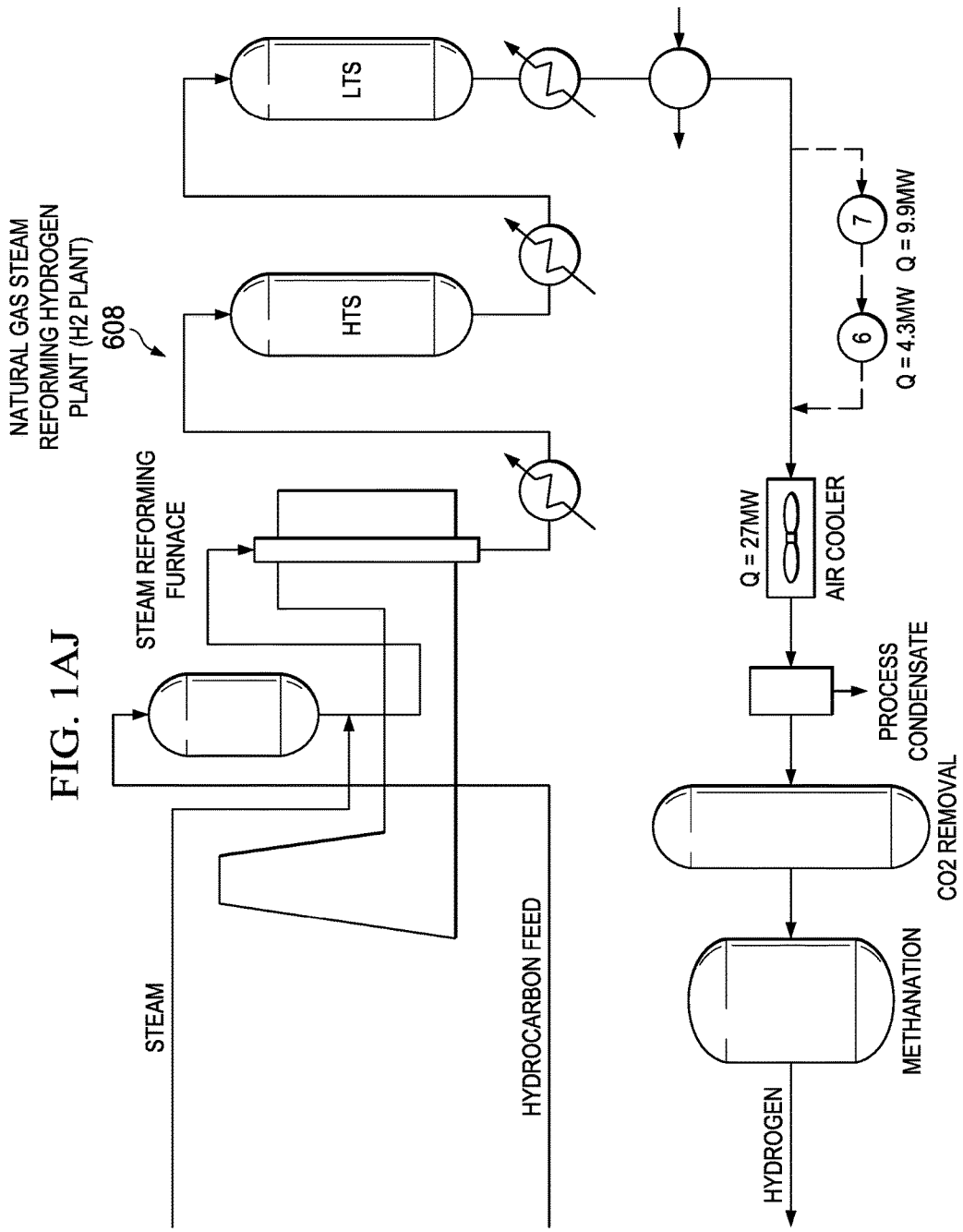
Figure 1A:
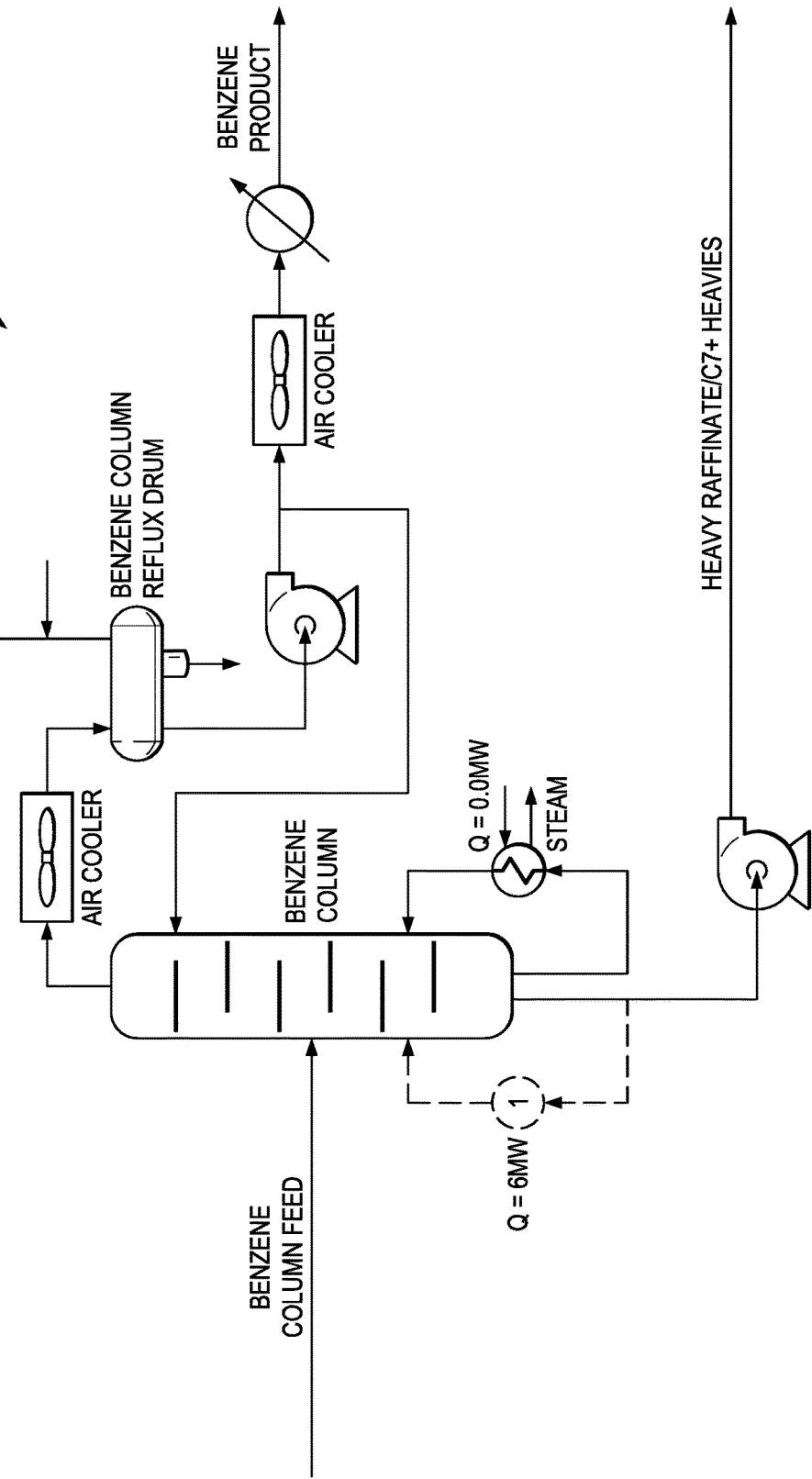
Figure 1A:
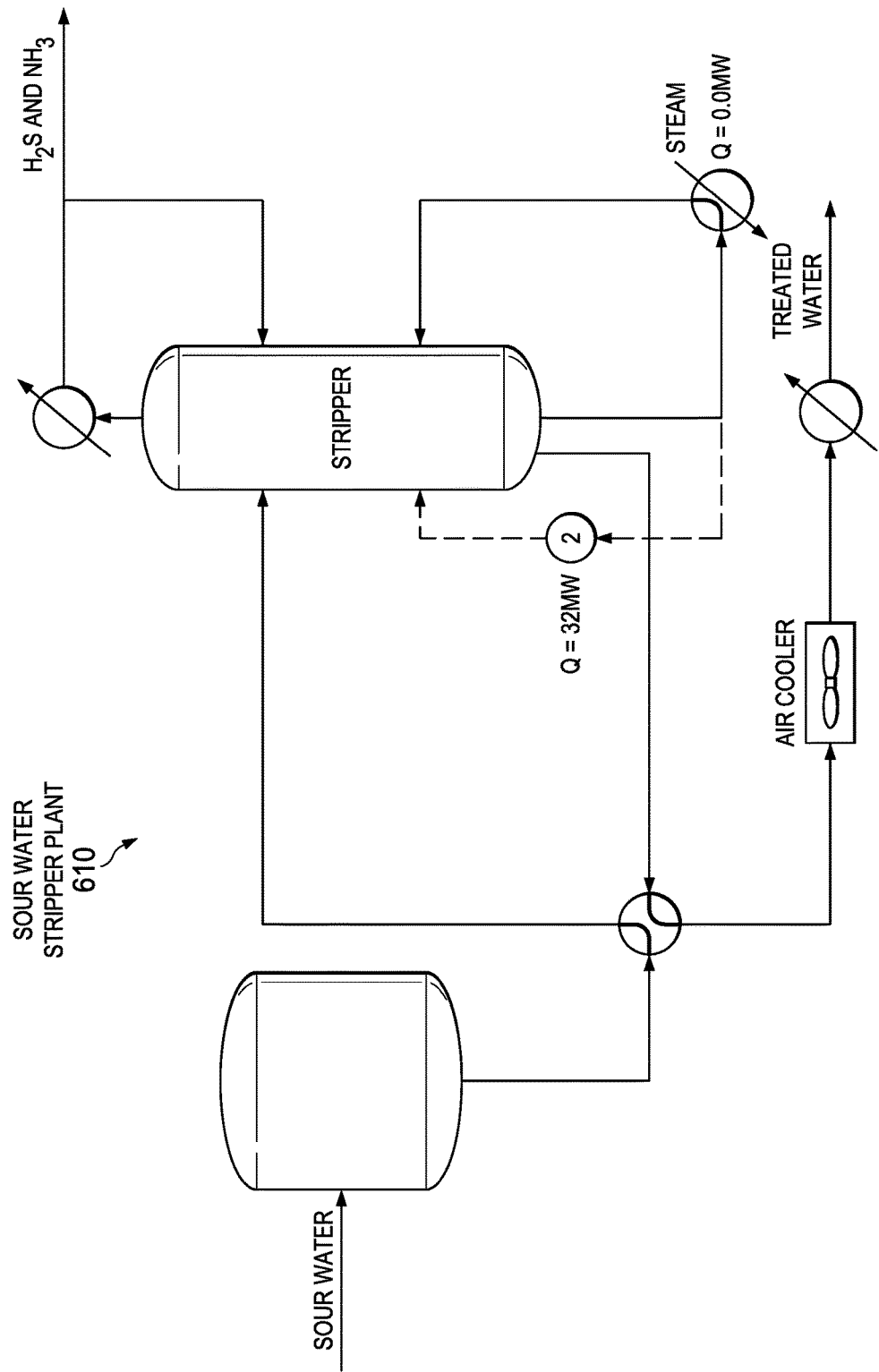
Figure 1A:
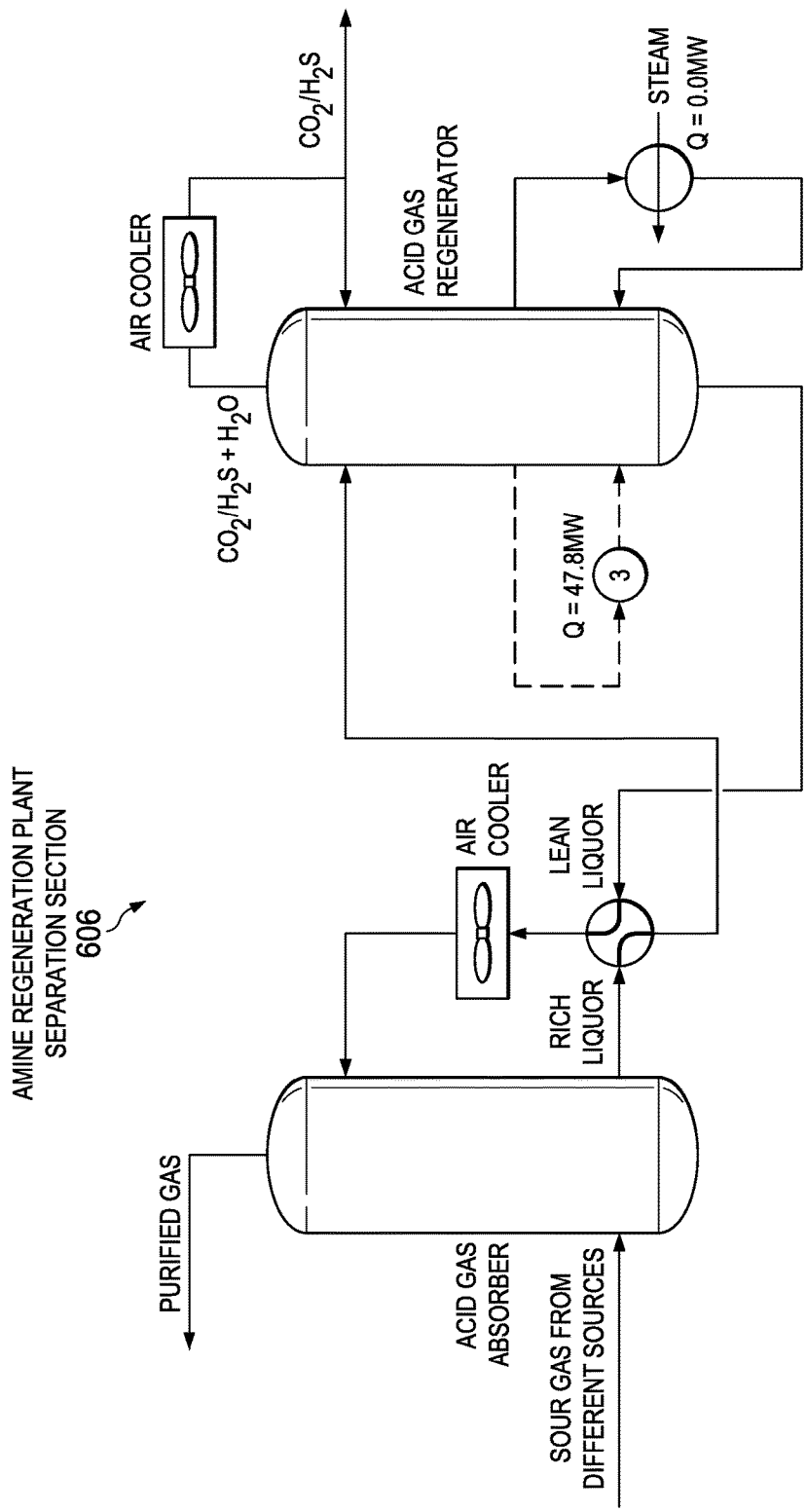
Figure 1A:
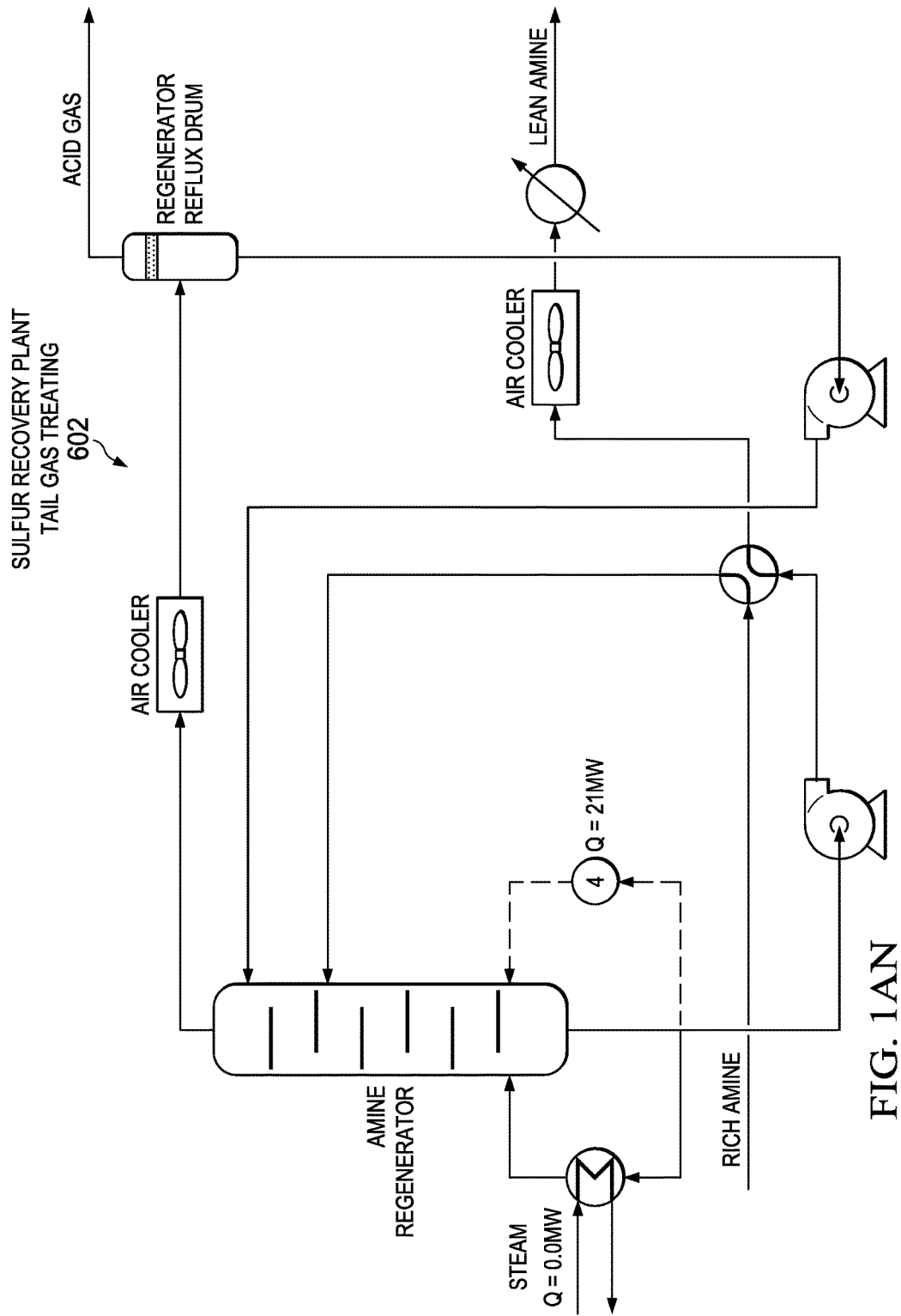
Figure 1A:
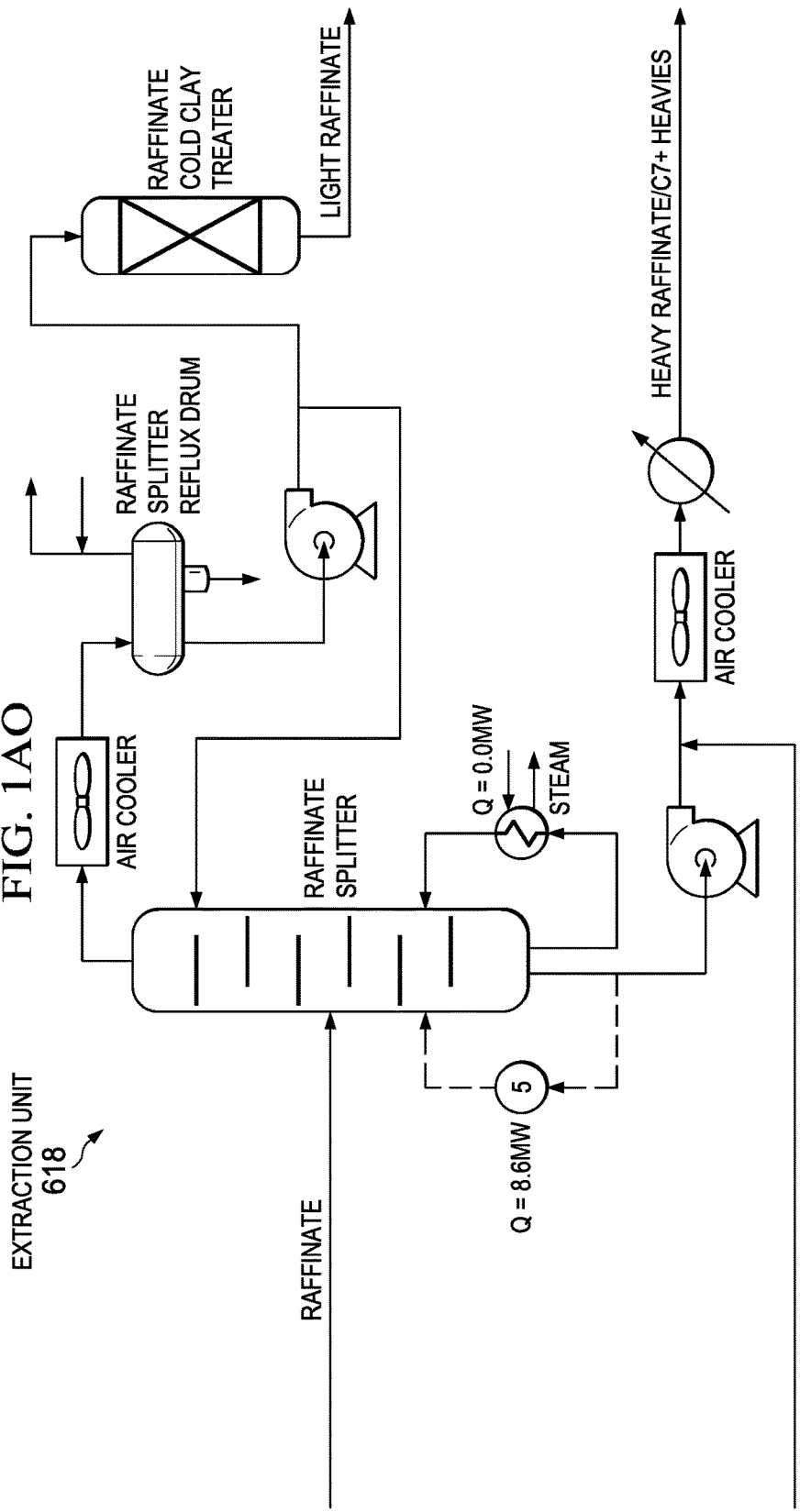
Figure 1A:
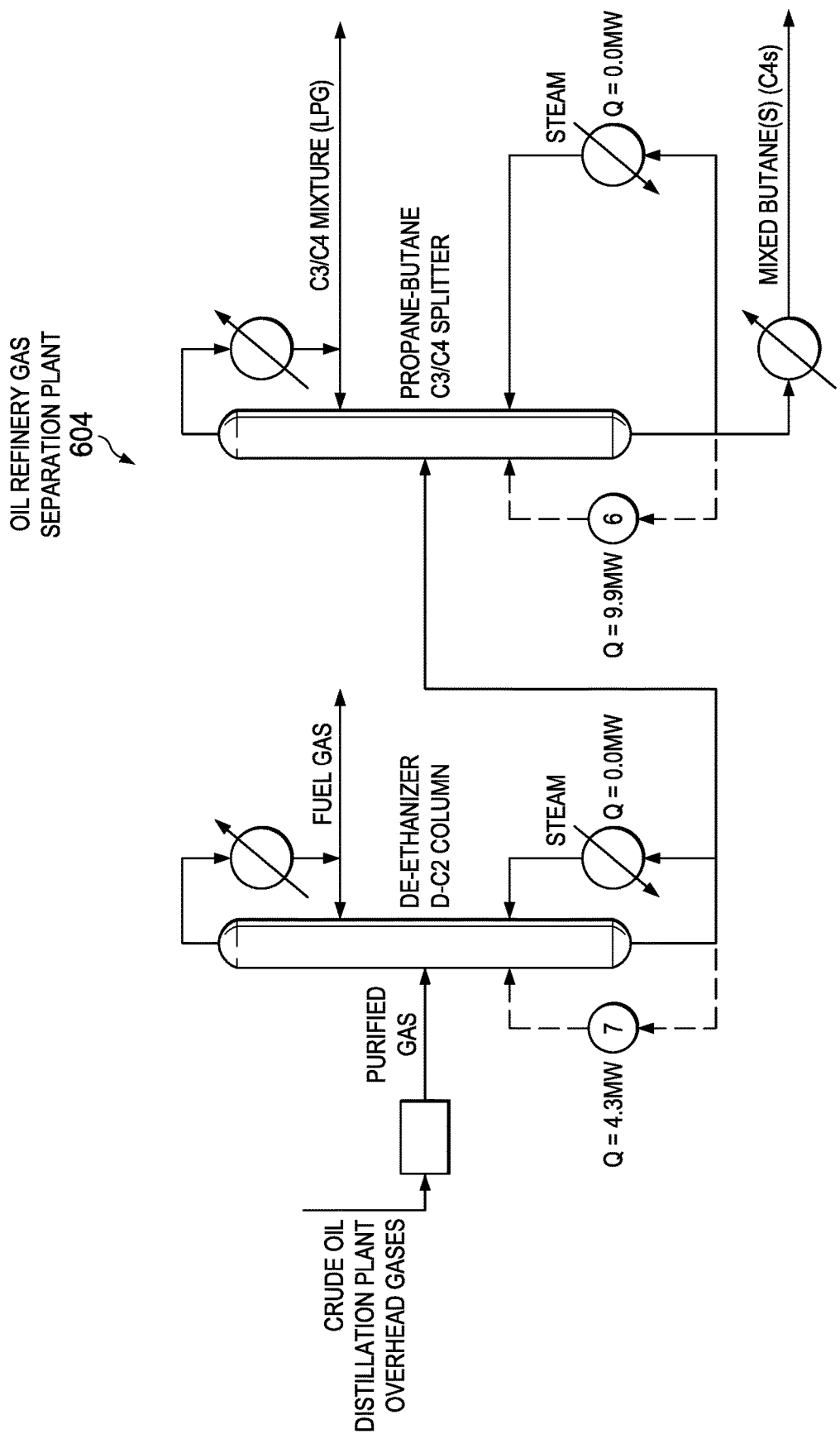
Figure 1A:
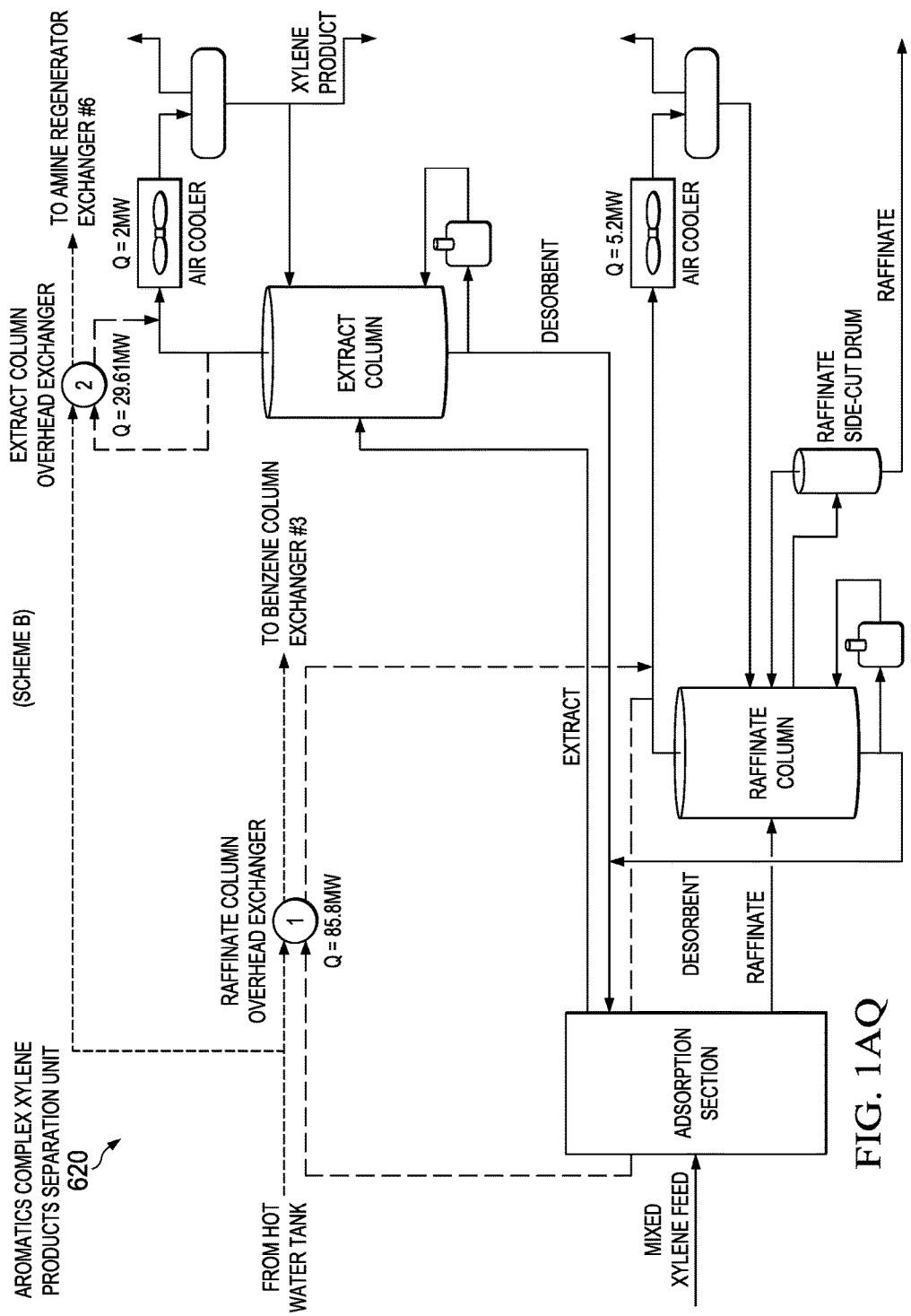
Figure 1A:
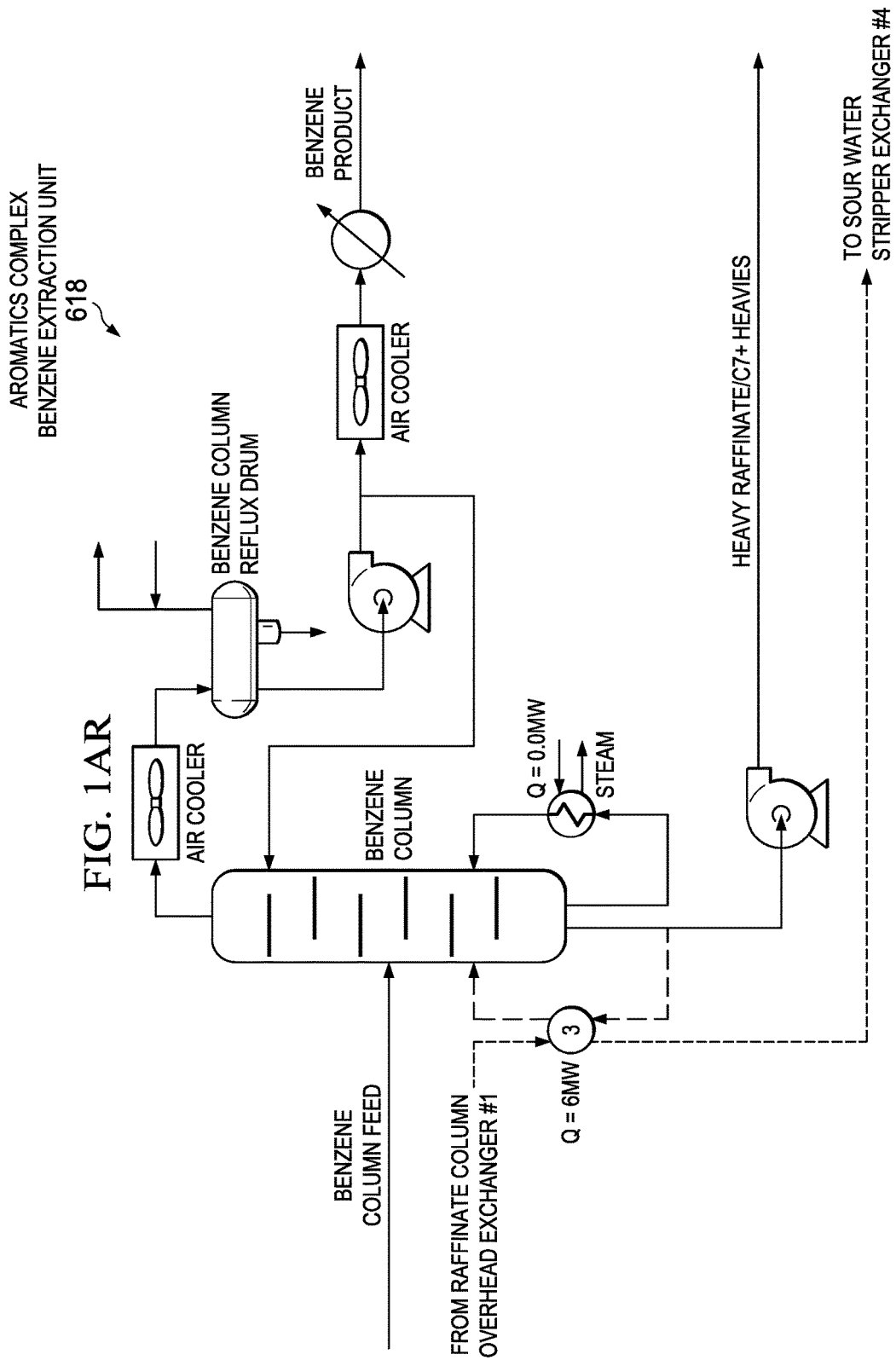
Figure 1A:
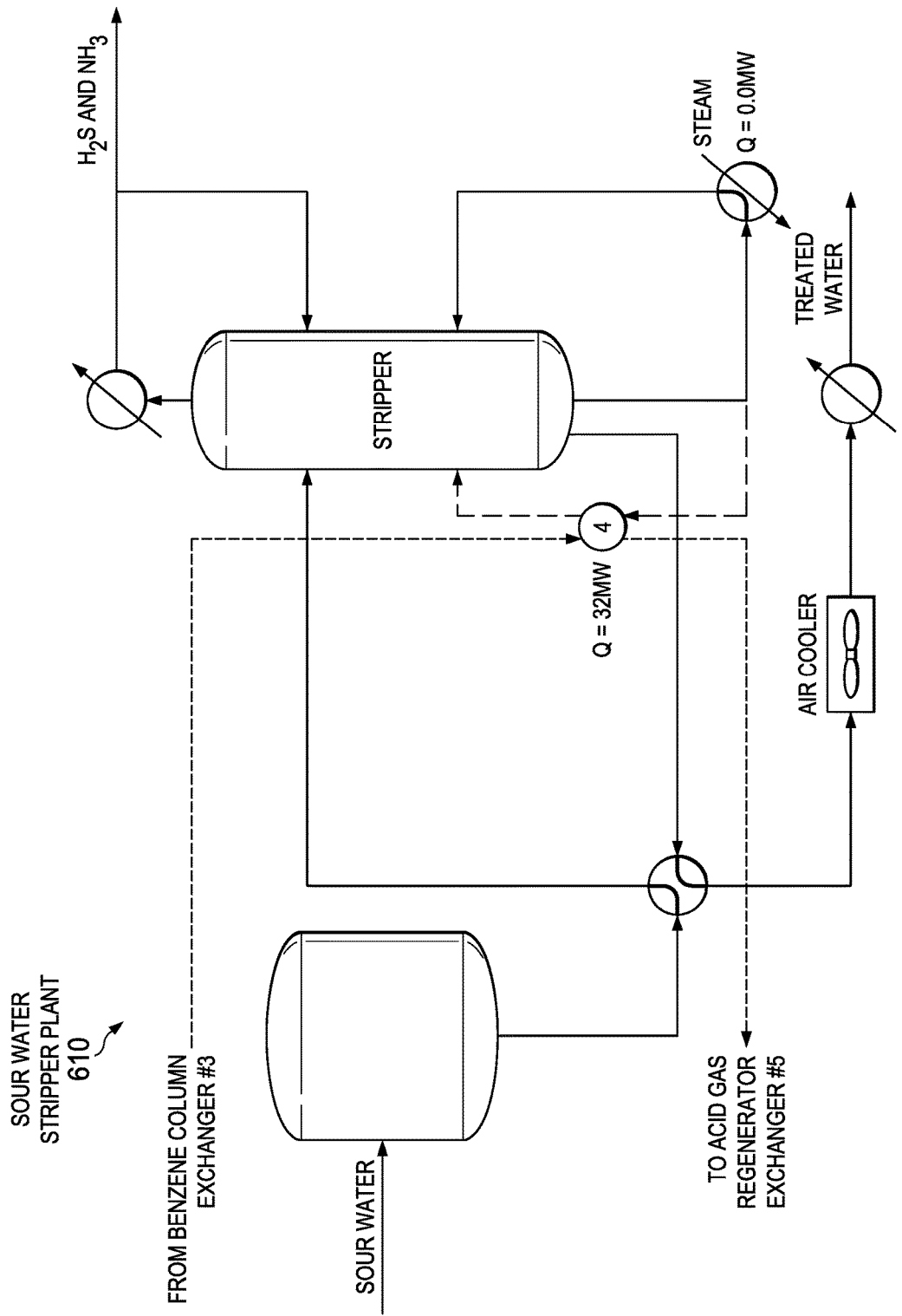
Figure 1A:
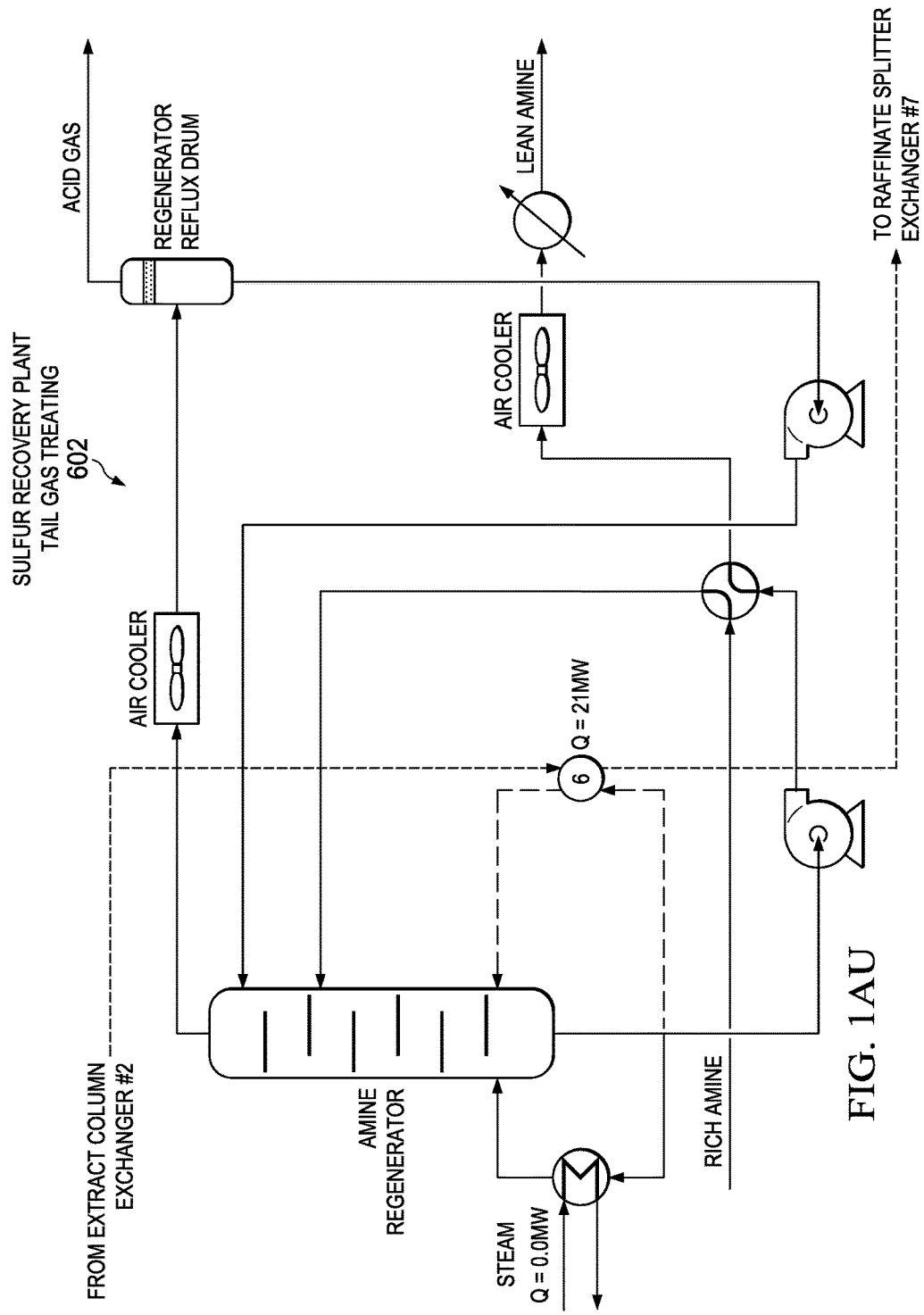
Figure 1A:
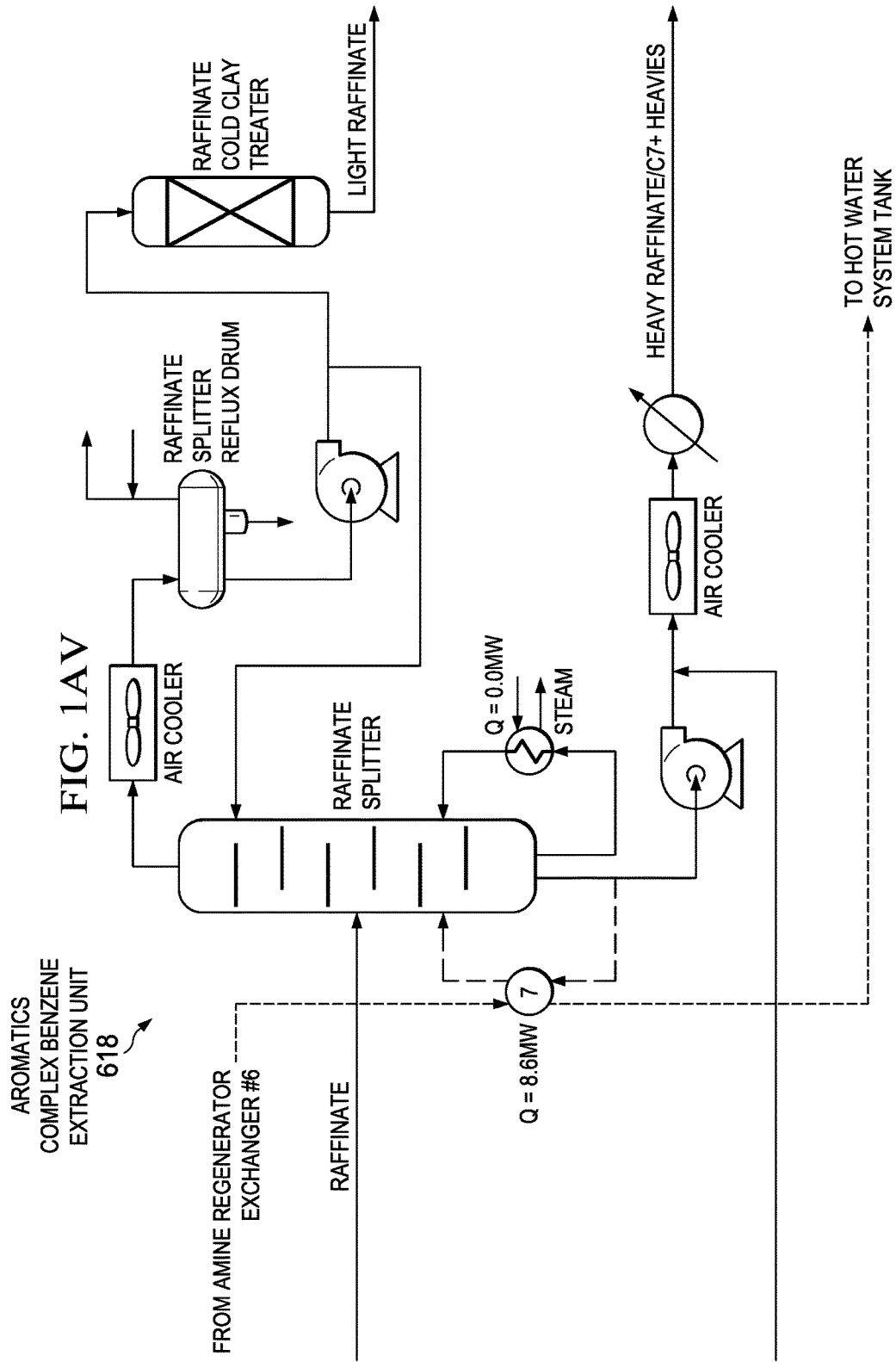
Figure 1A:
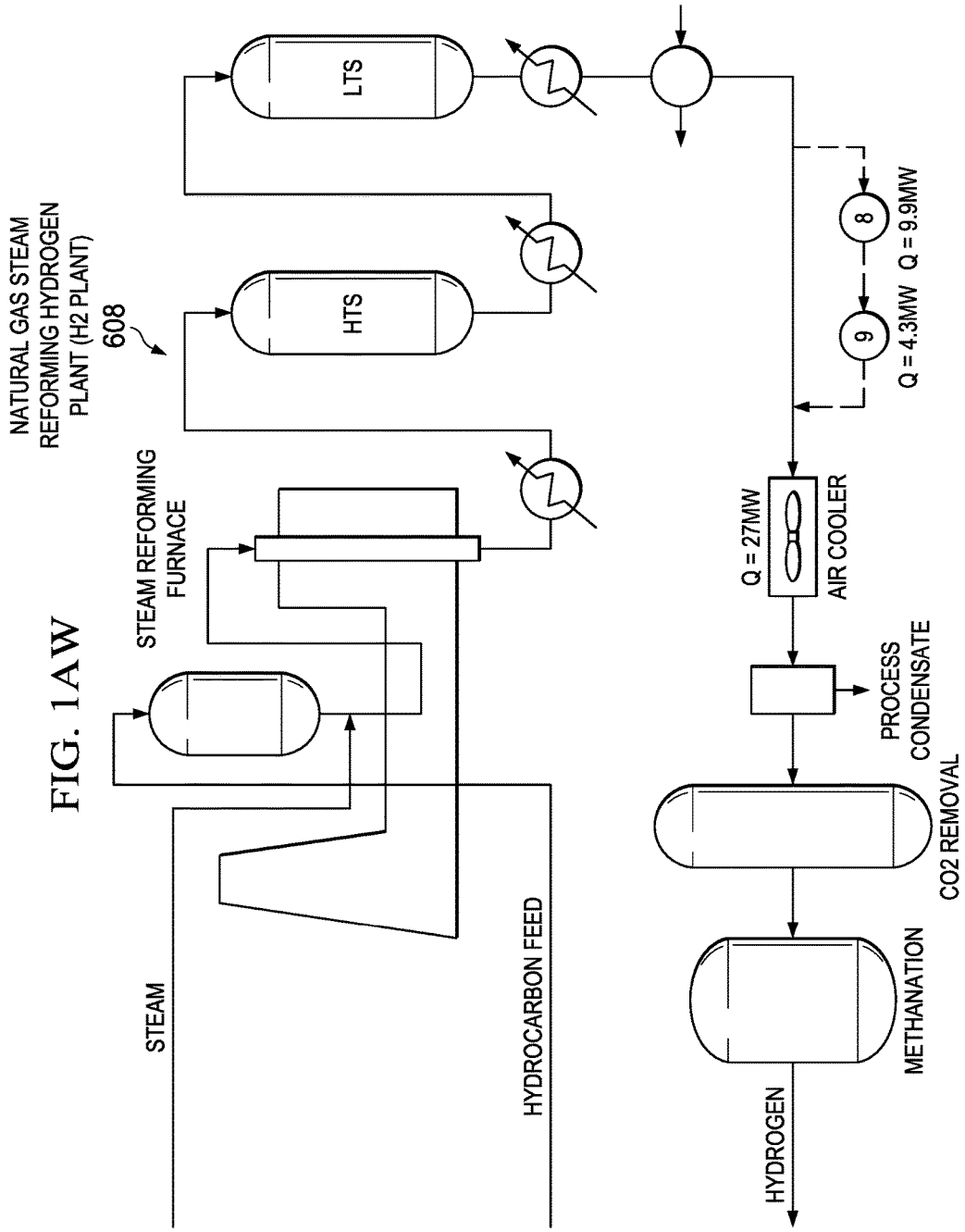
Figure 1A:
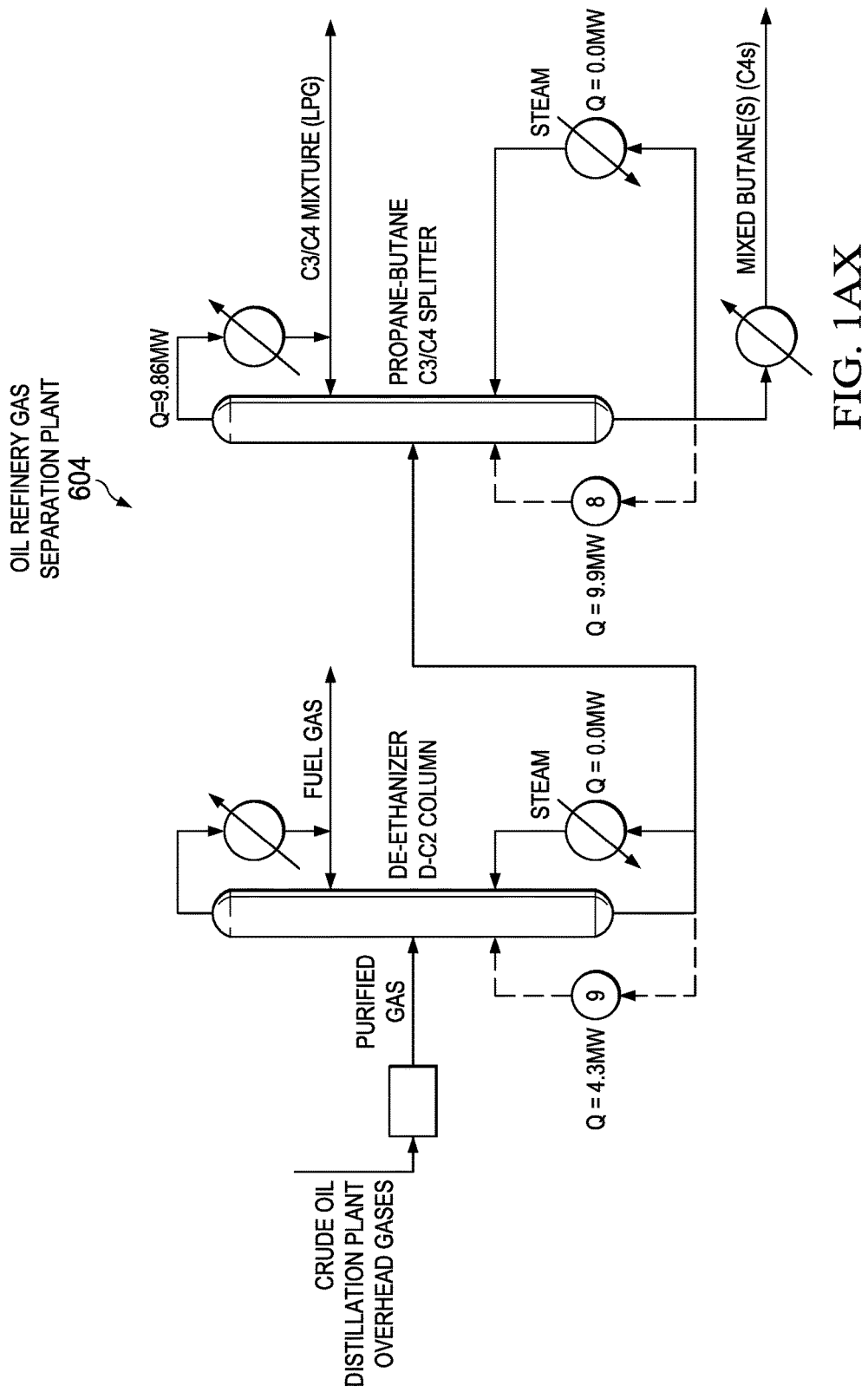
Figure 1A:
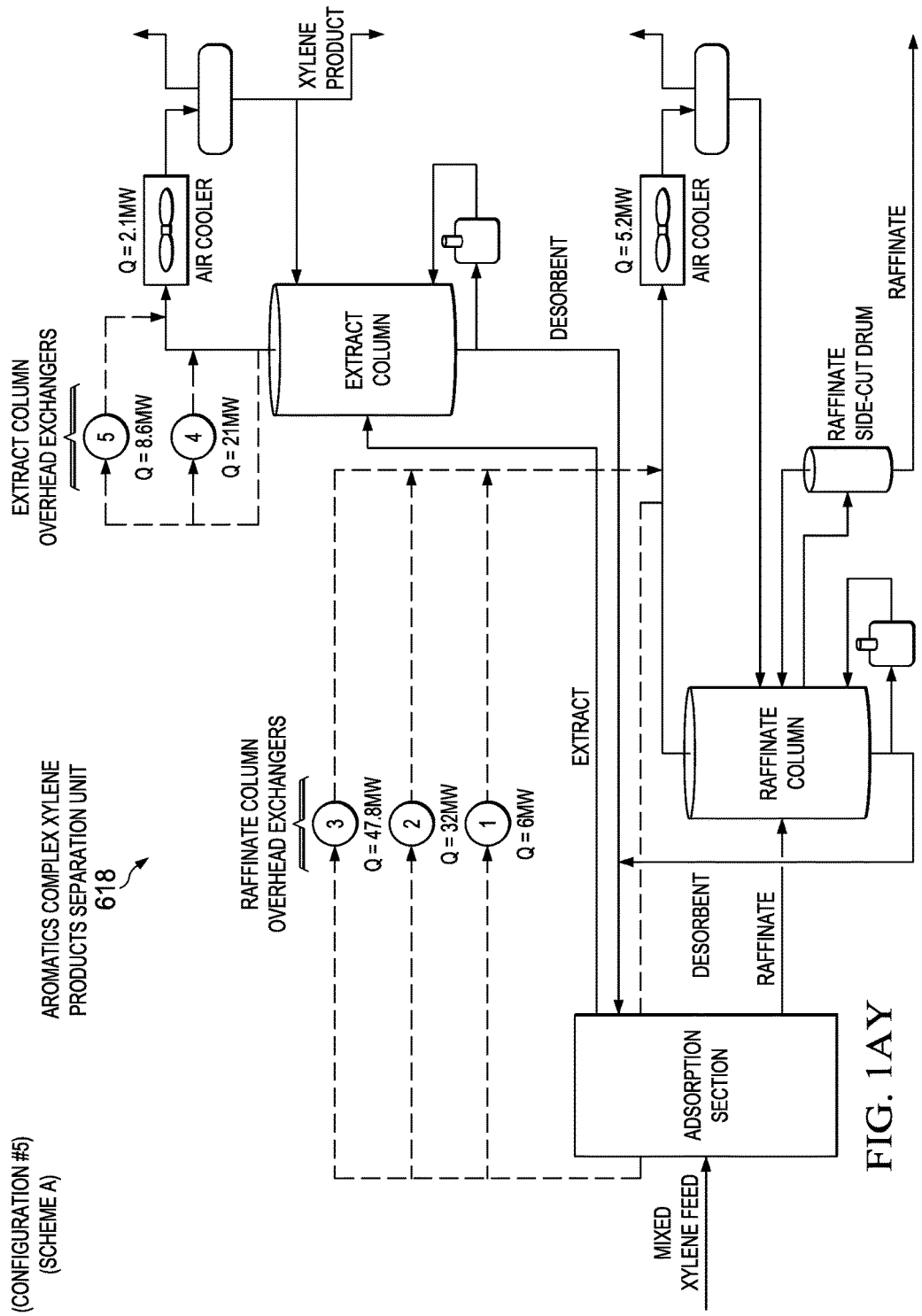
Figure 1A:
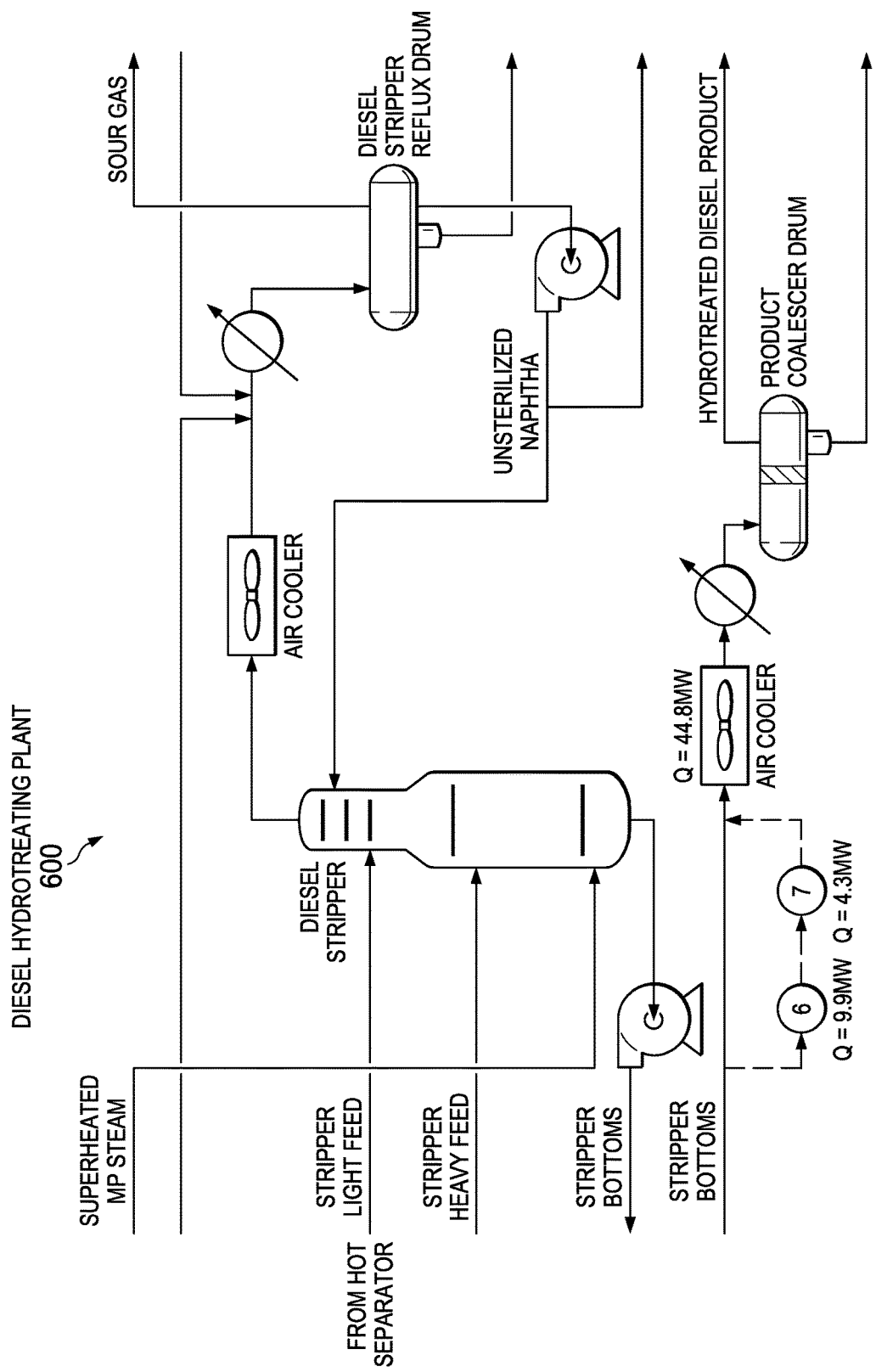
Figure 1B:
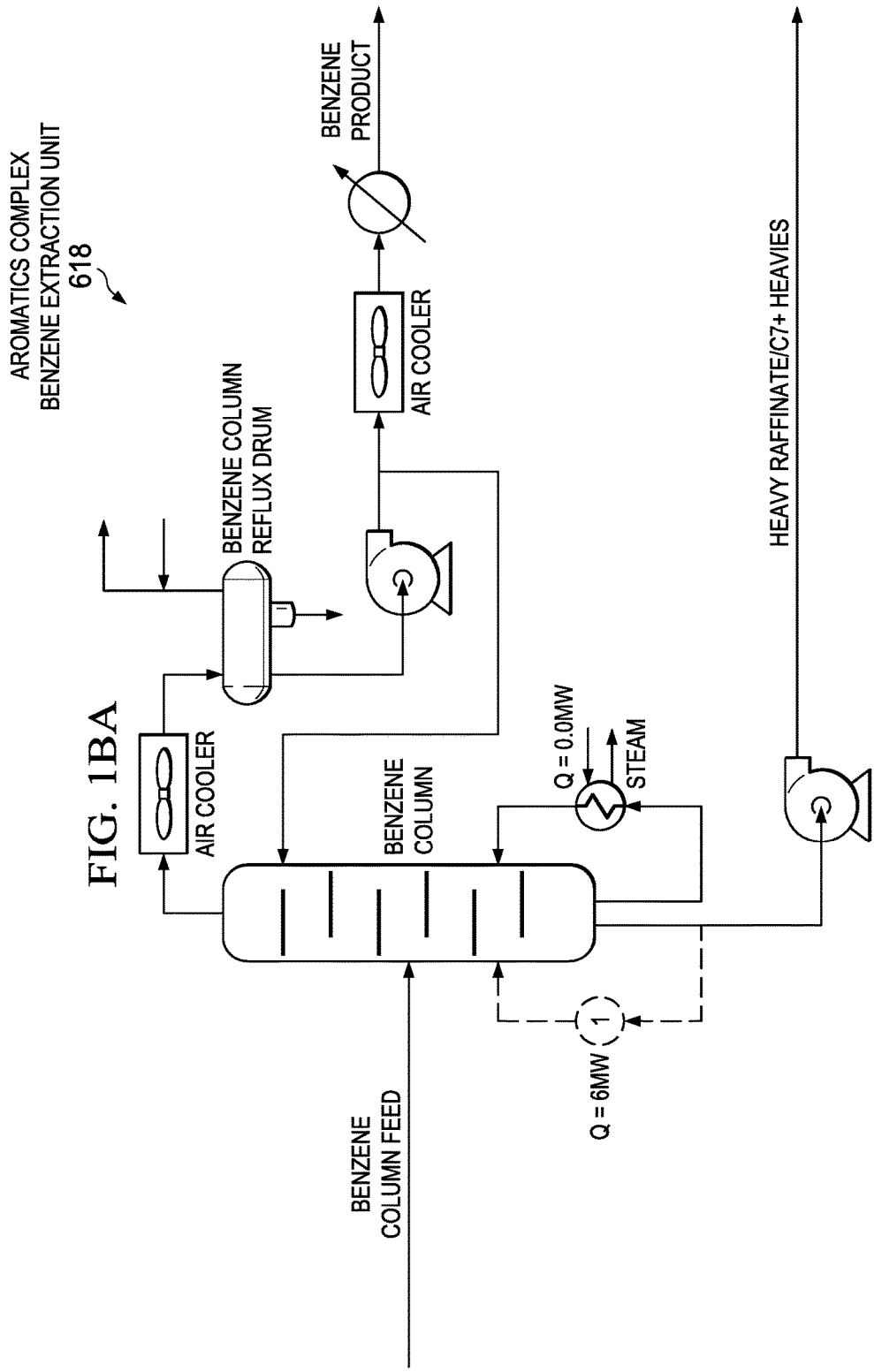
Figure 1B:
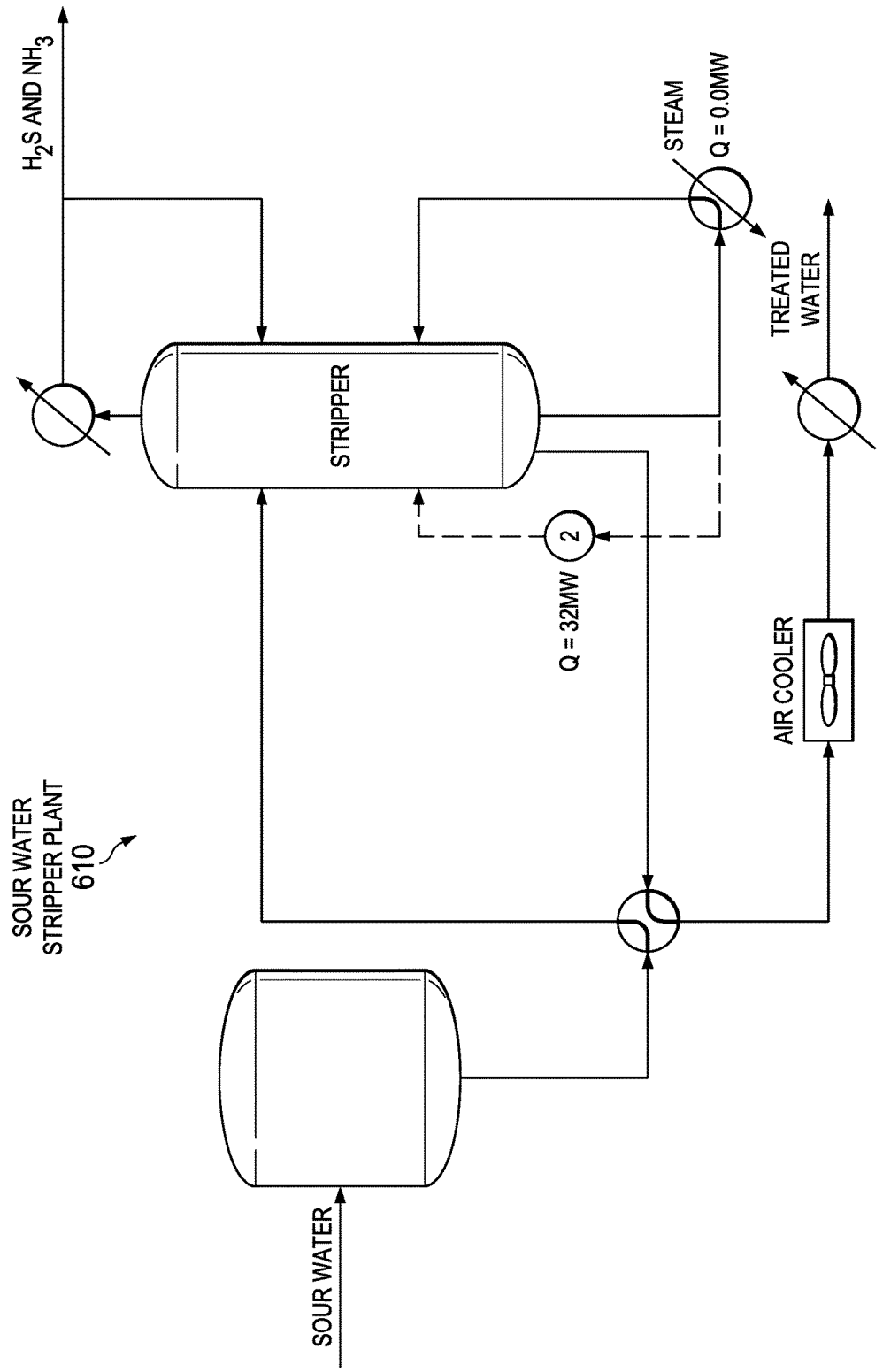
Figure 1B:
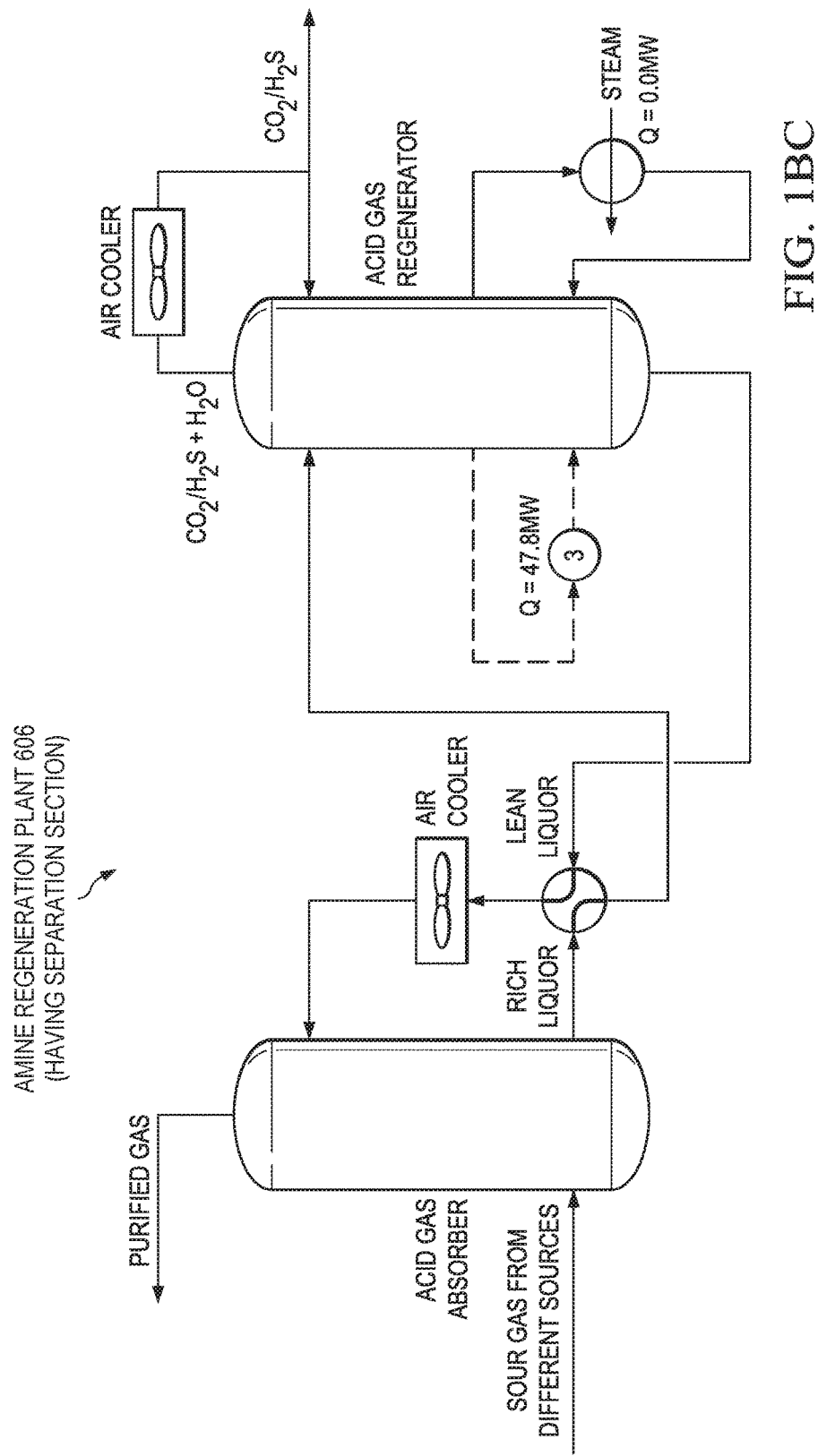
Figure 1B:
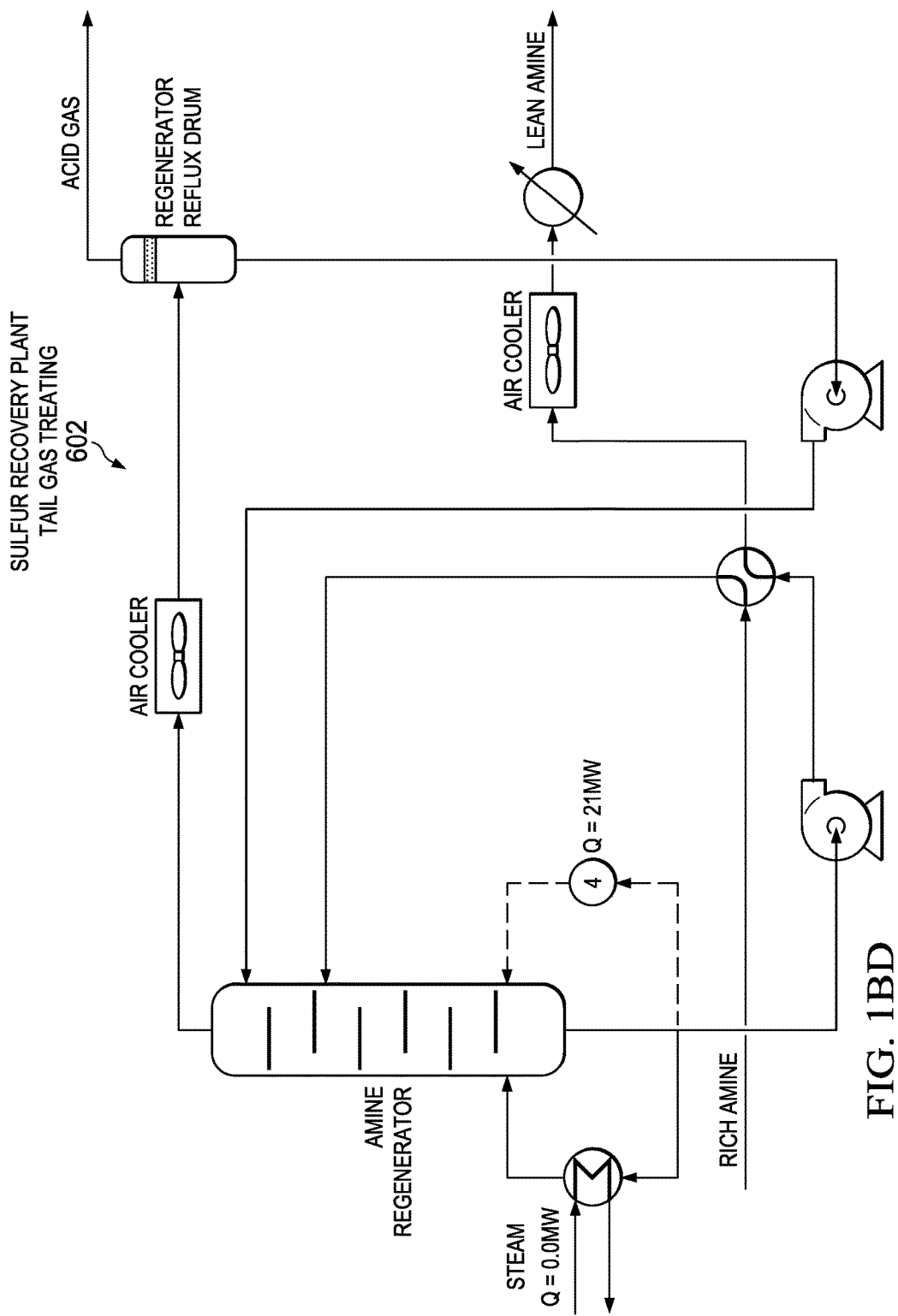
Figure 1B:
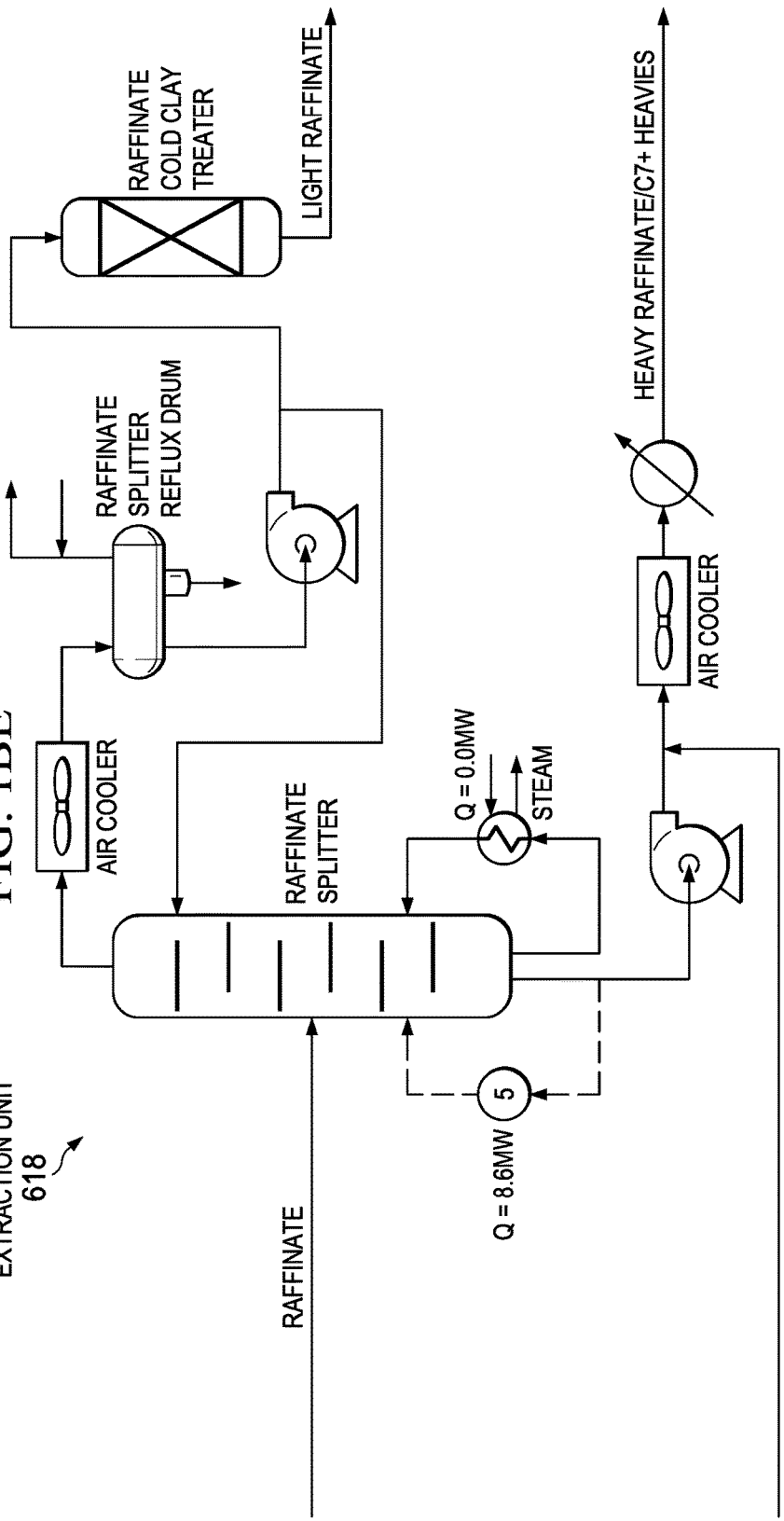
Figure 1B:
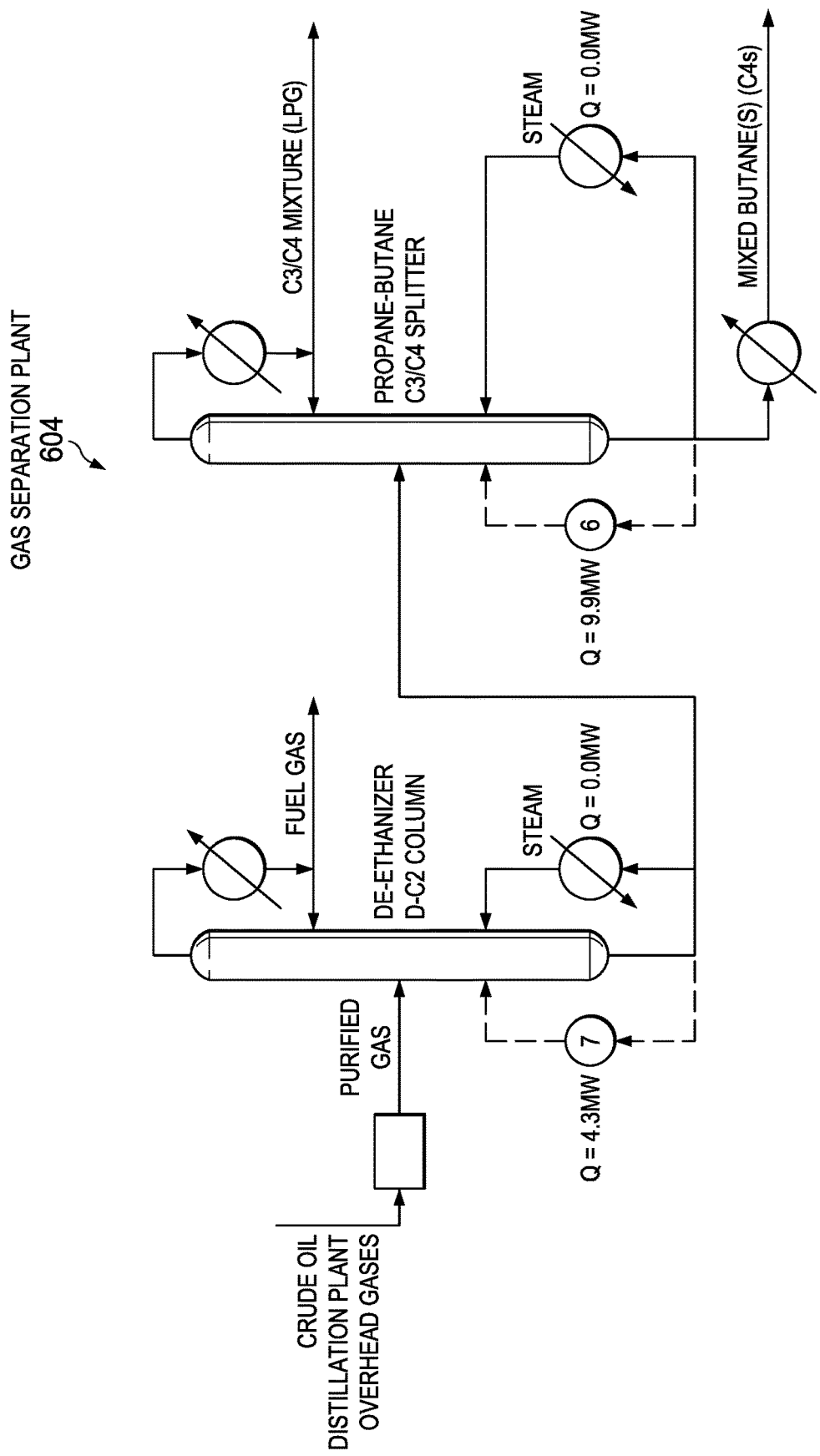
Figure 1B:
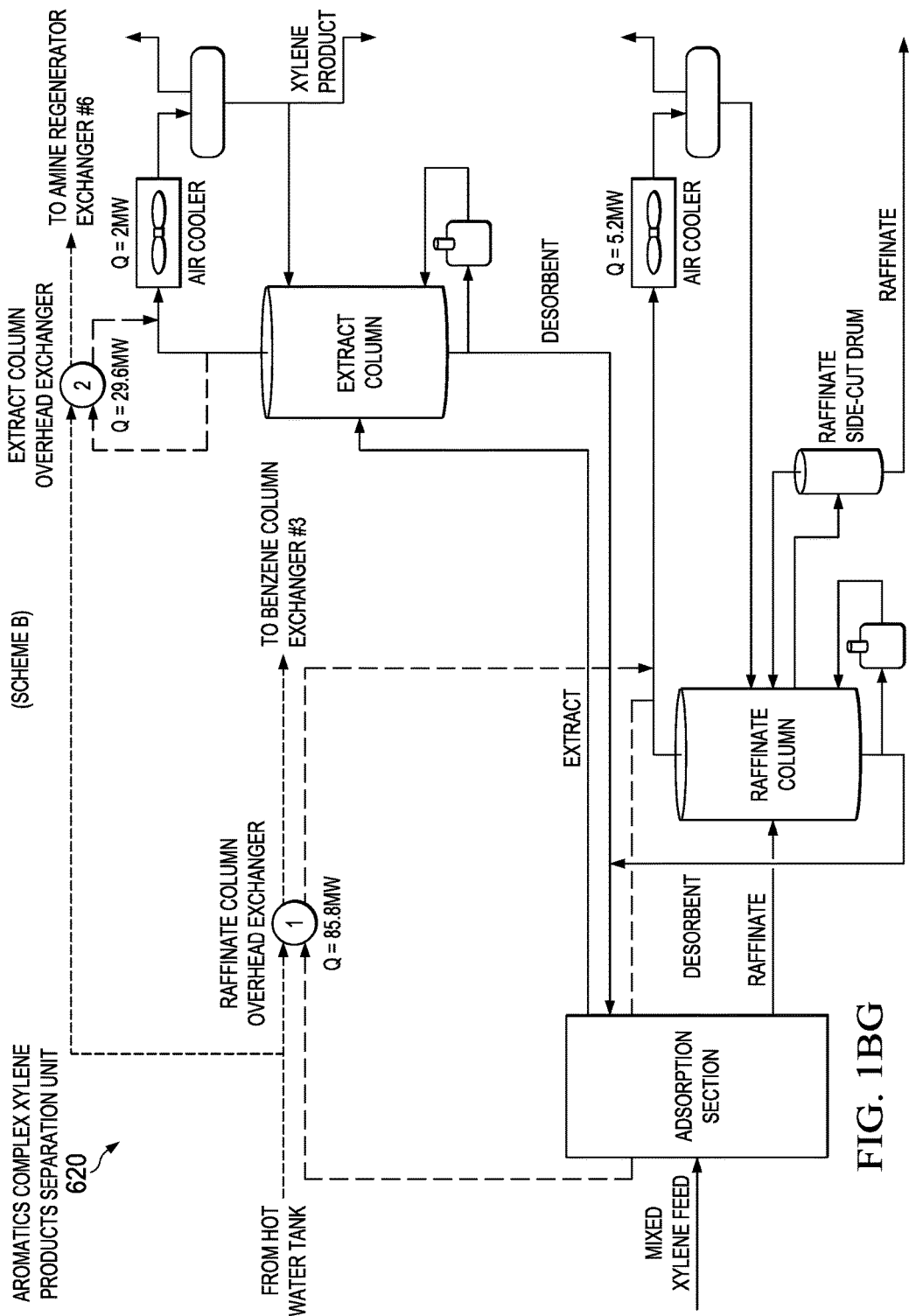
Figure 1B:
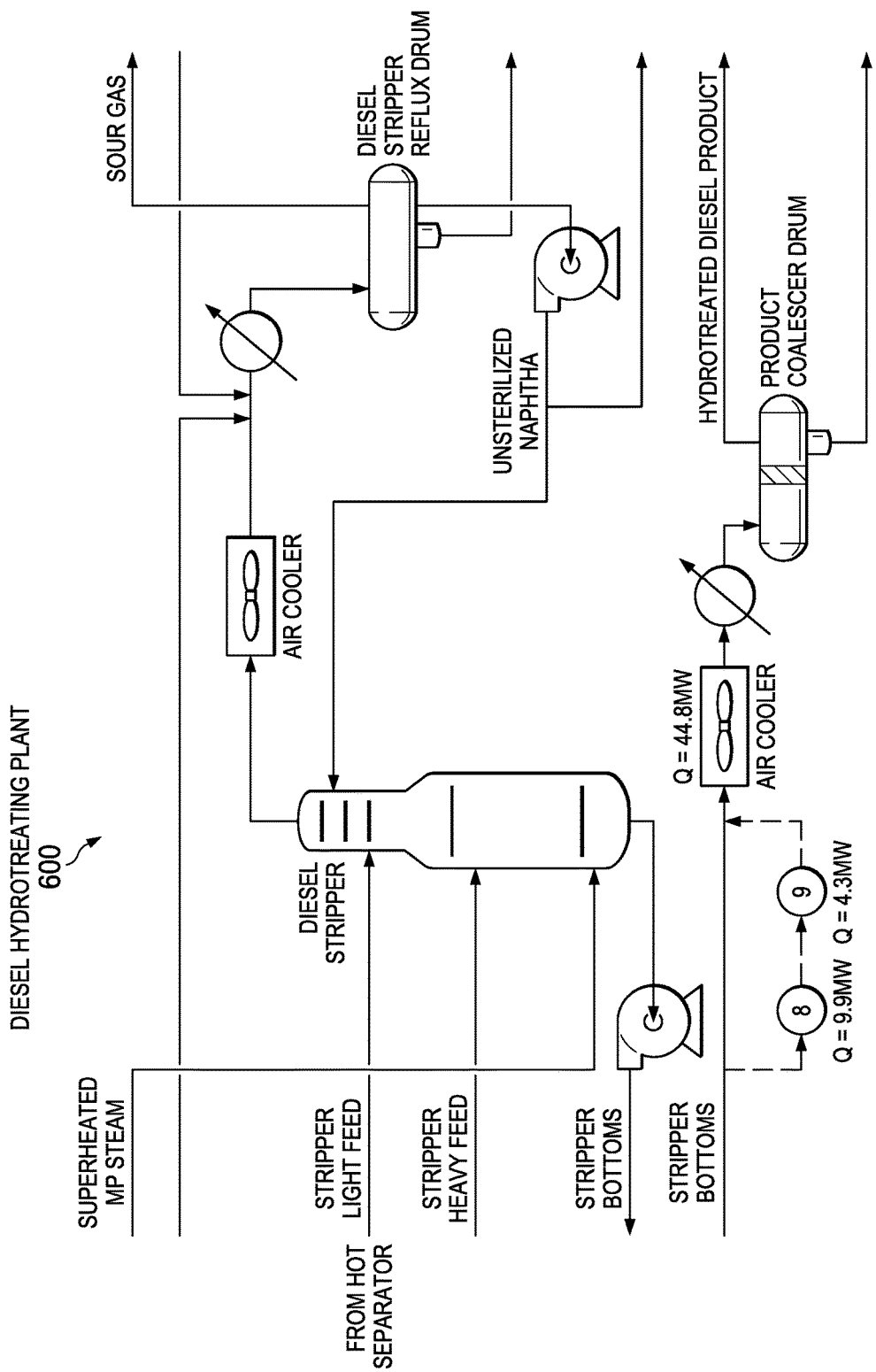
Figure 1B:
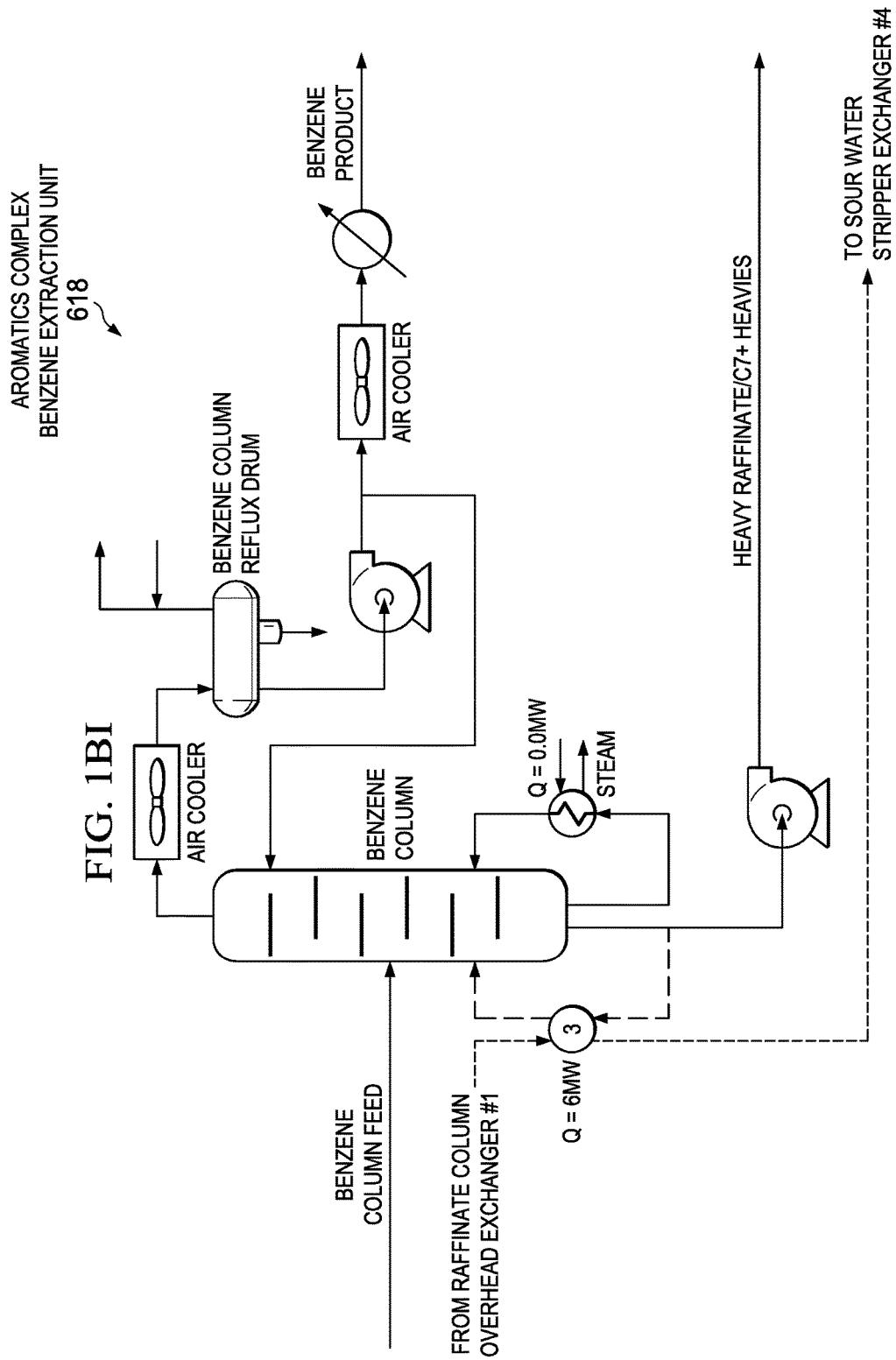
Figure 1B:
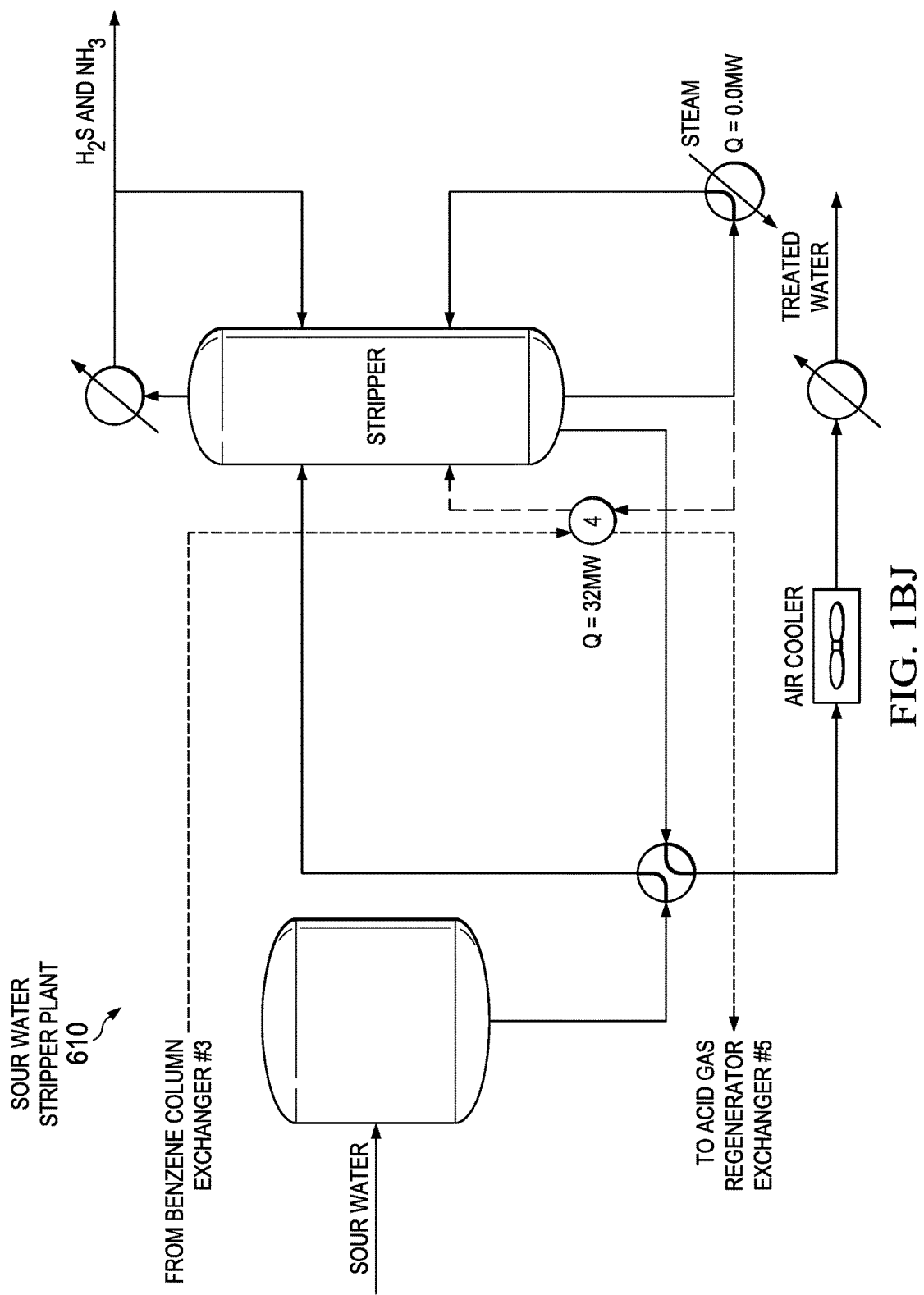
Figure 1B:
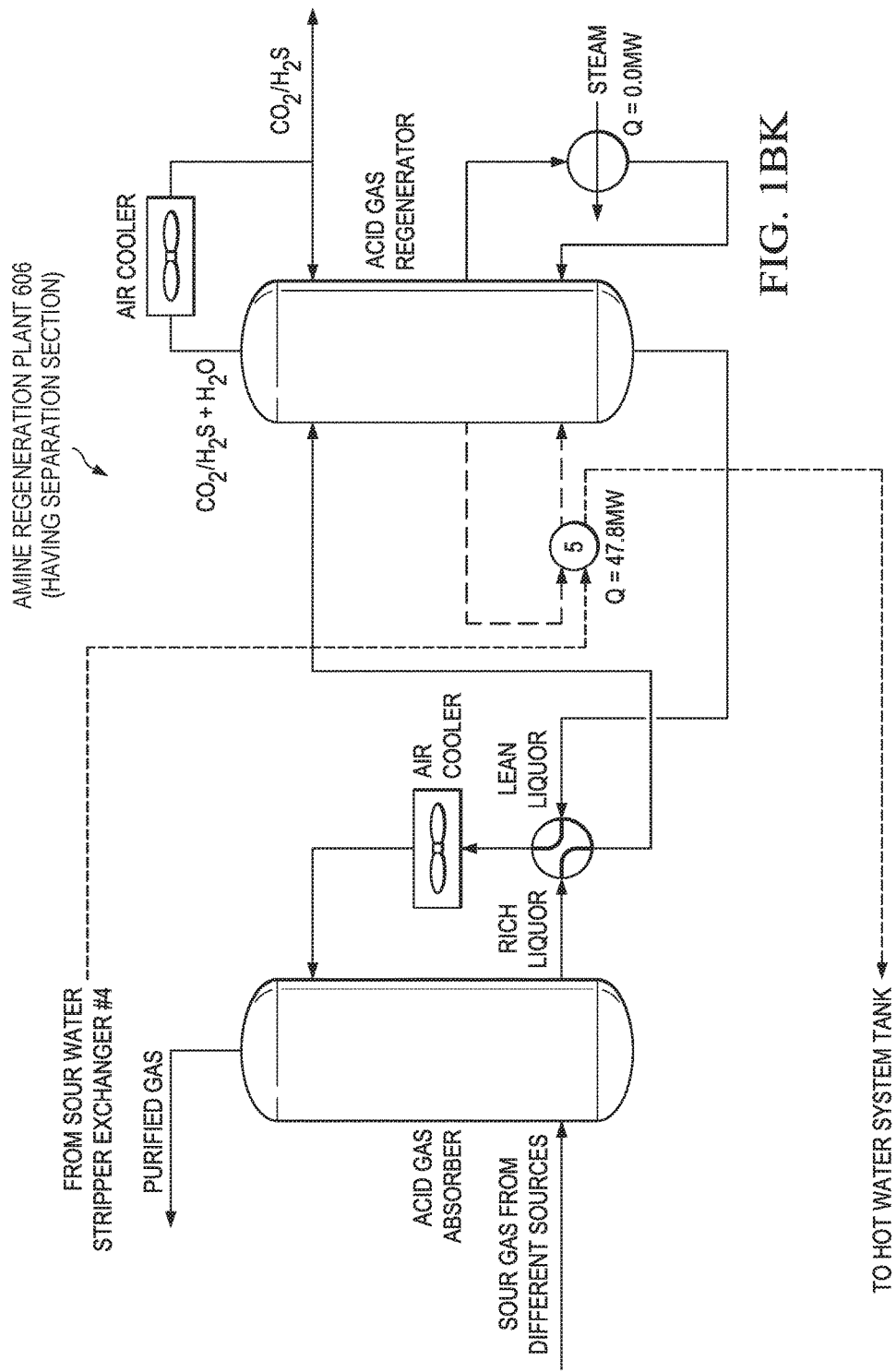
Figure 1B:
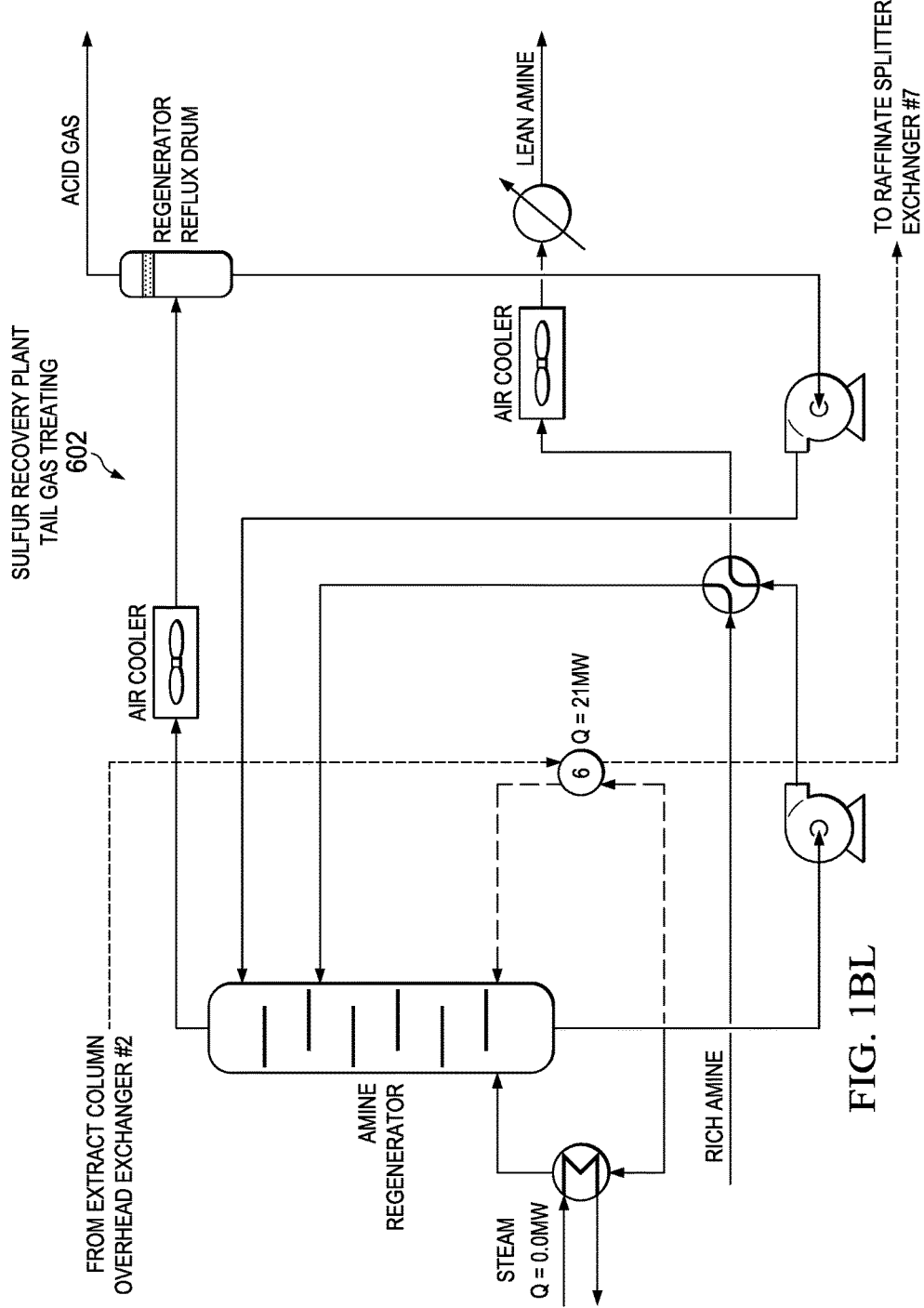
Figure 1B:
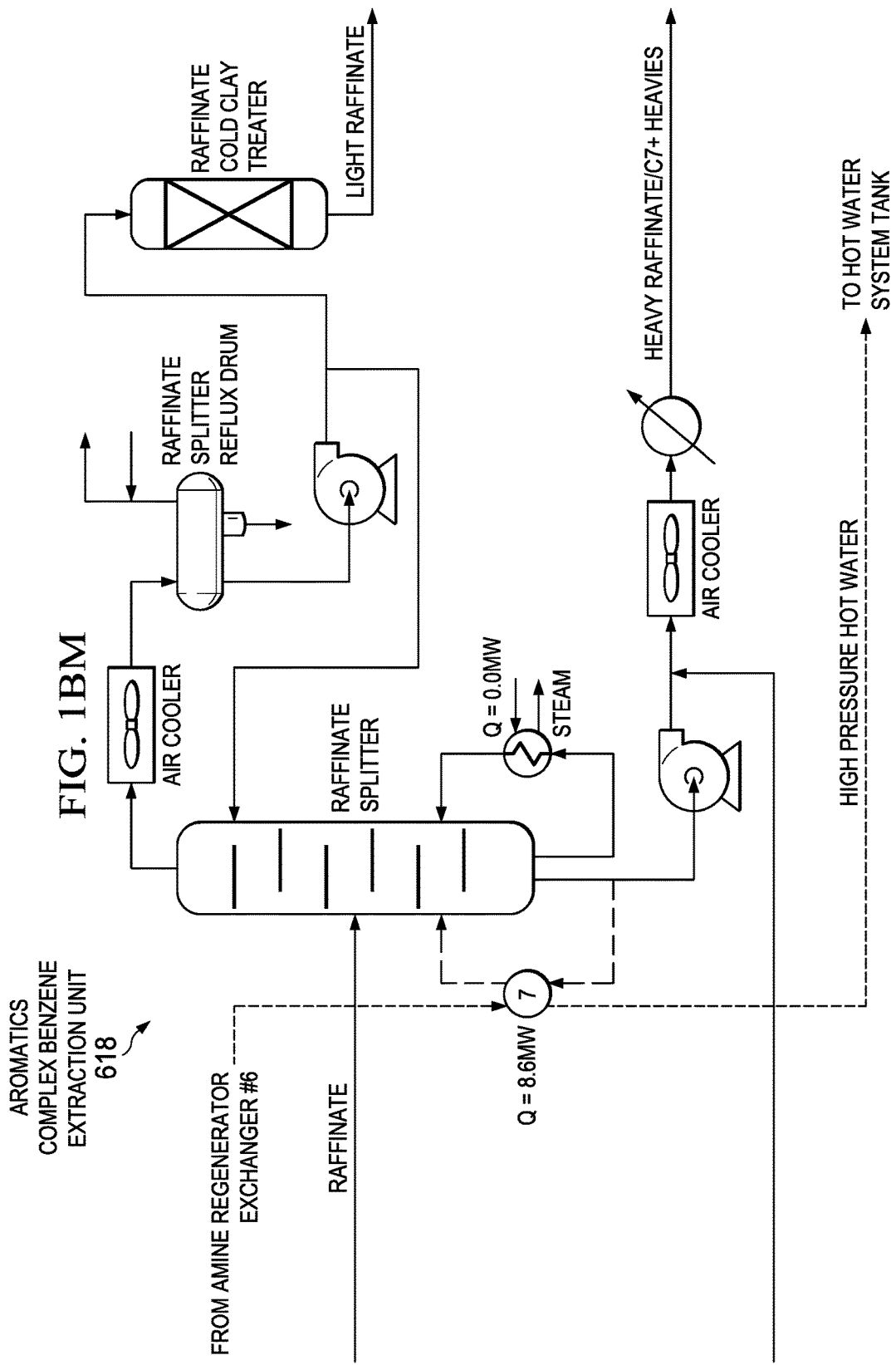
Figure 1B:
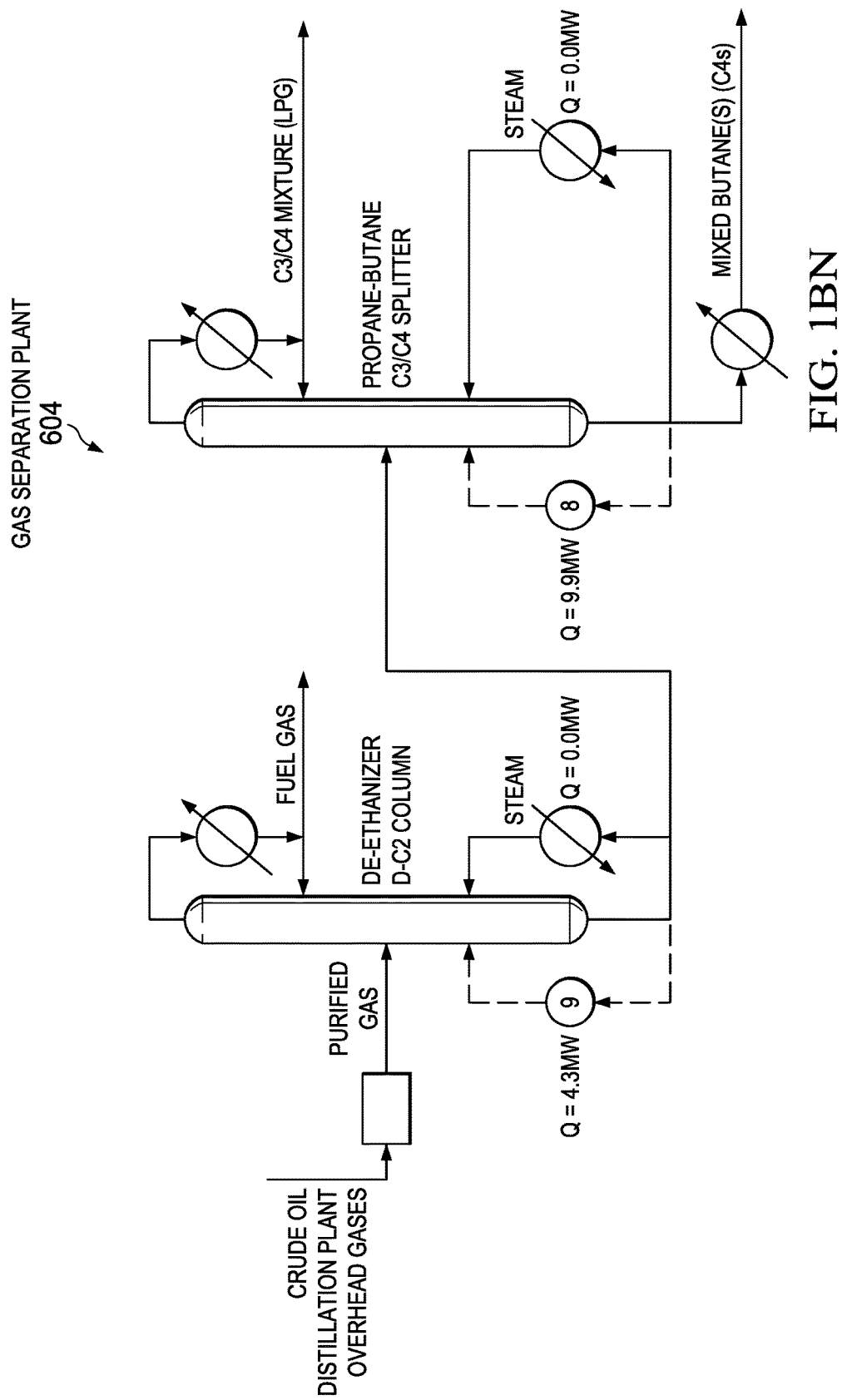

FIG. 1Z shows the sulfur recovery plant 602 in the crude oil refinery facility. The heated amine regenerator bottoms stream can then be flowed to the sulfur recovery plant 602. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AB shows the gas separation plant 604 in the crude oil refinery facility. The heated C3/C4 splitter bottoms stream can be flowed to the gas separation plant 604. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In addition, the heated de-ethanizer bottom stream can also be flowed to the gas separation plant 604. As shown in FIG. 1AB, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat directly from the aromatics complex can result in decreasing or eliminating the heat energy to heat the gas separation plant, an amine regeneration plant, a sulfur recovery plant, an aromatics plant or combinations of them such as by about 98 MW.

Configuration 3—Scheme B

In some implementations, the multiple first streams in multiple first plants in the crude oil refining facility can be indirectly heated using a second stream in a second plant, and multiple third streams in multiple third plants in the crude oil refining facility can be indirectly heated using a fourth stream in the second plant. In some implementations, the multiple first plants and the multiple third plants share a common plant. In some instances, multiple first plants include the amine regeneration plant, the sulfur recovery plant, and the aromatics complex benzene extraction unit and, and the multiple first streams include a benzene column bottoms, an acid gas regenerator bottoms and an amine regenerator bottoms. The second plant include the aromatics complex, which can include an aromatics complex xylene products separation unit, the second stream can include a raffinate column overheads stream, and the fourth stream can include an extract column overheads stream. The multiple third plants can include the aromatics complex benzene extraction unit and the gas separation plant, and the multiple third streams include the de-ethanizer bottoms, a C3/C4 splitter bottoms streams and a raffinate splitter bottoms. In some instances, the shared common plant can be an aromatics complex benzene extraction unit.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 620. The buffer fluid can be flowed into the plant as a single stream and split into multiple streams or it can be flowed into the plant as multiple streams. FIG. 1AC shows the buffer fluid is split into a first buffer fluid stream and a second buffer fluid stream.

FIG. 1AC shows an aromatics complex xylene products separation unit 620 in a crude oil refinery facility. A buffer fluid can be flowed from a buffer fluid tank to an aromatics plant xylene products separation unit 620. The first buffer fluid stream can be heated using a raffinate column overhead stream in a first heat exchanger with a thermal duty that can range between about 70 MW and 80 MW (for example, 74.7 MW). The buffer fluid absorbs heat that would have otherwise been discharged to the environment. The raffinate column overheads stream is returned to the xylene products separation unit 620 for further processing.

Also as shown in FIG. 1AC, a second buffer fluid stream can be heated using an extract column overheads stream in the aromatics plant xylene products separation unit 620 in a second heat exchanger with a thermal duty that can range between about 20 MW and 30 MW (for example, 22.9 MW). The buffer fluid absorbs heat that would have otherwise been discharged to the environment. The extract column overheads stream is returned to the xylene products separation unit 620 for further processing.

The heated buffer fluid streams can be directed to a collection header (or in some embodiments, a heated or insulated buffer fluid tank or storage unit that can hold heated collected buffer fluid for a period before use) and then can be flowed to the amine regeneration plant 606, the sulfur recovery plant 602, the aromatics complex benzene extraction unit 618, and the gas separation plant 604, and combinations thereof. In some instances, the heated buffer fluid streams are maintained as a first heated buffer fluid stream and a second heated buffer fluid stream. In such instances, the first and second heated buffer fluid streams are not recombined in a collection header or fluid tank until they have transferred the thermal energy obtained in the second plant into the multiple streams of the multiple first and third plants, respectively.

FIG. 1AD shows the aromatics complex benzene extraction unit 618 in a crude oil refinery facility. The first heated buffer fluid stream is flowed to the benzene extraction unit 618. A benzene column bottoms stream is heated using the first heated buffer fluid stream in a third heat exchanger with a thermal duty that can range between about 1 MW and 10 MW (for example, 6 MW). The third heat exchanger is coupled to, in series with and is downstream of the first heat exchanger relative to the buffer fluid flow. As shown in FIG. 1AD, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AE shows the sulfur recovery plant 602 in a crude oil refinery facility. The first heated buffer fluid branch is flowed to the sulfur recovery plant 602. An amine regenerator bottoms stream is heated using the first heated buffer fluid stream in a fourth heat exchanger with a thermal duty that can range between about 15 MW and 25 MW (for example, 21 MW). The fourth heat exchanger is coupled to, in series with and is downstream of the first heat exchanger relative to flow of the buffer fluid. As shown in FIG. 1AE, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AF shows the amine regeneration plant 606 in a crude oil refinery facility. The first heated buffer fluid stream is flowed to an amine regeneration plant 606. An acid gas regenerator bottoms stream is heated using the first heated buffer fluid stream in a fifth heat exchanger with a thermal duty that can range between about 45 MW and 55 MW (for example, 47.8 MW). The fifth heat exchanger is coupled to, in series with and is downstream of the first heat exchanger relative to the buffer fluid flow. As shown in FIG. 1AF, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The first heated buffer fluid stream exiting the fifth heat exchanger is flowed to the buffer fluid tank for reuse. The third, fourth and fifth heat exchangers are coupled to one another in series relative to the flow of the heated buffer fluid.

In some implementations, the first heated buffer fluid stream can be flowed in series through the different plants. For example, the first heated buffer fluid can be flowed first to the amine regeneration plant, then to the sulfur recovery plant and then to the aromatics complex benzene extraction unit. The first heated buffer fluid exiting the final exchanger(s) in the series can then be flowed to the buffer fluid tank. The buffer fluid from the buffer fluid tank can then be flowed to the different plants to restart the waste heat recovery and reuse cycle.

FIG. 1AG also shows the aromatics complex benzene extraction unit 618 in a crude oil refinery facility. The second heated buffer fluid stream is flowed to the aromatics complex benzene extraction unit 618. A raffinate splitter bottoms stream can be heated using the second heated buffer fluid stream in a sixth heat exchanger with a thermal duty that can range between about 5 MW and 15 MW (for example, 8.6 MW). The sixth heat exchanger is coupled to, in series with and is downstream of the second heat exchanger relative to the buffer fluid flow. The sixth and the set of the third, fourth, and fifth heat exchangers are coupled in parallel to one another relative to the flow of buffer fluid. As shown in FIG. 1AG, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

FIG. 1AH shows the gas separation plant 604 in a crude oil refinery facility. The second heated buffer fluid stream is flowed to the gas separation plant 604. A C3/C4 splitter bottoms stream is heated using the second heated buffer fluid stream in a seventh heat exchanger with a thermal duty that can range between about 5 MW and 15 MW (for example, 9.9 MW). The seventh heat exchanger is coupled to, in series with and is downstream of the second heat exchanger relative to the buffer fluid flow. As shown in FIG. 1AH, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

Also as shown in FIG. 1AH, A de-ethanizer bottoms stream is heated using the second heated buffer fluid stream in an eighth heat exchanger with a thermal duty that can range between about 1 MW and 10 MW (for example, 4.3 MW). The eighth heat exchanger is coupled to, in series with and is downstream of the second heat exchanger relative to the buffer fluid flow. As shown in FIG. 1AH, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

The second heated buffer fluid stream exiting the eighth heat exchanger is flowed to the buffer fluid tank for reuse. The sixth, seventh and eighth heat exchangers are coupled to one another in series relative to the flow of the heated buffer fluid. The set of the sixth, seventh and eighth heat exchangers and the set of the third, fourth, and fifth heat exchangers are coupled in parallel to one another relative to the flow of the buffer fluid.

In some implementations, the second heated buffer fluid stream can be flowed in series through the different plants. For example, the second heated buffer fluid can be flowed first to the gas separation plant and then the aromatics complex benzene extraction unit. As well, the order of second heated buffer fluid intra-plant can be different, for example, the heated buffer fluid can flow first through the de-ethanizer bottoms exchanger and then the C3/C4 splitter bottoms exchanger. The second heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly using separately heated and routed buffer fluid streams from the aromatics complex xylene products separation unit can result in decreasing or eliminating the heat energy for heating the sulfur recovery plant, the aromatics complex benzene extraction plant, the amine regeneration plant, the sour water stripper plant, the gas separation plant or combinations of them such as by about 98 MW.

Configuration 4

FIGS. 1AI-1AX illustrate configurations and related scheme details for thermally integrating different refining plants in the crude oil refining facility. The thermal integration described in these configurations and illustrated in FIGS. 1AI-1AX can reduce the crude oil refining facility's energy consumption (for example, heating and cooling utilities). For example, a reduction in energy consumption by about 130 MW (for example, 129.7 MW) can translate to at least about 20% (for example, 19.95%), of the energy consumption in the crude oil refining facility. In certain schemes, a process stream from one refining plant can be used to directly heat another process stream from another, different refining plant. In certain configurations, heat exchange between process streams can be implemented using an intermediate buffer fluid, for example, water, oil, or other buffer fluid.

Configuration 4—Scheme A

In some implementations, multiple first streams in the multiple first plants can be directly heated using a second stream from a second plant, multiple third streams in the multiple third plants can be directly heated using a fourth stream from a second plant, and multiple fifth streams in a fifth plant can be directly heated using a sixth stream from a sixth plant. In some instances, the multiple first plants and the multiple third plants share a common plant. In some implementations, the multiple first plants in the crude oil refinery can include a sour water stripper plant, an amine regeneration plant, and an aromatics complex benzene extraction plant, and the multiple first streams can include a benzene column bottoms, a sour water stripper bottoms and an acid gas regenerator bottoms streams. The second plant can include an aromatics complex, which can include an aromatics complex xylene products separation unit, and the second stream can include a raffinate column overheads, and the fourth stream can include an extract column overheads streams. In some implementations, the multiple third plants in the crude oil refinery can include a sulfur recovery plant and an aromatics complex benzene extraction plant, and the multiple third streams can include an amine regenerator bottoms and a raffinate splitter bottoms streams. In some instances, the shared common plant can be an aromatics complex benzene extraction unit. The fifth plant can include a gas separations plant, and the multiple fifth plant streams can include a de-ethanizer bottoms and a C3/C4 splitter bottoms streams. The sixth plant can include a natural gas steam reforming hydrogen plant, and the fourth stream can include a low temperature shift (LTS) converter product stream.

FIG. 1AI shows an aromatics complex xylene products separation unit 620 in a crude oil refinery facility that includes a raffinate column overheads stream. The raffinate overheads column stream can be flowed in the plant as a single stream and split into multiple streams or it can be flowed into the plant as multiple streams to facilitate heat recovery. A first raffinate column overheads stream can directly heat a benzene column bottoms stream in a first heat exchanger with a thermal duty that can range between about 1 MW to 10 MW (for example, 6 MW). A second raffinate column overheads stream can directly heat a sour water stripper bottom stream in the sour water stripper plant 610 in a second heat exchanger with a thermal duty that can range between about 25 MW and 35 MW (for example, 32 MW). A third raffinate column overheads stream can directly heat an acid gas regenerator bottom stream with a thermal duty that can range between about 45 MW and 55 MW (for example, 47.8 MW). In this manner, the first heat exchanger, the second heat exchanger, and the third heat exchanger can be coupled to each other in parallel relative to the flow of raffinate column overheads. The parallel set of raffinate column overhead exchangers transfer heat directly to other process streams that would have otherwise been discharged to the environment. In an alternative embodiment, the cooling requirement of the raffinate column overheads stream can be 0 MW because the alternative flow path disclosed in this configuration may satisfy the entire cooling requirement for the raffinate column overheads stream for the operation of the raffinate column. The raffinate column overheads streams are recombined and returned to the aromatics plant xylene products separation unit 620 for further processing.

The aromatics complex xylene products separation unit 620 also includes an extract column overhead stream. The extract overheads column stream can be flowed in the plant as a single stream and split into multiple streams or it can be flowed into the plant as multiple streams to facilitate heat recovery. As shown in FIG. 1AI, the first extract column overhead stream can directly heat an amine regenerator bottoms stream in a fourth heat exchanger with a thermal duty that can range between about 15 MW and 25 MW (for example, 21 MW). The second extract column overheads stream can directly heat a raffinate splitter bottoms stream in a fifth heat exchanger with a thermal duty that can range between about 5 MW and 15 MW (for example, 8.6 MW). In this manner, the fourth and the fifth heat exchangers can be coupled to each other in parallel relative to the flow of extract column overheads. The parallel set of extract column overhead exchangers transfer heat directly to other process streams that would have otherwise been discharged to the environment. In an alternative embodiment, the cooling requirement of the extract column overheads stream can be 0 MW because the alternative flow path disclosed in this configuration may satisfy the entire cooling requirement for the extract column overheads stream for the operation of the extract column. The extract column overheads streams are recombined and returned to the aromatics plant xylene products separation unit 620 for further processing.

FIG. 1AK shows the aromatics complex benzene extraction unit 618 in the crude oil refinery facility. The heated benzene column bottoms stream can be flowed to the benzene extraction plant 618. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AO also shows the aromatics complex benzene extraction unit 618 in the crude oil refinery facility. The heated raffinate splitter column bottoms stream can also be flowed to the benzene extraction plant 618. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

FIG. 1AL also shows the sour water stripper plant 610 in the crude oil refinery facility. The heated sour water stripper bottoms cold stream can be flowed to the sour water stripper plant 610. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1AM shows the amine regeneration plant 606 in the crude oil refinery facility. The heated acid gas regenerator bottoms stream can be flowed to the amine regeneration plant 606. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

FIG. 1AN shows the amine regeneration plant 602 in the crude oil refinery facility. The heated amine regenerator bottoms stream can be flowed to the sulfur recovery plant 602. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AJ shows a natural gas steam reforming hydrogen plant 608 in a crude oil refinery facility that includes a low temperature shift (LTS) converter product stream. A natural gas steam reforming hydrogen plant 608 can be directly thermally integrated with a gas separation plant 606. A LTS converter product stream can directly heat a C3/C4 splitter bottoms stream in a sixth heat exchanger with a thermal duty that can range between about 1 MW and 10 MW (for example, 4.3 MW). Also, as shown in FIG. 1AJ, the LTS converter product stream can directly heat a de-ethanizer bottom stream in a seventh heat exchanger with a thermal duty that can range between about 5 MW and 15 MW (for example, 9.9 MW). The sixth heat exchanger is coupled to, in series with and is downstream of the seventh heat exchanger relative to the flow of LTS converter product stream. The series of LTS converter product heat exchangers transfer heat directly to other process streams that would have otherwise been discharged to the environment. The LTS converter product stream is returned to the natural gas steam reforming hydrogen plant 608 for further processing.

In some implementations, the order of LTS converter product stream intra-plant can be different, for example, the heated buffer fluid can flow first through the C3/C4 splitter bottoms exchanger and then the de-ethanizer bottoms exchanger. The LTS converter product stream exiting the final exchanger(s) in the series can then be flowed to the LTS converter product line.

FIG. 1AP shows the gas separation plant 604 in the crude oil refinery facility. The heated C3/C4 splitter bottoms stream can be flowed to the gas separation plant 604. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In addition, the heated de-ethanizer bottoms stream can also be flowed to the gas separation plant 604. As shown in FIG. 1AP, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat separately and directly from both an aromatics complex xylene products separation unit and a natural gas steam reforming hydrogen plant can result in decreasing or eliminating the heat energy to heat the gas separation plant stream, a sour water stripper plant, an amine regeneration plant, a sulfur recovery plant, an aromatics complex benzene extraction unit or combinations of them such as by about 130 MW.

Configuration 4—Scheme B

In some implementations, multiple first streams in the multiple first plants can be indirectly heated using a second stream from a second plant, multiple third streams in the multiple third plants can be indirectly heated using a fourth stream from a second plant, and multiple fifth streams in a fifth plant can be directly heated using a sixth stream from a sixth plant. In some instances, the multiple first plants and the multiple third plants share a common plant. In some implementations, the multiple first plants in the crude oil refinery can include a sour water stripper plant, a sulfur recovery plant, an amine regeneration plant, and an aromatics complex benzene extraction plant, and the multiple first streams can include a benzene column bottoms, a sour water stripper bottoms, an acid gas regenerator bottoms, an amine regenerator bottoms and a raffinate splitter bottoms streams. The second plant can include an aromatics complex, which can include an aromatics complex xylene products separation unit, the second stream can include a raffinate column overheads stream, and the fourth stream can include an extract column overheads stream. In some implementations, the multiple third plants in the crude oil refinery can include a sulfur recovery plant and an aromatics complex benzene extraction plant, and the multiple third streams can include an amine regenerator bottoms and a raffinate splitter bottoms streams. In some instances, the shared common plant can be an aromatics complex benzene extraction unit. The fifth plant can include a gas separations plant, and the multiple fifth plant streams can include a de-ethanizer bottoms and a C3/C4 splitter bottoms streams. The sixth plant can include a natural gas steam reforming hydrogen plant, and the sixth stream can include a low temperature shift (LTS) converter product stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 620. The buffer fluid can be flowed into the plant as a single stream and split into multiple streams or it can be flowed into the plant as multiple streams. FIG. 1AQ shows the buffer fluid is split into a first buffer fluid stream and a second buffer fluid stream.

FIG. 1AQ shows an aromatics complex xylene products separation unit 620 in a crude oil refinery facility. A buffer fluid from a buffer fluid tank is flowed to an aromatics plant xylene products separation unit 620. The first buffer fluid stream can be heated using a raffinate column overheads stream in a first heat exchanger with a thermal duty that can range between about 80 MW and 90 MW (for example, 85.8 MW). The buffer fluid absorbs heat that would have otherwise been discharged to the environment. In an alternative embodiment, the cooling requirement of the raffinate column overheads stream can be 0 MW because the alternative flow path disclosed in this configuration may satisfy the entire cooling requirement for the raffinate column overheads stream for the operation of the raffinate column. The raffinate column overheads stream is returned to the xylene products separation unit 620 for further processing.

Also as shown in FIG. 1AQ, a second buffer fluid stream can be heated using an extract column overheads stream in the aromatics plant xylene products separation unit 620 in a second heat exchanger with a thermal duty that can range between about 25 MW and 35 MW (for example, 29.6 MW). The buffer fluid absorbs heat that would have otherwise been discharged to the environment. In an alternative embodiment, the cooling requirement of the extract column overheads stream can be 0 MW because the alternative flow path disclosed in this configuration may satisfy the entire cooling requirement for the extract column overheads stream for the operation of the extract column. The extract column overheads stream is returned to the xylene products separation unit 620 for further processing.

The heated buffer fluid streams can be directed to a collection header (or in some embodiments, a heated or insulated buffer fluid tank or storage unit that can hold heated collected buffer fluid for a period before use) and then can be flowed to the amine regeneration plant 606, the sulfur recovery plant 602, the aromatics complex benzene extraction unit 618 and the sour water stripper plant 610, and combinations thereof. In some instances, the heated buffer fluid streams are maintained as a first heated buffer fluid stream and a second heated buffer fluid stream. In such instances, the first and second heated buffer fluid streams are not recombined in a collection header or fluid tank until they have transferred the thermal energy obtained in the second plant into the multiple streams of the multiple first and third plants, respectively.

FIG. 1AR shows the aromatics complex benzene extraction unit 618 in a crude oil refinery facility. The first heated buffer fluid stream is flowed to the benzene extraction unit 618. A benzene column bottoms stream is heated using the first heated buffer fluid branch in a third heat exchanger with a thermal duty that can range between about 1 MW and 10 MW (for example, 6 MW). The third heat exchanger is coupled to, in series with and is downstream of the first heat exchanger relative to the buffer fluid flow. As shown in FIG. 1AR, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AS shows the sour water stripper plant 610 in a crude oil refinery facility. The first heated buffer fluid stream is flowed to the sour water stripper plant 610. A sour water stripper bottom stream is heated using the first heated buffer fluid branch in a fourth heat exchanger with a thermal duty that can range between about 25 MW and 35 MW (for example, 32 MW). The fourth heat exchanger is coupled to, in series with and is downstream of the first heat exchanger relative to the buffer fluid flow. As shown in FIG. 1AS, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1AT shows the amine regeneration plant 606 in a crude oil refinery facility. The first heated buffer fluid branch is flowed to an amine regeneration plant 606. An acid gas regenerator bottom stream is heated using the first heated buffer fluid branch in a fifth heat exchanger with a thermal duty that can range between about 45 MW and 55 MW (for example, 47.8 MW). The fifth heat exchanger is coupled to, in series with and is downstream of the first heat exchanger relative to the buffer fluid flow. As shown in FIG. 1AT, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The first heated buffer fluid branch exiting the fifth heat exchanger is flowed to the buffer fluid tank for reuse. The third, fourth and fifth heat exchangers are coupled to one another in series relative to the flow of the heated buffer fluid.

In some implementations, the first heated buffer fluid stream can be flowed in series through the different plants. For example, the first heated buffer fluid can be flowed first to the amine regeneration plant, then to the sour water stripper plant and then to the aromatics complex benzene extraction unit. The first heated buffer fluid exiting the final exchanger(s) in the series can then be flowed to the buffer fluid tank. The buffer fluid from the buffer fluid tank can then be flowed to the different plants to restart the waste heat recovery and reuse cycle.

FIG. 1AU shows the sulfur recovery plant 602 in a crude oil refinery facility. The second heated buffer fluid stream is flowed to the sulfur recovery plant 602. An amine regenerator bottoms stream is heated using the second heated buffer fluid stream in a sixth heat exchanger with a thermal duty that can range between about 15 MW and 25 MW (for example, 21 MW). The sixth heat exchanger is coupled to, in series with and is downstream of the second heat exchanger relative to flow of the buffer fluid. As shown in FIG. 1AU, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AV also shows the aromatics complex benzene extraction unit 618 in a crude oil refinery facility. The second heated buffer fluid stream is flowed to the aromatics complex benzene extraction unit 618. An aromatics plant raffinate splitter bottoms stream can be heated using the second heated buffer fluid stream in a seventh heat exchanger with a thermal duty that can range between about 5 MW and 15 MW (for example, 8.6 MW). The seventh heat exchanger is coupled to, in series with and is downstream of the second heat exchanger relative to the buffer fluid flow. As shown in FIG. 1AV, the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

The second heated buffer fluid stream exiting the seventh heat exchanger is flowed to the buffer fluid tank for reuse. The sixth and the seventh heat exchangers are coupled to one another in series relative to the flow of the heated buffer fluid. The set of the sixth and the seventh heat exchangers and the set of the third, fourth, and fifth heat exchangers are coupled in parallel to one another relative to the flow of the buffer fluid.

In some implementations, the second heated buffer fluid stream can be flowed in series through the different plants.

For example, the second heated buffer fluid can be flowed first to the aromatics complex benzene extraction unit and then the sulfur recovery plant. The second heated buffer fluid exiting the final exchanger(s) in the series can then be flowed to the buffer fluid tank. The buffer fluid from the buffer fluid tank can then be flowed to the different plants to restart the waste heat recovery and reuse cycle.

FIG. 1AW shows a natural gas steam reforming hydrogen plant 608 in a crude oil refinery facility that includes a low temperature shift (LTS) converter product stream. A natural gas steam reforming hydrogen plant 608 can be directly thermally integrated with a gas separation plant 606. The LTS converter product stream can directly heat a C3/C4 splitter bottoms stream in an eighth heat exchanger with a thermal duty that can range between about 1 MW and 10 MW (for example, 4.3 MW). The LTS converter product stream can directly heat a de-ethanizer bottoms stream in a ninth heat exchanger with a thermal duty that can range between about 5 MW and 15 MW (for example, 9.9 MW). The ninth heat exchanger is coupled to, in series with and is downstream of the eighth heat exchanger relative to the flow of the LTS converter product stream. The series of LTS converter product heat exchangers transfer heat directly to other process streams that would have otherwise been discharged to the environment. The LTS converter product stream is returned to the hydrogen plant 608 for further processing.

In some implementations, the order of LTS converter product stream intra-plant can be different, for example, the LTS converter product stream can flow first through the de-ethanizer bottoms exchanger and then the C3/C4 splitter bottoms exchanger. The LTS converter product stream exiting the final exchanger(s) in the series can then be flowed to the LTS converter product line.

FIG. 1AX shows the gas separation plant 604 in the crude oil refinery facility. The heated C3/C4 splitter bottoms stream can be flowed to the gas separation plant 604. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In addition, the heated de-ethanizer bottoms stream can also be flowed to the gas separation plant 604. As shown in FIG. 1AX, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat separately and indirectly from the aromatics complex xylene products separation and directly from the natural gas steam reforming hydrogen plant can result in decreasing or eliminating the heat energy for heating the sulfur recovery plant, the aromatics complex benzene extraction plant, the amine regeneration plant, the sour water stripper plant, the gas separation plant or combinations of them such as by about 130 MW.

Configuration 5

FIGS. 1AY-1BN illustrate configurations and related scheme details for thermally integrating different refining plants in the crude oil refining facility. The thermal integration described in these configurations and illustrated in FIGS. 1AY-1BN can reduce the crude oil refining facility's energy consumption (for example, heating and cooling utilities). For example, a reduction in energy consumption by about 130 MW, for example, 129.7 MW, can translate to at least about 20%, for example, 19.95%, of the energy consumption in the crude oil refining facility. In certain schemes, a process stream from one refining plant can be used to directly heat another process stream from another, different refining plant. In certain configurations, heat exchange between process streams can be implemented using an intermediate buffer fluid, for example, water, oil, or other buffer fluid.

Configuration 5—Scheme A

In some implementations, multiple first streams in the multiple first plants can be directly heated using a second stream from a second plant, multiple third streams in the multiple third plants can be directly heated using a fourth stream from a second plant, and multiple fifth streams in a fifth plant can be directly heated using a sixth stream from a sixth plant. In some instances, the multiple first plants and the multiple third plants share a common plant. In some implementations, the multiple first plants in the crude oil refinery can include an aromatics complex benzene extraction plant, a sour water stripper plant, and an amine regeneration plant, and the multiple first streams can include a benzene column bottoms, a sour water stripper bottoms, and an acid gas regenerator bottoms. The second plant can include an aromatics complex, which can include an aromatics complex xylene products separation unit, the second stream can include a raffinate column overheads stream, and the fourth stream can include an extract column overheads stream. In some implementations, the multiple third plants in the crude oil refinery can include a sulfur recovery plant and an aromatics complex benzene extraction plant, and the multiple third streams can include an amine regenerator bottoms and a raffinate splitter bottoms streams. In some instances, the shared common plant can be an aromatics complex benzene extraction unit. The fifth plant can include a gas separations plant, and the multiple fifth plant streams can include a de-ethanizer bottoms and a C3/C4 splitter bottoms streams. The sixth plant can include a diesel hydrotreating plant, and the sixth stream can include a diesel stripper bottoms stream.

FIG. 1AY shows an aromatics complex xylene products separation unit 620 in a crude oil refinery facility that includes a raffinate column overheads stream. The raffinate overheads column stream can be flowed in the plant as a single stream and split into multiple streams or it can be flowed into the plant as multiple streams to facilitate heat recovery. A first raffinate column overhead stream can directly heat a benzene column bottoms stream in a first heat exchanger with a thermal duty that can range between about 1 MW to 10 MW (for example, 6 MW). A second raffinate column overheads stream can directly heat a sour water stripper bottoms stream in the sour water stripper plant 610 in a second heat exchanger with a thermal duty that can range between about 25 MW and 35 MW (for example, 32 MW). A third raffinate column overheads stream can directly heat an acid gas regenerator bottoms stream with a thermal duty that can range between about 45 MW and 55 MW (for example, 47.8 MW). In this manner, the first heat exchanger, the second heat exchanger, and the third heat exchanger can be coupled to each other in parallel relative to the flow of raffinate column overheads. The parallel set of raffinate column overhead exchangers transfer heat directly to other process streams that would have otherwise been discharged to the environment. In an alternative embodiment, the cooling requirement of the raffinate column overheads stream can be 0 MW because the alternative flow path disclosed in this configuration may satisfy the entire cooling requirement for the raffinate column overheads stream for the operation of the raffinate column. The raffinate column overheads streams are recombined and returned to the aromatics plant xylene products separation unit 620 for further processing.

The aromatics complex xylene products separation unit 620 also includes an extract column overheads stream. The extract column overheads stream can be flowed in the plant as a single stream and split into multiple streams or it can be flowed into the plant as multiple streams to facilitate heat recovery. As shown in FIG. 1AY, the first extract column overheads stream can directly heat an amine regenerator bottoms stream in a fourth heat exchanger with a thermal duty that can range between about 15 MW and 25 MW (for example, 21 MW). The second extract column overheads stream can directly heat a raffinate splitter bottom stream in a fifth heat exchanger with a thermal duty that can range between about 5 MW and 15 MW (for example, 8.6 MW). In this manner, the fourth and the fifth heat exchangers can be coupled to each other in parallel relative to the flow of extract column overheads. The parallel set of extract column overhead exchangers transfer heat directly to other process streams that would have otherwise been discharged to the environment. In an alternative embodiment, the cooling requirement of the extract column overheads stream can be 0 MW because the alternative flow path disclosed in this configuration may satisfy the entire cooling requirement for the extract column overheads stream for the operation of the extract column. The extract column overheads stream are recombined and returned to the aromatics plant xylene products separation unit 620 for further processing.

FIG. 1BA shows the aromatics complex benzene extraction unit 618 in the crude oil refinery facility. The heated benzene column bottoms stream can be flowed to the benzene extraction plant 618. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1BE also shows the aromatics complex benzene extraction unit 618. The heated raffinate splitter column bottoms stream can also be flowed to the benzene extraction plant 618. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

FIG. 1BB shows the sour water stripper plant 610 in the crude oil refinery facility. The heated sour water stripper bottoms stream can be flowed to the sour water stripper plant 610. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1BC shows the amine regeneration plant 606 in the crude oil refinery facility. The heated acid gas regenerator bottom stream can be flowed to the amine regeneration plant 606. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

FIG. 1BD shows the sulfur recovery plant 602 in the crude oil refinery facility. The heated amine regenerator bottom stream can be flowed to the sulfur recovery plant 602. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AZ shows a diesel hydro-treating plant 600 in a crude oil refinery facility that includes a diesel stripper bottoms stream. A diesel hydro-treating plant 600 can be directly thermally integrated with a gas separation plant 606. A diesel stripper bottoms stream can directly heat a C3/C4 splitter bottoms stream in a sixth heat exchanger with a thermal duty that can range between about 1 MW and 10 MW (for example, 4.3 MW). The diesel stripper bottoms stream can directly heat a de-ethanizer bottom stream in a seventh heat exchanger with a thermal duty that can range between about 5 MW and 15 MW (for example, 9.9 MW). The seventh heat exchanger is coupled to, in series with and is downstream of the sixth heat exchanger relative to the flow of diesel stripper bottoms stream. The series of gas separation plant exchangers transfer heat directly to other process streams that would have otherwise been discharged to the environment. The diesel stripper bottoms stream is returned to the diesel hydrotreating plant 600 for further processing.

In some implementations, the order of diesel stripper bottoms stream intra-plant can be different, for example, the heated buffer fluid can flow first through the de-ethanizer bottoms exchanger and then the C3/C4 splitter bottoms exchanger. The diesel stripper bottoms stream exiting the final exchanger(s) in the series can then be flowed to the diesel stripper bottoms line.

FIG. 1BF shows the gas separation plant 604 in the crude oil refinery facility. The heated C3/C4 splitter bottom stream can be flowed to the gas separation plant 604. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In addition, the heated de-ethanizer bottom stream can also be flowed to the gas separation plant 604. As shown in FIG. 1BF, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat separately and directly from both an aromatics complex xylene products separation unit and a natural gas steam reforming hydrogen plant can result in decreasing or eliminating the heat energy to heat the gas separation plant stream, a sour water stripper plant, an amine regeneration plant, a sulfur recovery plant, an aromatics complex benzene extraction unit or combinations of them, such as by about 130 MW.

Configuration 5—Scheme B

In some implementations, multiple first streams in the multiple first plants can be indirectly heated using a second stream from a second plant, multiple third streams in the multiple third plants can be indirectly heated using a fourth stream from a second plant, and multiple fifth streams in a fifth plant can be directly heated using a sixth stream from a sixth plant. In some instances, the multiple first plants and the multiple third plants share a common plant. In some implementations, the multiple first plants in the crude oil refinery can include an aromatics complex benzene extraction plant, a sour water stripper plant, and an amine regeneration plant, and the multiple first streams can include a benzene column bottoms, a sour water stripper bottoms, and an acid gas regenerator bottoms. The second plant can include an aromatics complex, which can include an aromatics complex xylene products separation unit, the second stream can include a raffinate column overheads stream, and the fourth stream can include an extract column overheads stream. In some implementations, the multiple third plants in the crude oil refinery can include a sulfur recovery plant and an aromatics complex benzene extraction plant, and the multiple third streams can include an amine regenerator bottoms and a raffinate splitter bottoms streams. In some instances, the shared common plant can be an aromatics complex benzene extraction unit. The fifth plant can include a gas separations plant, and the multiple fifth plant streams can include a de-ethanizer bottoms and a C3/C4 splitter bottoms streams. The sixth plant can include a diesel hydrotreating plant, and the sixth stream can include a diesel stripper bottoms stream.

Indirectly heating the streams can include heating the streams through a buffer fluid, for example, oil, water, or other buffer fluid. A buffer fluid (for example, high pressure water) from a buffer fluid tank (for example, hot water tank) is flowed to the xylene products separation unit 620. The buffer fluid can be flowed into the plant as a single stream and split into multiple streams or it can be flowed into the plant as multiple streams. FIG. 1BG shows the buffer fluid is split into a first buffer fluid stream and a second buffer fluid stream.

FIG. 1BG shows an aromatics complex xylene products separation unit 620 in a crude oil refinery facility. A buffer fluid from a buffer fluid tank is flowed to an aromatics plant xylene products separation unit 620. The first buffer fluid stream can be heated using a raffinate column overheads stream in a first heat exchanger with a thermal duty that can range between about 80 MW and 90 MW (for example, 85.8 MW). The buffer fluid absorbs heat that would have otherwise been discharged to the environment. In an alternative embodiment, the cooling requirement of the raffinate column overheads stream can be 0 MW because the alternative flow path disclosed in this configuration may satisfy the entire cooling requirement for the raffinate column overheads stream for the operation of the raffinate column. The raffinate column overheads stream is returned to the xylene products separation unit 620 for further processing.

Also as shown in FIG. 1BG, a second buffer fluid stream can be heated using an extract column overheads stream in the aromatics plant xylene products separation unit 620 in a second heat exchanger with a thermal duty that can range between about 25 MW and 35 MW (for example, 29.6 MW). The buffer fluid absorbs heat that would have otherwise been discharged to the environment. In an alternative embodiment, the cooling requirement of the extract column overheads stream can be 0 MW because the alternative flow path disclosed in this configuration may satisfy the entire cooling requirement for the extract column overheads stream for the operation of the extract column. The extract column overheads stream is returned to the xylene products separation unit 620 for further processing.

The heated buffer fluid streams can be directed to a collection header (or in some embodiments, a heated or insulated buffer fluid tank or storage unit that can hold heated collected buffer fluid for a period before use) and then can be flowed to the amine regeneration plant 606, the sulfur recovery plant 602, the aromatics complex benzene extraction unit 618 and the sour water stripper plant 610, and combinations thereof. In some instances, the heated buffer fluid streams are maintained as a first heated buffer fluid stream and a second heated buffer fluid stream. In such instances, the first and second heated buffer fluid streams are not recombined in a collection header or fluid tank until they have transferred the thermal energy obtained in the second plant into the multiple streams of the multiple first plants.

FIG. 1BI shows the aromatics complex benzene extraction unit 618 in a crude oil refinery facility. The first heated buffer fluid stream is flowed to the benzene extraction unit 618. A benzene column bottoms stream is heated using the first heated buffer fluid stream in a third heat exchanger with a thermal duty that can range between about 1 MW and 10 MW (for example, 6 MW). The third heat exchanger is coupled to, in series with and is downstream of the first heat exchanger relative to the buffer fluid flow. As shown in FIG. 1BI, the steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1BJ shows the sour water stripper plant 610 in a crude oil refinery facility. The first heated buffer fluid stream is flowed to the sour water stripper plant 610. A sour water stripper bottoms stream is heated using the first heated buffer fluid stream in a fourth heat exchanger with a thermal duty that can range between about 25 MW and 35 MW (for example, 32 MW). The fourth heat exchanger is coupled to, in series with and is downstream of the first heat exchanger relative to the buffer fluid flow. As shown in FIG. 1BJ, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1BK shows the amine regeneration plant 606 in a crude oil refinery facility. The first heated buffer fluid stream is flowed to an amine regeneration plant 606. As shown in FIG. 1BK, an acid gas regenerator bottoms stream is heated using the first heated buffer fluid stream in a fifth heat exchanger with a thermal duty that can range between about 45 MW and 55 MW (for example, 47.8 MW). The fifth heat exchanger is coupled to, in series with and is downstream of the first heat exchanger relative to the buffer fluid flow. As shown in FIG. 1BK, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The first heated buffer fluid branch exiting the fifth heat exchanger is flowed to the buffer fluid tank for reuse. The third, fourth and fifth heat exchangers are coupled to one another in series relative to the flow of the heated buffer fluid.

In some implementations, the first heated buffer fluid stream can be flowed in series through the different plants. For example, the first heated buffer fluid can be flowed first to the amine regeneration plant, then to the sour water stripper plant and then to the aromatics complex benzene extraction unit. The first heated buffer fluid exiting the final exchanger(s) in the series can then be flowed to the buffer fluid tank. The buffer fluid from the buffer fluid tank can then be flowed to the different plants to restart the waste heat recovery and reuse cycle.

FIG. 1BL shows the sulfur recovery plant 602 in a crude oil refinery facility. The second heated buffer fluid stream is flowed to the sulfur recovery plant 602. An amine regenerator bottoms stream is heated using the second heated buffer fluid stream in a sixth heat exchanger with a thermal duty that can range between about 15 MW and 25 MW (for example, 21 MW). The sixth heat exchanger is coupled to, in series with and is downstream of the second heat exchanger relative to flow of the buffer fluid. As shown in FIG. 1BL, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1BM also shows the aromatics complex benzene extraction unit 618 in a crude oil refinery facility. The second heated buffer fluid stream is flowed to the aromatics complex benzene extraction plant unit 618. An aromatics plant raffinate splitter bottoms stream can be heated using the second heated buffer fluid stream in a seventh heat exchanger with a thermal duty that can range between about 5 MW and 15 MW (for example, 8.6 MW). The seventh heat exchanger is coupled to, in series with and is downstream of the second heat exchanger relative to the buffer fluid flow. As shown in FIG. 1BM the steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

The second heated buffer fluid stream exiting the seventh heat exchanger is flowed to the buffer fluid tank for reuse. The sixth and the seventh heat exchangers are coupled to one another in series relative to the flow of the heated buffer fluid. The set of the sixth and the seventh heat exchangers and the set of the third, fourth, and fifth heat exchangers are coupled in parallel to one another relative to the flow of the buffer fluid.

FIG. 1BN shows a diesel hydrotreating plant 600 in a crude oil refinery facility that includes a low temperature shift (LTS) converter product stream. A diesel hydrotreating plant 600 can be directly thermally integrated with a gas separation plant 606. A diesel stripper bottoms stream can directly heat a C3/C4 splitter bottoms stream in an eighth heat exchanger with a thermal duty that can range between about 1 MW and 10 MW (for example, 4.3 MW). The diesel stripper bottoms stream can directly heat a de-ethanizer bottom stream in a ninth heat exchanger with a thermal duty that can range between about 5 MW and 15 MW (for example, 9.9 MW). The ninth heat exchanger is coupled to, in series with and is downstream of the eighth heat exchanger relative to the flow of diesel stripper bottoms stream. The series of diesel stripper bottoms exchangers transfer heat directly to other process streams that would have otherwise been discharged to the environment. The diesel stripper bottoms stream is returned to the diesel hydrotreating plant 600 for further processing.

In some implementations, the order of diesel stripper bottoms stream intra-plant can be different, for example, the diesel stripper bottoms stream can flow first through the de-ethanizer bottoms exchanger and then the C3/C4 splitter bottoms exchanger. The diesel stripper bottoms stream exiting the final exchanger(s) in the series can then be flowed to the diesel stripper bottoms line.

FIG. 1BN shows the gas separation plant 604 in the crude oil refinery facility. The heated C3/C4 splitter bottom stream can be flowed to the gas separation plant 604. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In addition, the heated de-ethanizer bottom stream can also be flowed to the gas separation plant 604. As shown in FIG. 1BN, the steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat separately and indirectly from the aromatics complex xylene products separation and directly from the diesel hydrotreater plant can result in decreasing or eliminating the heat energy for heating the sulfur recovery plant, the aromatics complex benzene extraction plant, the amine regeneration plant, the sour water stripper plant, the gas separation plant or combinations of them such as by about 130 MW.

In summary, this disclosure describes configurations and related processing schemes of specific inter-plants and hybrid, intra- and inter-plants waste heat recovery schemes for thermal energy consumption reduction in integrated refining-petrochemical facilities synthesized for grassroots medium grade crude oil semi-conversion refineries to increase energy efficiency from specific portions of low grade waste heat sources. The disclosure also describes configurations and related processing schemes of specific inter-plants and hybrid, intra- and inter-plants waste heat recovery schemes for thermal energy consumption reduction in integrated refining-petrochemical facilities synthesized for integrated medium grade crude oil semi-conversion refineries and aromatics complex for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A system comprising:
 a plurality of oil refining plants in a crude oil refining facility, each oil refining plant configured to perform at least one oil refining process, each oil refining plant comprising a plurality of interconnected oil refining sub-systems, wherein a plurality of streams at respective temperatures flow between the plurality of oil refining sub-systems;
 a flow control system configured to:
  flow a gas separation plant stream comprising at least one of C2 to C4, an acid gas regenerator bottoms stream comprising a weak amine salt and a first aromatics complex stream comprising at least one of benzene, toluene or xylene from a gas separation plant comprising a de-ethanizer distillation column and a propane-butane splitter distillation column, an amine regeneration plant comprising an acid gas absorber column and an acid gas regenerator column, and an aromatics complex, respectively, of the plurality of oil refining plants to one or more heat exchangers of a heat exchanger system, and
  flow a second aromatics complex stream comprising at least one of benzene, toluene or xylene, the second aromatics complex stream being different from the first aromatics complex stream, from the aromatics complex of the plurality of oil refining plants to the one or more heat exchangers; and
 the heat exchanger system comprising the one or more heat exchangers, the heat exchanger system configured to transfer heat from the second aromatics complex stream to at least one of the gas separation plant stream, the acid gas regenerator bottoms stream and the first aromatics complex stream.

2. The system of claim 1, wherein a first plurality of plants comprises the gas separation plant, the amine regeneration plant, a sulfur recovery plant comprising an amine regenerator distillation column, a sour water stripper plant comprising a sour water stripper column, and the aromatics complex, and wherein a second plurality of plants comprises the aromatics complex which comprises an aromatics complex xylene products separation unit comprising an extract column and a raffinate column, an aromatics complex benzene extraction unit comprising a benzene distillation column, and the second plurality of plants further comprises a diesel hydro-treating plant comprising a diesel stripper column, and a hydrogen plant comprising a steam reforming furnace and a shift conversion vessel.

3. The system of claim 2, wherein the heat exchanger system is configured to directly transfer heat, wherein, to directly transfer the heat, the heat exchanger system comprises:
 a first heat exchanger configured to heat an acid gas regenerator bottoms stream using a first branch of the second aromatics complex stream which comprises a raffinate column overheads stream in the aromatics complex xylene products separation unit,
 a second heat exchanger configured to heat a benzene column bottoms stream in the aromatics complex benzene extraction unit using a second branch of the raffinate column overheads stream,
 a third heat exchanger configured to heat a raffinate splitter bottoms stream in the aromatics complex using a third branch of the raffinate column overheads stream,
 a fourth heat exchanger configured to heat a C3/C4 splitter bottoms stream in the gas separation plant using a first branch of the second aromatics complex stream which comprises an aromatics complex xylene separation section extract column overheads stream in the aromatics complex xylene products separation unit,
 a fifth heat exchanger configured to heat a de-ethanizer bottoms stream in the gas separation plant using a second branch of the aromatics complex xylene separation section extract column overheads stream, and
 wherein the flow control system is configured to:
  flow the heated acid gas regenerator bottoms stream to the amine regeneration plant,
  flow the heated benzene column bottoms cold stream to the aromatics complex benzene extraction unit in the aromatics complex,
  flow the heated raffinate splitter bottoms stream to the aromatics complex benzene extraction unit in the aromatics complex, and
  flow the heated C3/C4 splitter bottoms stream and the heated de-ethanizer bottom stream to the gas separation plant.

4. The system of claim 3, wherein the first heat exchanger, the second heat exchanger and the third heat exchanger are fluidically coupled to each other in parallel, wherein the fourth heat exchanger and the fifth heat exchanger are fluidically coupled to each other in parallel.

5. The system of claim 2, wherein the heat exchanger system is configured to directly transfer heat, wherein, to directly transfer the heat, the heat exchanger system comprises:
 a first heat exchanger configured to heat a benzene column bottoms stream in the aromatics complex benzene extraction unit using a first branch of the second aromatics complex stream which comprises an aromatics complex xylene products separation raffinate column overheads stream,
 a second heat exchanger configured to heat a sour water stripper bottom stream in the sour water stripper plant using a second branch of the aromatics complex xylene products separation raffinate column overheads stream,
 a third heat exchanger configured to heat an amine regenerator bottom stream using a third branch of the aromatics complex xylene products separation raffinate column overheads stream, a fourth heat exchanger configured to heat a raffinate splitter bottoms stream in the aromatics complex benzene extraction unit using a first branch of the second aromatics complex stream which comprises an aromatics complex xylene separation section extract column overheads stream in the aromatics complex xylene products separation unit, a fifth heat exchanger configured to heat a C3/C4 splitter bottoms stream in the gas separation plant using a second branch of the aromatics complex xylene separation section extract column overheads stream, a sixth heat exchanger configured to heat a de-ethanizer bottoms stream in the gas separation plant using a third branch of the aromatics complex xylene separation section extract column overheads stream, and wherein the flow control system is configured to:
flow the heated benzene column bottoms stream and the heated raffinate splitter bottoms stream to the aromatics complex benzene extraction unit,
flow the heated sour water stripper stream to the sour water stripper plant,
flow the heated amine regenerator bottom stream to the sulfur recovery plant, and
flow the heated C3/C4 splitter bottoms stream and the heated de-ethanizer bottom stream to the gas separation plant.

6. The system of claim 5, wherein the first heat exchanger, the second heat exchanger and the third heat exchanger are fluidically coupled to each other in parallel, wherein the fourth heat exchanger, the fifth heat exchanger and the sixth heat exchanger are fluidically coupled to each other in parallel.

7. The system of claim 2, wherein the heat exchanger system is configured to directly transfer heat, wherein, to directly transfer heat, the heat exchanger system comprises:
a first heat exchanger configured to heat a benzene column bottoms stream in the aromatics complex benzene extraction unit using a first branch of the second aromatics complex stream which comprises an aromatics complex xylene products separation raffinate column overheads stream,
a second heat exchanger configured to heat an acid gas regenerator bottoms stream in the amine regeneration plant using a second branch of the aromatics complex xylene products separation raffinate column overheads stream,
a third heat exchanger configured to heat a sulfur recovery bottom cold stream in the sulfur recovery plant using a third branch of the aromatics complex xylene products separation raffinate column overheads stream,
a fourth heat exchanger configured to heat a raffinate splitter bottoms stream in the aromatics complex benzene extraction unit using a first branch of the second aromatics complex stream which comprises an aromatics complex xylene separation section extract column overheads stream in the aromatics complex xylene products separation unit,
a fifth heat exchanger configured to heat a C3/C4 splitter bottoms stream in the gas separation plant using a second branch of the aromatics complex xylene separation section extract column overheads stream,
a sixth heat exchanger configured to heat a de-ethanizer bottoms stream in the gas separation plant using a third branch of the aromatics complex xylene separation section extract column overheads stream, and wherein the flow control system is configured to:
flow the heated benzene column bottoms stream and the heated raffinate splitter bottoms stream to the aromatics complex benzene extraction unit,
flow the heated acid gas regenerator stream to the amine regeneration plant,
flow the heated sulfur recovery bottom cold stream to the sulfur recovery stream, and
flow the heated C3/C4 splitter bottoms stream and the heated de-ethanizer bottom stream to the gas separation plant.

8. The system of claim 7, wherein the first heat exchanger, the second heat exchanger and the third heat exchanger are fluidically coupled to each other in parallel, wherein the fourth heat exchanger, the fifth heat exchanger and the sixth heat exchanger are fluidically coupled to each other in parallel.

9. The system of claim 2, wherein the heat exchanger system is configured to directly transfer heat, wherein, to directly transfer the heat, the heat exchanger system comprises:
a first heat exchanger configured to heat a benzene column bottoms stream in the aromatics complex benzene extraction unit using a first branch of the second aromatics complex stream which comprises an aromatics complex xylene products separation raffinate column overheads stream,
a second heat exchanger configured to heat a sour water stripper bottom cold stream in the sour water stripper plant using a second branch of the aromatics complex xylene products separation raffinate column overheads stream,
a third heat exchanger configured to heat an acid gas regenerator bottoms stream in the amine regeneration plant using a third branch of the aromatics complex xylene products separation raffinate column overheads stream,
a fourth heat exchanger configured to heat an amine regenerator bottom cold stream in the sulfur recovery plant using a first branch of the second aromatics complex stream which comprises an aromatics complex xylene separation section extract column overheads stream in the aromatics complex xylene products separation unit,
a fifth heat exchanger configured to heat a raffinate splitter bottoms stream using a second branch of the aromatics complex xylene separation section extract column overheads stream,
a sixth heat exchanger configured to heat a C3/C4 splitter bottoms stream in the gas separation plant using a post-low temperature shift (LTS) hydrogen plant stream in the hydrogen plant comprising the shift conversion vessel comprising a LTS conversion vessel,
a seventh heat exchanger configured to heat a de-ethanizer bottoms stream in the gas separation plant using the post-LTS hydrogen plant stream exiting the sixth heat exchanger, and wherein the flow control system is configured to:
flow the heated benzene column bottoms stream and the heated raffinate splitter bottoms stream to the aromatics complex benzene extraction unit,
flow the heated sour water stripper bottom cold stream to the sour water stripper plant,
flow the heated acid gas regenerator bottoms stream to the amine regeneration plant,
flow the heated amine regenerator bottom cold to the sulfur recovery stream, and flow the heated C3/C4 splitter bottoms stream and the heated de-ethanizer bottom stream to the gas separation plant.

10. The system of claim 9, wherein the first heat exchanger, the second heat exchanger and the third heat exchanger are fluidically coupled to each other in parallel, wherein the fourth heat exchanger and the fifth heat exchanger are fluidically coupled to each other in parallel, wherein the sixth heat exchanger and the seventh heat exchanger are fluidically coupled to each other in series.

11. The system of claim 2, wherein the heat exchanger system is configured to directly transfer heat, wherein, to directly transfer the heat, the heat exchanger system comprises:
a first heat exchanger configured to heat a benzene column bottoms stream in the aromatics complex benzene extraction unit using a first branch of the second aromatics complex stream which comprises an aromatics complex xylene products separation raffinate column overheads stream,
a second heat exchanger configured to heat a sour water stripper bottom cold stream in the sour water stripper plant using a second branch of the aromatics complex xylene products separation raffinate column overheads stream,
a third heat exchanger configured to heat an acid gas regenerator bottoms stream in the amine regeneration plant using a third branch of the aromatics complex xylene products separation raffinate column overheads stream,
a fourth heat exchanger configured to heat an amine regenerator bottom cold stream in the sulfur recovery plant using a first branch of the second aromatics complex stream which comprises an aromatics complex xylene separation section extract column overheads stream in the aromatics complex xylene products separation unit,
a fifth heat exchanger configured to heat a raffinate splitter bottoms stream using a second branch of the aromatics complex xylene separation section extract column overheads stream,
a sixth heat exchanger configured to heat a C3/C4 splitter bottoms stream in the gas separation plant using a product stripper bottom stream in the diesel hydrotreating plant, and
a seventh heat exchanger configured to heat a de-ethanizer bottoms stream in the gas separation plant using the product stripper bottom stream in the diesel hydrotreating plant received from the sixth heat exchanger,
wherein the flow control system is configured to:
flow the heated benzene column bottoms stream and the heated raffinate splitter bottoms stream to the aromatics complex benzene extraction unit,
flow the heated sour water stripper bottom cold stream to the sour water stripper plant,
flow the heated acid gas regenerator bottoms stream to the amine regeneration plant,
flow the heated amine regenerator bottom cold to the sulfur recovery stream, and
flow the heated C3/C4 splitter bottoms stream and the heated de-ethanizer bottom stream to the gas separation plant.

12. The system of claim 11, wherein the first heat exchanger, the second heat exchanger and the third heat exchanger are fluidically coupled to each other in parallel, wherein the fourth heat exchanger and the fifth heat exchanger are fluidically coupled to each other in parallel, wherein the sixth heat exchanger and the seventh heat exchanger are fluidically coupled to each other in series.

13. The system of claim 2, wherein the heat exchanger system is configured to indirectly heat, wherein, to indirectly heat, the heat exchanger system comprises a first heat exchanger configured to heat the buffer fluid using the second aromatics complex stream which comprises an aromatics complex xylene products separation raffinate column overheads stream in the aromatics complex xylene products separation unit,
wherein the flow control system is configured to flow a first branch of the heated buffer fluid to the amine regeneration plant,
wherein the heat exchanger system comprises a second heat exchanger configured to heat an acid gas regenerator bottoms stream in the amine regeneration plant using the first branch of the heated buffer fluid,
wherein the flow control system is configured to flow a second branch of the heated buffer fluid to the aromatics complex,
wherein the heat exchanger system comprises a third heat exchanger configured to heat a benzene column bottoms stream in the aromatics complex benzene extraction unit using the second branch of the heated buffer fluid,
wherein the flow control system is configured to flow the second branch exiting the third heat exchanger to the aromatics complex,
wherein the heat exchanger system comprises a fourth heat exchanger configured to heat a raffinate splitter bottoms stream in the aromatics complex using the second branch of the heated buffer fluid exiting the third heat exchanger,
wherein the flow control system is configured to flow the second branch exiting the fourth heat exchanger to the gas separation plant,
wherein the heat exchanger system comprises a fifth heat exchanger configured to heat a C3/C4 splitter bottoms stream in the gas separation plant using the second branch of the heated buffer fluid exiting the fourth heat exchanger,
wherein the flow control system is configured to flow the second branch to a sixth heat exchanger in the gas separation plant, and
wherein the heat exchanger system comprises a sixth heat exchanger configured to heat a de-ethanizer bottoms stream in the gas separation plant using the second branch of the heated buffer fluid exiting the fifth heat exchanger.

14. The system of claim 13, wherein the first heat exchanger and the second heat exchanger are fluidically coupled to each other in series, wherein the first heat exchanger and the third heat exchanger are fluidically coupled to each other in series, wherein the third heat exchanger and the fourth heat exchanger are fluidically coupled to each other in series, wherein the fourth heat exchanger and the fifth heat exchanger are fluidically coupled to each other in series, wherein the fourth heat exchanger and the sixth heat exchanger are fluidically coupled to each other in series, and wherein the second heat exchanger and a combination of the third heat exchanger, the fourth heat exchanger, the fifth heat exchanger and the sixth heat exchanger are fluidically coupled to each other in parallel.

15. The system of claim 13, wherein the first branch and the second branch are flowed in parallel, and wherein the flow control system is configured to:

combine the first branch exiting the second heat exchanger and the second branch exiting the sixth heat exchanger; and flow the combined first branch and the second branch to a buffer fluid tank.

16. The system of claim 2, wherein the heat exchanger system is configured to indirectly heat, wherein, to indirectly heat, the heat exchanger system comprises a first heat exchanger configured to heat the buffer fluid using the second aromatics complex stream which comprises an aromatics complex xylene products separation raffinate column overheads stream in the aromatics complex xylene products separation unit, wherein the flow control system is configured to flow the heated buffer fluid exiting the first heat exchanger to the aromatics complex benzene extraction unit, wherein the heat exchanger system comprises a second heat exchanger configured to heat a benzene column bottoms stream in the aromatics complex benzene extraction unit using the heated buffer fluid exiting the first heat exchanger, wherein the flow control system is configured to flow a first branch of the heated buffer fluid exiting the second heat exchanger to the sour water stripper plant, wherein the heat exchanger system comprises a third heat exchanger configured to heat a sour water stripper bottom stream in the sour water stripper plant using the first branch of the heated buffer fluid exiting the second heat exchanger, wherein the flow control system is configured to flow a second branch of the heated buffer fluid exiting the second heat exchanger to the sulfur recovery plant, wherein the heat exchanger system comprises a fourth heat exchanger configured to heat an amine regenerator bottom stream in the sulfur recovery plant using the second branch of the heated buffer fluid exiting the second heat exchanger, wherein the flow control system is configured to:
combine the buffer fluid exiting the third heat exchanger and buffer fluid exiting the fourth heat exchanger to form a combined buffer fluid, and
flow the combined buffer fluid to the aromatics complex benzene extraction unit, wherein the heat exchanger system comprises a fifth heat exchanger configured to heat a raffinate splitter bottoms stream using the combined buffer fluid, wherein the flow control system is configured to flow the combined buffer fluid exiting the fifth heat exchanger to the gas separation plant, wherein the heat exchanger system comprises a sixth heat exchanger configured to heat a C3/C4 splitter bottoms stream in the gas separation plant using the buffer fluid exiting the fifth heat exchanger to the gas separation plant, and wherein the heat exchanger system comprises a seventh heat exchanger configured to heat a de-ethanizer bottoms stream in the gas separation plant using the heated buffer fluid exiting the sixth heat exchanger.

17. The system of claim 16, wherein the first heat exchanger and the second heat exchanger are fluidically coupled to each other in series, wherein the second heat exchanger and the third heat exchanger are fluidically coupled to each other in series, wherein the second heat exchanger and the fourth heat exchanger are fluidically coupled to each other in series, wherein the third heat exchanger and the fourth heat exchanger are fluidically coupled to each other in parallel, wherein the fifth heat exchanger is fluidically coupled to a combination of the third heat exchanger and the fourth heat exchanger in series, wherein the fifth heat exchanger and the sixth heat exchanger are fluidically coupled to each other in series, wherein the sixth heat exchanger and the seventh heat exchanger are fluidically coupled to each other in series.

18. The system of claim 17, wherein the flow control system is configured to flow the buffer fluid exiting the seventh heat exchanger to a buffer fluid tank.

19. The system of claim 2, wherein the heat exchanger system is configured to indirectly heat, wherein, to indirectly heat, the heat exchanger system comprises a first heat exchanger configured to heat a first branch of the buffer fluid using the second aromatics complex stream which comprises an aromatics complex xylene products separation raffinate column overheads stream in the aromatics complex xylene products separation unit, wherein the flow control system is configured to flow the heated first branch exiting the first heat exchanger to the aromatics complex benzene extraction unit, wherein the heat exchanger system comprises a third heat exchanger configured to heat a benzene column bottoms stream in the aromatics complex benzene extraction unit using the heated first branch, wherein the flow control system is configured to flow the first branch of the buffer fluid exiting the third heat exchanger to the sulfur recovery plant, wherein the heat exchanger system comprises a fourth heat exchanger configured to heat an amine regenerator bottom stream in the sulfur recovery plant using the first branch of the heated buffer fluid exiting the third heat exchanger, wherein the flow control system is configured to flow the first branch of the heated buffer fluid exiting the fourth heat exchanger to the amine regeneration plant, and wherein the heat exchanger system comprises a fifth heat exchanger configured to heat an acid gas regenerator bottoms stream using the first branch of the heated buffer fluid exiting the fourth heat exchanger.

20. The system of claim 19, wherein the heat exchanger system comprises a second heat exchanger configured to heat a second branch of the buffer fluid using the second aromatics complex stream which comprises an extract column overheads stream in the aromatics complex xylene products separation unit, wherein the flow control system is configured to flow the heated second branch exiting the second heat exchanger to the aromatics complex benzene extraction unit, wherein the heat exchanger system comprises a sixth heat exchanger configured to heat a raffinate splitter bottoms stream in the aromatics complex benzene extraction unit using the heated second branch, wherein the flow control system is configured to flow the heated second branch exiting the sixth heat exchanger to the gas separation plant, wherein the heat exchanger system comprises a seventh heat exchanger configured to heat a C3/C4 splitter bottoms stream in the gas separation plant using the second branch of the heated buffer fluid exiting the sixth heat exchanger, and wherein the heat exchanger system comprises an eighth heat exchanger configured to heat a de-ethanizer bottoms stream in the gas separation plant using the heated buffer fluid exiting the seventh heat exchanger.

21. The system of claim 20, wherein the flow control system is configured to flow the heated buffer fluid exiting the fifth heat exchanger and the heated buffer fluid exiting the eighth heat exchanger to a buffer fluid tank.

22. The system of claim 20, wherein the first heat exchanger and the third heat exchanger are fluidically coupled to each other in series, wherein the third heat exchanger and the fourth heat exchanger are fluidically coupled to each other in series, wherein the fourth heat exchanger and the fifth heat exchanger are fluidically coupled to each other in series, wherein the second heat exchanger and the sixth heat exchanger are fluidically coupled to each other in parallel, wherein the sixth heat exchanger and a combination of the third heat exchanger, the fourth heat exchanger and the fifth heat exchanger are fluidically coupled to each other in parallel, wherein the sixth heat exchanger and the seventh heat exchanger are fluidically coupled to each other in series, wherein the seventh heat exchanger and the eighth heat exchanger are fluidically coupled to each other in series, wherein a combination of the sixth heat exchanger, the seventh heat exchanger and the eighth heat exchanger and the combination of the third heat exchanger, the fourth heat exchanger and the fifth heat exchanger are fluidically coupled to each other in parallel.

23. The system of claim 2, wherein the heat exchanger system is configured to indirectly heat, wherein, to indirectly heat, the heat exchanger system comprises a first heat exchanger configured to heat a first branch of the buffer fluid using the second aromatics complex stream which comprises an aromatics complex xylene products separation raffinate column overheads stream in the aromatics complex xylene products separation unit,
wherein the flow control system is configured to flow the heated first branch exiting the first heat exchanger to the aromatics complex benzene extraction unit,
wherein the heat exchanger system comprises a third heat exchanger configured to heat a benzene column bottoms stream in the aromatics complex benzene extraction unit using the heated first branch,
wherein the flow control system is configured to flow the first branch of the buffer fluid exiting the third heat exchanger to the sour water stripper plant,
wherein the heat exchanger system comprises a fourth heat exchanger configured to heat a sour water stripper bottom stream in the sour water stripper plant using the first branch of the heated buffer fluid exiting the third heat exchanger,
wherein the flow control system is configured to flow the first branch of the heated buffer fluid exiting the fourth heat exchanger to the amine regeneration plant,
wherein the heat exchanger system comprises a fifth heat exchanger configured to heat an acid gas regenerator bottoms stream using the first branch of the heated buffer fluid exiting the fourth heat exchanger,
wherein the heat exchanger system comprises a second heat exchanger configured to heat a second branch of the buffer fluid using an extract column overheads stream in the aromatics complex xylene products separation unit,
wherein the flow control system is configured to flow the heated second branch exiting the second heat exchanger to the sulfur recovery plant,
wherein the heat exchanger system comprises a sixth heat exchanger configured to heat an amine regenerator bottom stream in the sulfur recovery plant using the heated second branch;

wherein the flow control system is configured to flow the heated second branch exiting the sixth heat exchanger to the aromatics complex benzene extraction unit, and
wherein the heat exchanger system comprises a seventh heat exchanger configured to heat a raffinate splitter bottoms stream in the aromatics complex benzene extraction unit using the second branch of the heated buffer fluid exiting the sixth heat exchanger.

24. The system of claim 23, wherein the flow control system is configured to flow the first branch of the heated buffer fluid exiting the fifth heat exchanger and the second branch of the heated buffer fluid exiting the seventh heat exchanger to a buffer fluid tank.

25. The system of claim 24, wherein the heat exchanger system comprises:
an eighth heat exchanger configured to heat a C3/C4 splitter bottoms stream in the gas separation plant using a first branch of a post-low temperature shift (LTS) hydrogen plant stream in the hydrogen plant; and
a ninth heat exchanger configured to heat a de-ethanizer bottoms stream in the gas separation plant using a second branch of the post-LTS hydrogen plant stream in the hydrogen plant.

26. The system of claim 25, wherein the first heat exchanger and the third heat exchanger are fluidically coupled to each other in series, wherein the third heat exchanger and the fourth heat exchanger are fluidically coupled to each other in series, wherein the fourth heat exchanger and the fifth heat exchanger are fluidically coupled to each other in series, wherein the second heat exchanger and the sixth heat exchanger are fluidically coupled to each other in series, wherein the sixth heat exchanger and the seventh heat exchanger are fluidically coupled to each other in series, wherein the eighth heat exchanger and the ninth heat exchanger are fluidically coupled to each other in series.

27. The system of claim 2, wherein the heat exchanger system is configured to indirectly heat, wherein, to indirectly heat, the heat exchanger system comprises a first heat exchanger configured to heat a first branch of the buffer fluid using the second aromatics complex stream which comprises an aromatics complex xylene products separation raffinate column overheads stream in the aromatics complex xylene products separation unit,
wherein the flow control system is configured to flow the heated first branch exiting the first heat exchanger to the aromatics complex benzene extraction unit,
wherein the heat exchanger system comprises a third heat exchanger configured to heat a benzene column bottoms stream in the aromatics complex benzene extraction unit using the heated first branch,
wherein the flow control system is configured to flow the first branch of the buffer fluid exiting the third heat exchanger to the sour water stripper plant,
wherein the heat exchanger system comprises a fourth heat exchanger configured to heat a sour water stripper bottom stream in the sour water stripper plant using the first branch of the heated buffer fluid exiting the third heat exchanger,
wherein the flow control system is configured to flow the first branch of the heated buffer fluid exiting the fourth heat exchanger to the amine regeneration plant,
wherein the heat exchanger system comprises a fifth heat exchanger configured to heat an acid gas regenerator bottoms stream using the first branch of the heated buffer fluid exiting the fourth heat exchanger, wherein the heat exchanger system comprises a second heat exchanger configured to heat a second branch of the buffer fluid using an extract column overheads stream in the aromatics complex xylene products separation unit, wherein the flow control system is configured to flow the heated second branch exiting the second heat exchanger to the sulfur recovery plant, wherein the heat exchanger system comprises a sixth heat exchanger configured to heat a sulfur recovery amine regenerator bottom stream in the sulfur recovery plant using the heated second branch, wherein the flow control system is configured to flow the heated second branch exiting the sixth heat exchanger to the aromatics complex benzene extraction unit, and wherein the heat exchanger system comprises a seventh heat exchanger configured to heat a raffinate splitter bottoms stream in the aromatics complex benzene extraction unit using the second branch of the heated buffer fluid exiting the sixth heat exchanger.

28. The system of claim 27, wherein the flow control system is configured to flow the first branch of the heated buffer fluid exiting the fifth heat exchanger and the second branch of the heated buffer fluid exiting the seventh heat exchanger to a buffer fluid tank.

29. The system of claim 27, wherein the heat exchanger system comprises an eighth heat exchanger configured to heat a C3/C4 splitter bottoms stream in the gas separation plant using a first branch of a product stripper bottom stream in the diesel hydro-treating plant, and wherein the heat exchanger system comprises a ninth heat exchanger configured to heat a de-ethanizer bottoms stream in the gas separation plant using a second branch of the product stripper bottom stream in the diesel hydro-treating plant.

30. The system of claim 29, wherein the first heat exchanger and the third heat exchanger are fluidically coupled to each other in series, wherein the third heat exchanger and the fourth heat exchanger are fluidically coupled to each other in series, wherein the fourth heat exchanger and the fifth heat exchanger are fluidically coupled to each other in series, wherein the second heat exchanger and the sixth heat exchanger are fluidically coupled to each other in series, wherein the sixth heat exchanger and the seventh heat exchanger are fluidically coupled to each other in series, wherein the eighth heat exchanger and the ninth heat exchanger are fluidically coupled to each other in series.

* * * * *